United States Patent
Reed et al.

(10) Patent No.: US 9,850,505 B2
(45) Date of Patent: Dec. 26, 2017

(54) MICROORGANISMS AND METHODS FOR PRODUCING PYRUVATE, ETHANOL, AND OTHER COMPOUNDS

(71) Applicant: WISCONSIN ALUMNI RESEARCH FOUNDATION, Madison, WI (US)

(72) Inventors: Jennifer L. Reed, Madison, WI (US); Xiaolin Zhang, Newark, DE (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 0 days.

(21) Appl. No.: 14/848,646

(22) Filed: Sep. 9, 2015

(65) Prior Publication Data

US 2016/0068871 A1    Mar. 10, 2016

Related U.S. Application Data

(60) Provisional application No. 62/047,896, filed on Sep. 9, 2014.

(51) Int. Cl.

| | |
|---|---|
| *C12N 1/21* | (2006.01) |
| *C12P 7/40* | (2006.01) |
| *C12P 7/06* | (2006.01) |
| *C12N 1/19* | (2006.01) |
| *C12N 9/04* | (2006.01) |
| *C12N 9/88* | (2006.01) |

(52) U.S. Cl.
CPC .............. *C12P 7/40* (2013.01); *C12N 9/0006* (2013.01); *C12N 9/88* (2013.01); *C12P 7/06* (2013.01); *C12Y 101/01001* (2013.01); *C12Y 401/01001* (2013.01); *Y02E 50/17* (2013.01)

(58) Field of Classification Search
CPC ..... C12P 7/40; C12P 7/06; C12N 9/88; C12N 9/0006; Y02E 50/17; C12Y 401/01001; C12Y 101/01001
See application file for complete search history.

(56) References Cited

U.S. PATENT DOCUMENTS

2010/0304450 A1   12/2010 Eiteman et al.

FOREIGN PATENT DOCUMENTS

WO    WO 99/53035    10/1999

OTHER PUBLICATIONS

Zhou et al., Cell Mol Life Sci 63(19-20):2260-2290, 2006.*
Kozak, M., Gene 234:187-208, 1999.*
Altschul et al., Basic Local Alignment Research Tool, J. Mol. Biol. (1990)215, 403-410.
Asadollahi et al., Enhancing sesquiterpene production in *Saccharomyces cerevisiae* through in silico driven metabolic engineering. Metab Eng. 2009; 11(6):328-34.
Atsumi et al., Non-fermentative pathways for synthesis of branched-chain higher alcohols as biofuels. Nature. 2008;451(7174):86-U13.
Baba et al., Construction of *Escherichia coli* K-12 in-frame, single-gene knockout mutants: the Keio collection. Mol Syst Biol. 2006;2.
Baumler et al., The evolution of metabolic networks of *E. coli*. Bmc Syst Biol. 2011;5:182.
Beller et al., Genes Involved in Long-Chain Alkene Biosynthesis in Micrococcus luteus. Appl Environ Microb. 2010;76(4):1212-23.
Bologna et al., Characterization of *Escherichia coli* EutD: a Phosphotransacetylase of the Ethanolamine Operon. J Microbiol. 2010;48(5):629-36.
Causey et al., Engineering the metabolism of *Escherichia coli* W3110 for the conversion of sugar to redox-neutral and oxidized products: Homoacetate production. Proceedings of the National Academy of Sciences of the United States of America. 2003;100(3):825-32.
Causey et al., Engineering *Escherichia coli* for efficient conversion of glucose to pyruvate. Proceedings of the National Academy of Sciences of the United States of America. 2004;101(8):2235-40.
Datsenko et al., One-step inactivation of chromosomal genes in *Escherichia coli* K-12 using PCR products. Proceedings of the National Academy of Sciences of the United States of America. 2000;97(12):6640-5.
Feist et al., BO. Model-driven evaluation of the production potential for growth-coupled products of *Escherichia coli*. Metab Eng. 2010;12(3):173-86.
Fong et al., In silico design and adaptive evolution of *Escherichia coli* for production of lactic acid. Biotechnol Bioeng. 2005;91(5):643-8.
Hawkins et al., Production of benzylisoquinoline alkaloids in *Saccharomyces cerevisiae*. Nat Chem Biol. 2008;4(9):564-73.
Ingram et al., Genetic-Engineering of Ethanol-Production in *Escherichia-coli*. Appl Environ Microb. 1987;53(10):2420-5.
Karlin & Altschul, Applications and statistics for multiple high-scoring segments in molecular sequences, Proc. Natl. Acad.Sci, USA, Fol. 90, pp. 5873-5877, Jun. 1993.
Kim et al., Optimal metabolic and regulatory perturbations for metabolic engineering of microbial strains. Bmc Syst Biol. 2010;4.
Leonard et al., Combining metabolic and protein engineering of a terpenoid biosynthetic pathway for overproduction and selectivity control. Proceedings of the National Academy of Sciences of the United States of America. 2010;107(31):13654-9.

(Continued)

*Primary Examiner* — Delia Ramirez
(74) *Attorney, Agent, or Firm* — Daniel A. Blasiole; DeWitt Ross & Stevens S.C.

(57) ABSTRACT

Microorganisms comprising modifications for producing pyruvate, ethanol, and other compounds. The microorganisms comprise modifications that reduce or ablate activity of one or more of pyruvate dehydrogenase, 2-oxoglutarate dehydrogenase, phosphate acetyltransferase, acetate kinase, pyruvate oxidase, lactate dehydrogenase, cytochrome terminal oxidase, succinate dehydrogenase, 6-phosphogluconate dehydrogenase, glutamate dehydrogenase, pyruvate formate lyase, pyruvate formate lyase activating enzyme, and isocitrate lyase. The microorganisms optionally comprise modifications that enhance expression or activity of pyruvate decarboxylase and alcohol dehydrogenase. The microorganisms are optionally evolved in defined media to enhance specific production of one or more compounds. Methods of producing compounds with the microorganisms are provided.

21 Claims, 14 Drawing Sheets

(56) References Cited

OTHER PUBLICATIONS

Miller et al., Experiments in Molecular Genetics. Cold Spring Harbor Laboratory, (1972), 433 Entire Book Not Provided.

Mills et al., Cellulosic hydrolysate toxicity and tolerance mechanisms in *Escherichia coli*. Biotechnol Biofuels. 2009;2.

Nagy et al., Formyltetrahydrofolate Hydrolase, a Regulatory Enzyme That Functions to Balance Pools of Tetrahydrofolate and One-Carbon Tetrahydrofolate Adducts in *Escherichia-coli*. Journal of Bacteriology. 1995;177(5):1292-8.

Nakamura et al., Metabolic engineering for the microbial production of 1,3-propanediol. Curr Opin Biotech. 2003;14(5):454-9.

Neidhardt et al., Physiology of the bacterial cell: a molecular approach. Sunderland, Mass: Sinauer Associates; 1990.

Olins et al., A Novel Sequence Element Derived from Bacteriophage T7 mRNA Acts as an Enhancer of Translation of the lacZ Gene in *Escherichia coli*, The Journal of Biological Chemistry, vol. 264, No. 29, pp. 16973-16976 1989.

Park et al., Metabolic engineering of *Escherichia coli* for the production of L-valine based on transcriptome analysis and in silico gene knockout simulation. Proceedings of the National Academy of Sciences of the United States of America. 2007;104(19):7797-802.

Peng et al., Global metabolic regulation analysis for *Escherichia coli* K12 based on protein expression by 2-dimensional electrophoresis and enzyme activity measurement. Applied Microbiology and Biotechnology. 2003;61(2):163-78.

Pfeifer et al., Biosynthesis of complex polyketides in a metabolically engineered strain of *E-coli*. Science. 2001;291(5509):1790-2.

Reed et al., An expanded genome-scale model of *Escherichia coli* K-12 (iJR904 GSM/GPR). Genome Biol. 2003;4(9).

Ro et al., Production of the antimalarial drug precursor artemisinic acid in engineered yeast. Nature. 2006;440(7086):940-3.

Sawers et al., a glycyl radical solution: oxygen-dependent interconversion of pyruvate formate-lyase. Molecular Microbiology. 1998;29(4):945-54.

Sawers et al., The glycyl radical enzyme TdcE can replace pyruvate formate-lyase in glucose fermentation. Journal of Bacteriology. 1998;180(14):3509-16.

Schirmer et al., Microbial Biosynthesis of Alkanes. Science. 2010;329(5991):559-62.

Schwalbach et al., Complex Physiology and Compound Stress Responses during Fermentation of Alkali-Pretreated Corn Stover Hydrolysate by an *Escherichia coli* Ethanologen. Appl Environ Microb. 2012;78(9):3442-57.

Siewers et al., Implementation of Communication-Mediating Domains for Non-Ribosomal Peptide Production in *Saccharomyces cerevisiae*. Biotechnol Bioeng. 2010;106(5):841-4.

Steen et al., Microbial production of fatty-acid-derived fuels and chemicals from plant biomass. Nature. 2010;463(7280):559-U182.

Tarmy et al., Kinetics of *Escherichia coli* B D-Lactate Dehydrogenase and Evidence for Pyruvate-Controlled Change in Conformation. Journal of Biological Chemistry. 1968;243(10):2587.

Tomar et al., The effect of acetate pathway mutations on the production of pyruvate in *Escherichia coli*. Applied Microbiology and Biotechnology. 2003;62(1):76-82.

Toya et al., Metabolic regulation analysis of wild-type and arcA mutant *Escherichia coli* under nitrate conditions using different levels of omics data. Molecular bioSystems. 2012;8(10):2593-604.

Wang et al., Production of pyruvate in *Saccharomyces cerevisiae* through adaptive evolution and rational cofactor metabolic engineering. Biochem Eng J. 2012;67:126-31.

Wierckx et al., Engineering of solvent-tolerant Pseudomonas putida S12 for bioproduction of phenol from glucose. Appl Environ Microb. 2005;71(12):8221-7.

Wieschalka et al., Engineering Corynebacterium glutamicum for the production of pyruvate. Applied Microbiology and Biotechnology. 2012;94(2):449-59.

Xu et al., Regulation of thiamine synthesis in *Saccharomyces cerevisiae* for improved pyruvate production. Yeast. 2012;29(6):209-17.

Zha et al., Improving cellular malonyl-CoA level in *Escherichia coli* via metabolic engineering. Metab Eng. 2009;11(3):192-8.

Zhang et al., Metabolic evolution of energy-conserving pathways for succinate production in *Escherichia coli*. Proceedings of the National Academy of Sciences of the United States of America. 2009;106(48):20180-5.

Zhou et al., Evaluation of Genetic Manipulation Strategies on d-Lactate Production by *Escherichia coli*. Curr Microbiol. 2011;62(3):981-9.

Zhu et al., High Glycolytic Flux Improves Pyruvate Production by a Metabolically Engineered *Escherichia coli* Strain. Appl Environ Microb. 2008;74(21):6649-55.

* cited by examiner

MICROORGANISMS AND METHODS FOR PRODUCING PYRUVATE, ETHANOL, AND OTHER COMPOUNDS

STATEMENT REGARDING FEDERALLY SPONSORED RESEARCH

This invention was made with government support under DE-FC02-07ER64494, DE-SC0008103 awarded by the U.S. Department of Energy. The government has certain rights in the invention.

BACKGROUND

Over the past decade a number of chemical companies have begun to develop infrastructures for the production of compounds using bio-based processes. Considerable progress has been reported toward new processes for producing commodity chemicals such as ethanol, lactic acid, 1,3-propanediol, and adipic acid. In addition, advances have been made in the genetic engineering of microbes for higher value specialty compounds such as acetate, polyketides, and carotenoids.

Pyruvate is a starting material for synthesizing a variety of biofuels and chemicals. Industrially, pyruvate is produced via dehydration and decarboxylation of calcium tartrate, a byproduct of the wine industry. This process involves toxic solvents and is energy intensive with an estimated production cost of $8,650 per ton of pyruvate. Microbial pyruvate production is based primarily upon two microorganisms, a multi-vitamin auxotroph of the yeast *T. glabrata* and a lipoic auxotroph of *E. coli* containing an F1ATPase mutation. The estimated cost of pyruvate production via microbial fermentation with such strains is estimated to be $1,255 per ton of pyruvate, an 85% savings. Increasing the yield of pyruvate would increase the savings even further.

Ethanol is mainly of interest as a petrol additive, or substitute, because ethanol-blended fuel produces a cleaner, more complete combustion that reduces greenhouse gas and toxic emissions. The production of ethanol in the US has increased tremendously in recent years, and demand is projected to increase even further. As a consequence of the surge in demand for biofuels, ethanol-producing microorganisms are of considerable interest due to their potential for the production of bioethanol. To keep in step with the growing demand for biofuels, the engineering of new strains of fermentative microorganisms that can efficiently produce ethanol will be required.

There is a need for microorganisms that efficiently produce pyruvate, ethanol, or other commodity chemicals.

SUMMARY OF THE INVENTION

The present invention addresses the aforementioned needs by providing microorganisms with increased production of pyruvate, ethanol, or other commodity chemicals. Methods of producing commodity chemicals with the microorganisms described herein are also provided.

One aspect of the invention is a microorganism comprising modifications that reduce or ablate activity of one or more enzymes in a first set, one or more enzymes in a second set, and enzymes in a third set. The enzymes in the first set are selected from the group consisting of pyruvate dehydrogenase and 2-oxoglutarate dehydrogenase. The enzymes in the second set are selected from the group consisting of phosphate acetyltransferase, acetate kinase, and pyruvate oxidase. The enzymes in the third set comprise lactate dehydrogenase and one or more enzymes selected from the group consisting of cytochrome terminal oxidase and succinate dehydrogenase; lactate dehydrogenase and one or more enzymes selected from the group consisting of 6-phosphogluconate dehydrogenase and glutamate dehydrogenase; one or more enzymes selected from the group consisting of cytochrome terminal oxidase and succinate dehydrogenase and one or more enzymes selected from the group consisting of 6-phosphogluconate dehydrogenase and glutamate dehydrogenase; or lactate dehydrogenase, one or more enzymes selected from the group consisting of cytochrome terminal oxidase and succinate dehydrogenase, and one or more enzymes selected from the group consisting of 6-phosphogluconate dehydrogenase and glutamate dehydrogenase.

In some versions, the one or more enzymes in the first set are selected from pyruvate dehydrogenase.

In some versions, the one or more enzymes in the second set are selected from the group consisting of phosphate acetyltransferase and pyruvate oxidase.

In some versions, the enzymes in the third set comprise lactate dehydrogenase and cytochrome terminal oxidase, lactate dehydrogenase and one or more enzymes selected from the group consisting of 6-phosphogluconate dehydrogenase and glutamate dehydrogenase, or succinate dehydrogenase and 6-phosphogluconate dehydrogenase.

In some versions, the one or more enzymes in the first set are selected from pyruvate dehydrogenase, the one or more enzymes in the second set are selected from phosphate acetyltransferase, and the enzymes in the third set comprise lactate dehydrogenase and one or more enzymes selected from the group consisting of cytochrome terminal oxidase and succinate dehydrogenase, or lactate dehydrogenase and one or more enzymes selected from the group consisting of 6-phosphogluconate dehydrogenase and glutamate dehydrogenase.

In some versions, the one or more enzymes in the first set are selected from pyruvate dehydrogenase, the one or more enzymes in the second set are selected from phosphate acetyltransferase, and the enzymes in the third set comprise lactate dehydrogenase and cytochrome terminal oxidase, or lactate dehydrogenase and one or more enzymes selected from the group consisting of 6-phosphogluconate dehydrogenase and glutamate dehydrogenase.

In some versions, the one or more enzymes in the first set are selected from pyruvate dehydrogenase, the one or more enzymes in the second set are selected from pyruvate oxidase, and the enzymes in the third set comprise one or more enzymes selected from the group consisting of cytochrome terminal oxidase and succinate dehydrogenase and one or more enzymes selected from the group consisting of 6-phosphogluconate dehydrogenase and glutamate dehydrogenase.

In some versions, the microorganism further comprises a modification that reduces or ablates activity of an enzyme selected from the group consisting of pyruvate formate lyase and pyruvate formate lyase activating enzyme.

In some versions, the microorganism further comprises a modification that enhances expression of pyruvate decarboxylase and alcohol dehydrogenase.

In some versions, the microorganism is a bacterium or a yeast.

In some versions, an evolved microorganism is produced by sequentially culturing any microorganism described above or elsewhere herein in media comprising decreasing concentrations of a compound such as acetate, ethanol, or another compound. The media each preferably comprise approximately a same amount of total consumable carbon.

In some versions, the microorganism is cultured in media comprising decreasing concentrations of acetate. The concentrations of acetate in the media may range from about 0.1 mg/L acetate to about 3 g/L acetate.

Another aspect of the invention is a method of producing a chemical. The method comprises culturing any microorganism described above or elsewhere herein. The chemical may be selected from the group consisting of pyruvate and ethanol. The culturing may comprise culturing the microorganism in a medium comprising a biomass hydrolysate.

The objects and advantages of the invention will appear more fully from the following detailed description of the preferred embodiment of the invention made in conjunction with the accompanying drawings.

BRIEF DESCRIPTION OF THE DRAWINGS

FIG. 2A: Strain designed as ΔaceE, ΔcyoA, ΔcydB, Δpta, ΔeutI, ΔidhA, and Δdld. FIG. 2B: Strain designed as ΔlpdA, Δgnd, ΔsdhA, ΔpoxB, ΔpflB, ΔpflD, ΔtdcE, and ΔpurU. FIG. 2C: Strain designed as ΔaceE, ΔgdhA, ΔpoxB, ΔldhA, Δdld, ΔatpE, ΔpflB, ΔpflD, and ΔtdcE. FIG. 2D: Strain designed as designed as ΔaceE, Δgnd, ΔpoxB, ΔldhA, Δdld, ΔatpE, ΔpflB, ΔpflD, and ΔtdcE.

DETAILED DESCRIPTION OF THE INVENTION

Figure 1:
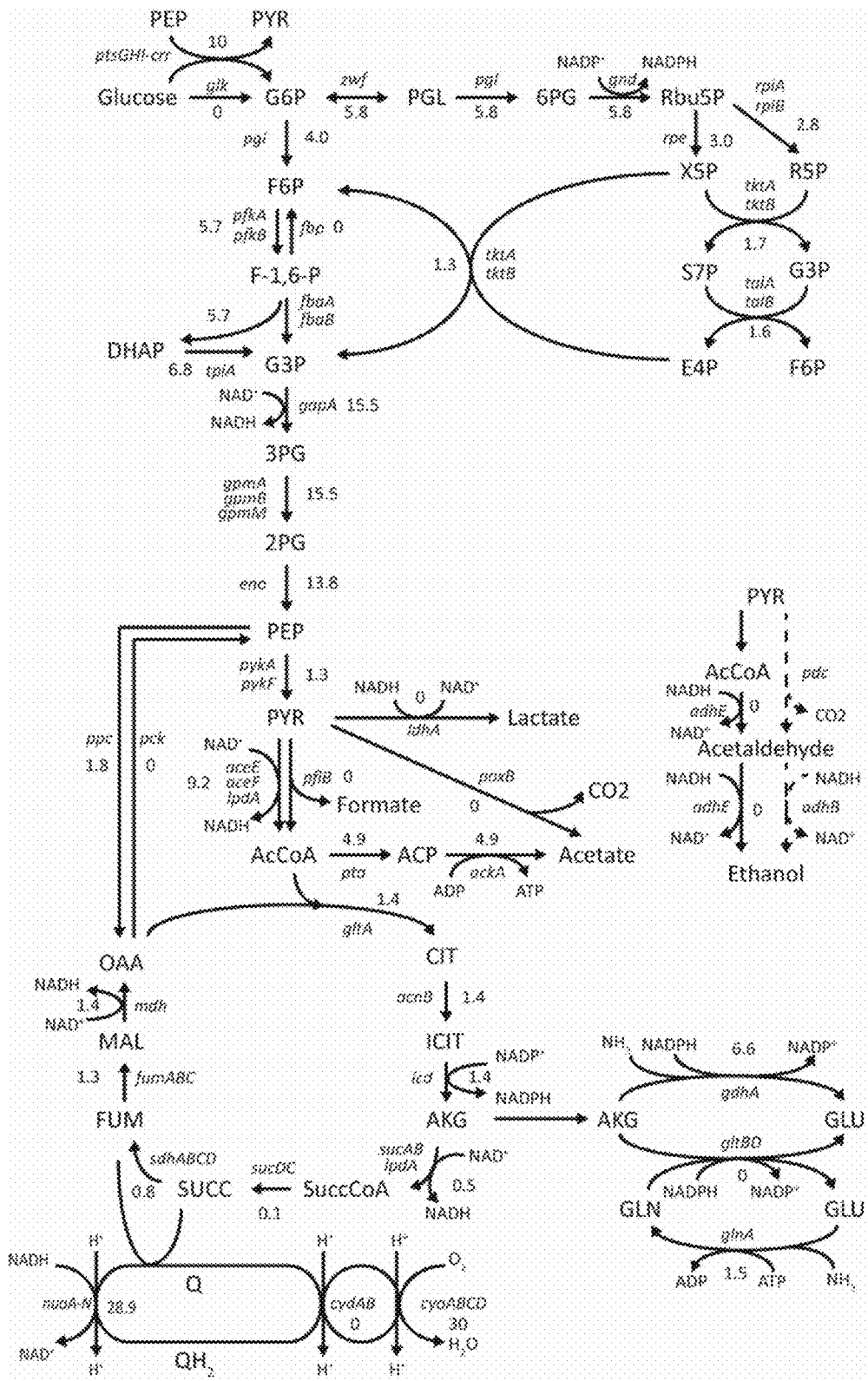
FIG. 1 is a schema showing the central metabolic pathway of wild-type *E. coli*. Genes associated with each reaction in the central metabolic network are shown and flux values are labeled. The metabolic flux distribution for the wild-type strain under aerobic conditions was predicted by flux balance analysis. Glucose uptake rate was set at 10 mmol/gDW/hour. The dashed line represents the ethanol synthesis pathway (PET operon) from *Zymomonas mobilis*.
Figure 2A:
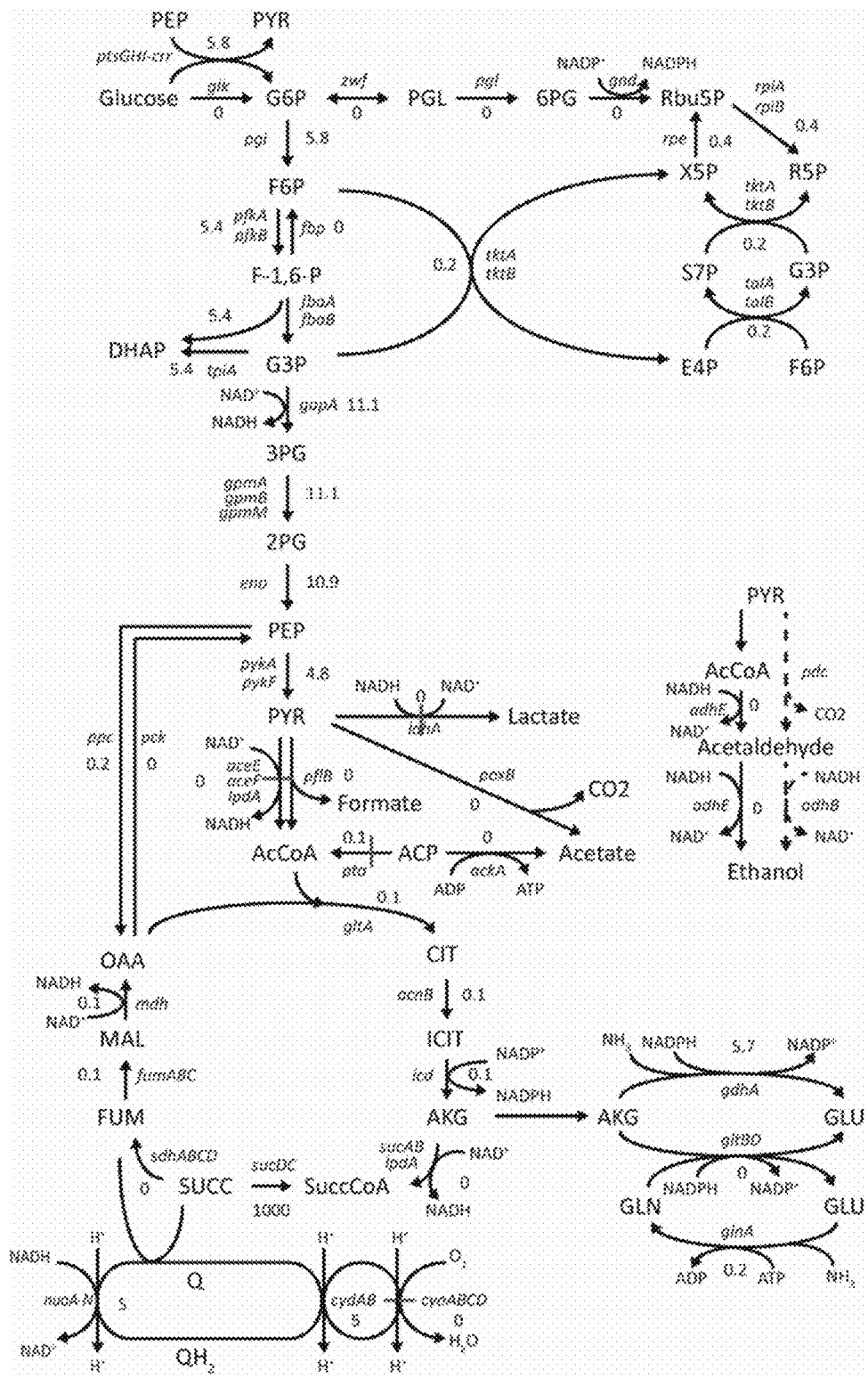
FIGS. 2A-2D are schemas showing the central metabolic pathway of mutant *E. coli* strains designed for pyruvate production. Genes associated with each reaction in the central metabolic network are shown and flux values are labeled. The reactions marked by bars correspond to the deletion targets calculated computationally. The labeled metabolic flux distribution for each strain was predicted by flux balance analysis. Glucose uptake rate was set at 10 mmol/gDW/hour. Oxygen uptake was unlimited for the strains shown in FIGS. 2B-2D, but limited to 3 mmol/gDW/hour for the strain shown in FIG. 2A.
Figure 2B:
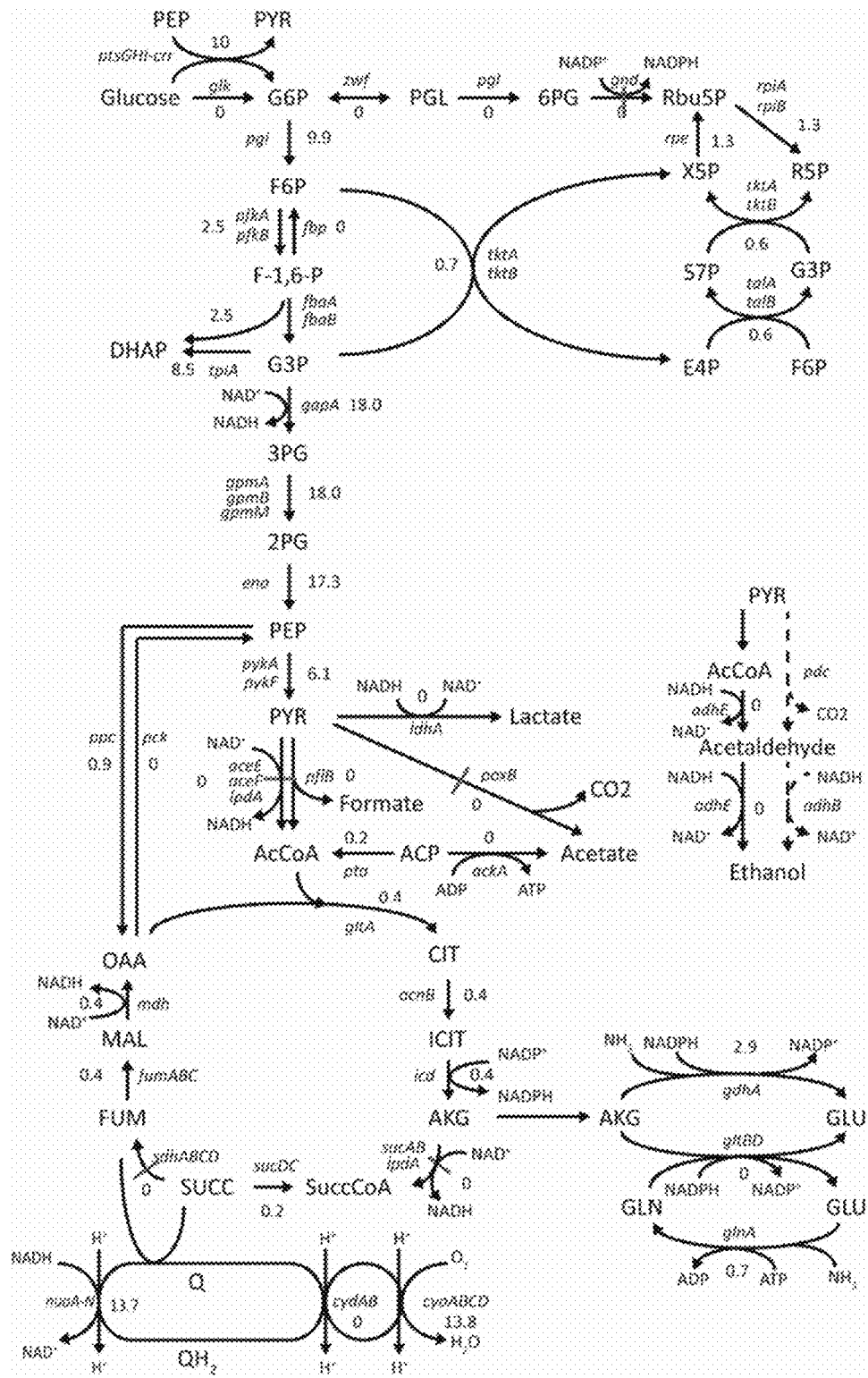
Figure 2C:
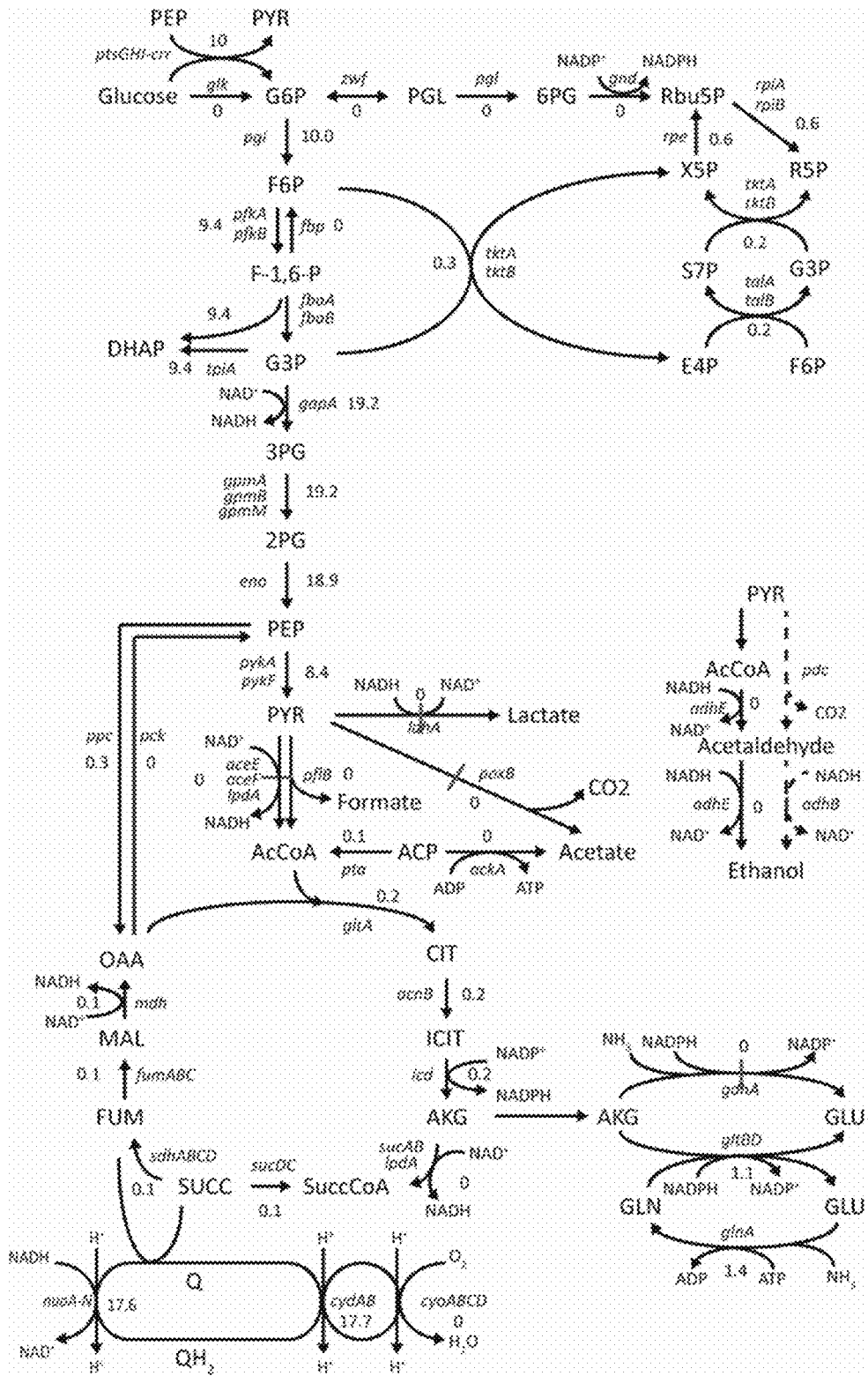
Figure 2D:
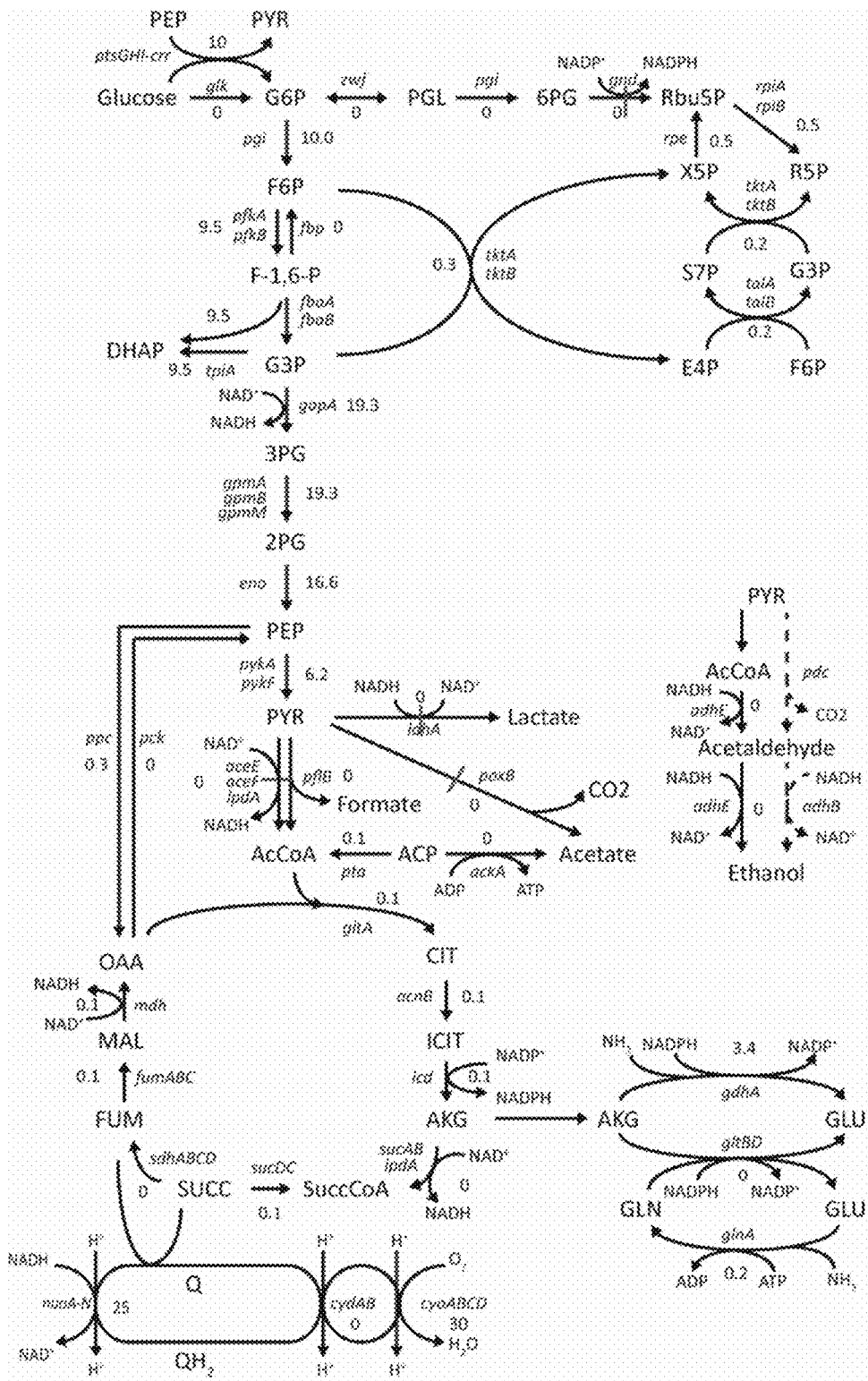

One aspect of the invention is directed to microorganisms comprising modifications that reduce or ablate the activity of gene products of one or more genes. Such a modification that that reduces or ablates the activity of gene products of one or more genes is referred to herein as a "functional deletion" of the gene product. "Gene product" refers to a protein or polypeptide encoded and produced by a particular gene. "Gene" refers to a nucleic acid sequence capable of producing a gene product and may include such genetic elements as a coding sequence together with any other genetic elements required for transcription and/or translation of the coding sequence. Such genetic elements may include a promoter, an enhancer, and/or a ribosome binding site (RBS), among others.

One of ordinary skill in the art will appreciate that there are many well-known ways to functionally delete a gene product. For example, functional deletion can be accomplished by introducing one or more genetic modifications. As used herein, "genetic modifications" refer to any differences in the nucleic acid composition of a cell, whether in the cell's native chromosome or in endogenous or exogenous non-chromosomal plasmids harbored within the cell. Examples of genetic modifications that may result in a functionally deleted gene product include but are not limited to mutations such as substitutions, partial or complete deletions, insertions, or other variations to a coding sequence or a sequence controlling the transcription or translation of a coding sequence; placing a coding sequence under the control of a less active promoter; blocking transcription of the gene with a trans-acting DNA binding protein such as a TAL effector or CRISPR guided Cas9; and expressing ribozymes or antisense sequences that target the mRNA of the gene of interest, etc. In some versions, a gene or coding sequence can be replaced with a selection marker or screenable marker. Various methods for introducing the genetic modifications described above are well known in the art and include homologous recombination, among other mechanisms. See, e.g., Green et al., *Molecular Cloning: A laboratory manual*, 4$^{th}$ ed., Cold Spring Harbor Laboratory Press (2012) and Sambrook et al., *Molecular Cloning: A Laboratory Manual*, 3$^{rd}$ ed., Cold Spring Harbor Laboratory Press (2001). Various other genetic modifications that functionally delete a gene product are described in the examples below. Functional deletion can also be accomplished by inhibiting the activity of the gene product, for example, by chemically inhibiting a gene product with a small molecule inhibitor, by expressing a protein that interferes with the activity of the gene product, or by other means.

In certain versions of the invention, the functionally deleted gene product may have less than about 95%, less than about 90%, less than about 85%, less than about 80%, less than about 75%, less than about 70%, less than about 65%, less than about 60%, less than about 55%, less than about 50%, less than about 45%, less than about 40%, less than about 35%, less than about 30%, less than about 25%, less than about 20%, less than about 15%, less than about 10%, less than about 5%, less than about 1%, or about 0% of the activity of the non-functionally deleted gene product.

In certain versions of the invention, a cell with a functionally deleted gene product may have less than about 95%, less than about 90%, less than about 85%, less than about 80%, less than about 75%, less than about 70%, less than about 65%, less than about 60%, less than about 55%, less than about 50%, less than about 45%, less than about 40%, less than about 35%, less than about 30%, less than about 25%, less than about 20%, less than about 15%, less than about 10%, less than about 5%, less than about 1%, or about 0% of the activity of the gene product compared to a cell with the non-functionally deleted gene product.

In certain versions of the invention, the functionally deleted gene product may be expressed at an amount less than about 95%, less than about 90%, less than about 85%, less than about 80%, less than about 75%, less than about 70%, less than about 65%, less than about 60%, less than about 55%, less than about 50%, less than about 45%, less than about 40%, less than about 35%, less than about 30%, less than about 25%, less than about 20%, less than about 15%, less than about 10%, less than about 5%, less than about 1%, or about 0% of the amount of the non-functionally deleted gene product.

In certain versions of the invention, the functionally deleted gene product may result from a genetic modification in which at least 1, at least 2, at least 3, at least 4, at least 5, at least 10, at least 20, at least 30, at least 40, at least 50, or more nonsynonymous substitutions are present in the gene or coding sequence of the gene product.

In certain versions of the invention, the functionally deleted gene product may result from a genetic modification in which at least 1, at least 2, at least 3, at least 4, at least 5, at least 10, at least 20, at least 30, at least 40, at least 50, or more bases are inserted in the gene or coding sequence of the gene product.

In certain versions of the invention, the functionally deleted gene product may result from a genetic modification in which at least about 1%, at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 85%, at least about 90%, at least about 95%, or about 100% of the gene product's gene or coding sequence is deleted or mutated.

In certain versions of the invention, the functionally deleted gene product may result from a genetic modification in which at least about 1%, at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 85%, at least about 90%, at least about 95%, or about 100% of a promoter driving expression of the gene product is deleted or mutated.

In certain versions of the invention, the functionally deleted gene product may result from a genetic modification in which at least about 1%, at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 85%, at least about 90%, at least about 95%, or about 100% of an enhancer controlling transcription of the gene product's gene is deleted or mutated.

In certain versions of the invention, the functionally deleted gene product may result from a genetic modification in which at least about 1%, at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 85%, at least about 90%, at least about 95%, or about 100% of a sequence controlling translation of gene product's mRNA is deleted or mutated.

In certain versions of the invention, the decreased activity or expression of the functionally deleted gene product is determined with respect to the activity or expression of the gene product in its unaltered state as found in nature. In certain versions of the invention, the decreased activity or expression of the functionally deleted gene product is determined with respect to the activity or expression of the gene product in its form in a corresponding microorganism. In certain versions, the genetic modifications giving rise to a functionally deleted gene product are determined with respect to the gene or coding sequence in its unaltered state as found in nature. In certain versions, the genetic modifications giving rise to a functionally deleted gene product are determined with respect to the gene or coding sequence in its form in a corresponding microorganism.

As used herein, "corresponding microorganism" refers to a microorganism of the same species having the same or substantially same genetic and proteomic composition as a microorganism of the invention, with the exception of genetic and proteomic differences resulting from the modifications described herein for the microorganisms of the invention.

Some versions of the invention comprise microorganisms configured for increased production of pyruvate. For the production of pyruvate, at least three sets of enzymes are functionally deleted in the microorganism. Enzymes in a first set are selected from the group consisting of pyruvate dehydrogenase and 2-oxoglutarate dehydrogenase. Enzymes in a second set are selected from the group consisting of phosphate acetyltransferase, acetate kinase, and pyruvate oxidase. Enzymes in a third set comprise lactate dehydrogenase and one or more enzymes selected from the group consisting of cytochrome terminal oxidase and succinate dehydrogenase; lactate dehydrogenase and one or more enzymes selected from the group consisting of 6-phosphogluconate dehydrogenase and glutamate dehydrogenase; one or more enzymes selected from the group consisting of cytochrome terminal oxidase and succinate dehydrogenase and one or more enzymes selected from the group consisting of 6-phosphogluconate dehydrogenase and glutamate dehydrogenase; or lactate dehydrogenase, one or more enzymes selected from the group consisting of cytochrome terminal oxidase and succinate dehydrogenase, and one or more enzymes selected from the group consisting of 6-phosphogluconate dehydrogenase and glutamate dehydrogenase. Deletion of any gene or any other modification that reduces or ablates the activity of these enzymes or reduces or ablates flux of metabolites through these enzymes is encompassed by the present invention.

Pyruvate dehydrogenases convert pyruvate into acetyl Co-A. Pyruvate dehydrogenases include enzymes classified under any or all of EC 1.2.4.1, EC 2.3.1.12, and EC 1.8.1.4. An exemplary pyruvate dehydrogenase is the pyruvate dehydrogenase of *E. coli*, which is a multi-subunit complex comprising AceE (SEQ ID NO:2) encoded by aceE (SEQ ID NO:1), AceF (SEQ ID NO:4) encoded by aceF (SEQ ID NO:3), and Lpd (SEQ ID NO:6) encoded by lpdA (SEQ ID NO:5). AceE has activity classified under EC 1.2.4.1. AceF has activity classified under 2.3.1.12. Lpd has activity classified under 1.8.1.4. Other pyruvate dehydrogenases include homologs of the *E. coli* pyruvate dehydrogenase.

2-Oxoglutarate dehydrogenases convert α-ketoglutarate, $NAD^+$, and CoA to succinyl CoA, $CO_2$, and NADH. 2-Oxoglutarate dehydrogenases include enzymes classified under any one or all of EC 1.8.1.4, EC 1.2.4.2, and EC 2.3.1.61. An exemplary 2-oxoglutarate dehydrogenase is the 2-oxoglutarate dehydrogenase of *E. coli*, which is a multi-subunit complex comprising Lpd (SEQ ID NO:6) encoded by lpdA (SEQ ID NO:5), SucA (SEQ ID NO:8) encoded by sucA (SEQ ID NO:7), and SucB (SEQ ID NO:10) encoded by sucB (SEQ ID NO:9). Lpd has activity classified under EC 1.8.1.4. SucA has activity classified under EC 1.2.4.2. SucB has activity classified under EC 2.3.1.61. Other 2-oxoglutarate dehydrogenases include homologs of the *E. coli* 2-oxoglutarate dehydrogenase. Functionally deleting 2-oxoglutarate dehydrogenase may be performed as an alternative to or in addition to functionally deleting pyruvate dehydrogenase.

Phosphate acetyltransferases convert acetyl-CoA and phosphate to CoA and acetyl phosphate. Phosphate acetyltransferases include enzymes classified under EC 2.3.1.8. An exemplary phosphate acetyltransferase is the phosphate acetyltransferase of *E. coli* (SEQ ID NO:12), which is encoded by pta (SEQ ID NO:11). Other phosphate acetyltransferases include homologs of the *E. coli* phosphate acetyltransferase.

Acetate kinases convert acetate and ATP to acetyl phosphate. Acetate kinases include enzymes classified under EC 2.7.2.-, such as EC 2.7.2.1. An exemplary acetate kinase is the acetate kinase A of *E. coli* (SEQ ID NO:14), which is encoded by ackA (SEQ ID NO:13). Other acetate kinases include homologs of the *E. coli* acetate kinase A. Functionally deleting acetate kinase may be performed as an alternative to or in addition to functionally deleting phosphate acetyltransferase. In some versions, the ackA gene in the microorganism is structurally and functionally intact such that the acetate kinase in the cells is fully expressed and fully functional.

Pyruvate oxidases convert pyruvate, phosphate, and $O_2$ to acetyl phosphate, $CO_2$, and $H_2O_2$. Pyruvate oxidases include enzymes classified under EC 1.2.3.3. An exemplary pyruvate oxidase is the pyruvate oxidase of *E. coli* (SEQ ID NO:16), which is encoded by poxB (SEQ ID NO:15). Other pyruvate oxidases include homologs of the *E. coli* pyruvate oxidase.

Lactate dehydrogenases convert pyruvate to lactate and vice versa. Lactate dehydrogenases include enzymes classified under any or all of EC 1.1.1.27 and EC 1.1.1.28. An exemplary lactate dehydrogenase is the LdhA of *E. coli* (SEQ ID NO:18), which is encoded by ldhA (SEQ ID NO:17). Other lactate dehydrogenases include homologs of the *E. coli* LdhA.

Cytochrome oxidases transfer electrons in the respiratory chain from donors to an acceptor. Cytochrome oxidases include enzymes classified under any or all of EC 1.9.3.1 and EC 1.10.3.-. Exemplary cytochrome oxidases suitable for functionally deleting in the present invention include cytochrome terminal oxidases, such as Family A cytochrome terminal oxidases. An exemplary Family A cytochrome terminal oxidase in *E. coli* is the cytochrome bo terminal oxidase, which is a multi-subunit complex comprising subunit I (SEQ ID NO:22) encoded by cyoB (SEQ ID NO:21), subunit II (SEQ ID NO:20) encoded by cyoA (SEQ ID NO:19), subunit III (SEQ ID NO:24) encoded by cyoC (SEQ ID NO:23), and subunit IV (SEQ ID NO:26) encoded by cyoD (SEQ ID NO:25). Subunits I-IV have activity classified under EC 1.10.3.-. A fifth gene of the cyo operon, cyoE (SEQ ID NO:27), encodes a heme O synthase (SEQ ID NO:28) that is essential for correct assembly of the complex and can be functionally deleted to effectively functionally delete the cytochrome bo terminal oxidase itself. Other cytochrome oxidases include homologs of the *E. coli* cytochrome bo terminal oxidase.

Succinate dehydrogenases catalyze the oxidation of succinate to fumarate with the reduction of ubiquinone to ubiquinol. Succinate dehydrogenases include enzymes classified under EC 1.3.5.1. An exemplary succinate dehydrogenase is the succinate dehydrogenase of *E. coli*, which is a multi-subunit complex comprising SdhA (SEQ ID NO:30) encoded by sdhA (SEQ ID NO:29), SdhB (SEQ ID NO:32) encoded by sdhB (SEQ ID NO:31), SdhC (SEQ ID NO:34) encoded by sdhC (SEQ ID NO:33), and SdhD (SEQ ID NO:36) encoded by sdhD (SEQ ID NO:35). Other succinate dehydrogenases include homologs of the *E. coli* succinate dehydrogenases.

6-Phosphogluconate dehydrogenases catalyze the decarboxylating reduction of 6-phosphogluconate into ribulose 5-phosphate in the presence of $NADP^+$. Phosphogluconate dehydrogenases include enzymes classified under EC 1.1.1.44. An exemplary 6-phosphogluconate dehydrogenase is the Gnd of *E. coli* (SEQ ID NO:38), which is encoded by gnd (SEQ ID NO:37). Other 6-phosphogluconate dehydrogenases include homologs of the *E. coli* Gnd.

Glutamate dehydrogenases convert glutamate to α-ketoglutarate and vice versa. Glutamate dehydrogenases include enzymes classified under EC 1.4.1.4. An exemplary glutamate dehydrogenase is the GdhA of *E. coli* (SEQ ID NO:40), which is encoded by gdhA (SEQ ID NO:39). Other glutamate dehydrogenases include homologs of the *E. coli* GdhA.

In some versions of the invention, the microorganisms having the above-referenced sets of enzymes functionally deleted are evolved for enhanced production of pyruvate. The microorganisms are evolved by sequentially culturing microorganisms in media comprising decreasing concentrations of acetate. This process preferably involves sequentially culturing the microorganisms in aliquots of media, with sequential aliquots comprising decreasing concentrations of acetate. The concentrations of acetate in the media are preferably within a range of from about 0 mg/L to about 80 g/L, such as from about 0.001 mg/L to about 80 g/L, about 0.01 mg/L to about 50 g/L, about 0.1 mg/L to about 10 g/L, or about 0.1 mg/L to about 3 g/L. In some versions, the starting acetate concentration in the medium is within a range of from about 90 mg/L to about 80 g/L and sequentially reduces to a concentration with a range of from about 0 mg/L to about 90 mg/L. In some versions, the starting acetate concentration in the medium is within a range of from about 90 mg/L to about 80 g/L and sequentially reduces to a concentration with a range of from about 0.001 mg/L to about 90 mg/L. In some versions, the starting acetate concentration in the medium is within a range of from about 90 mg/L to about 1 g/L and sequentially reduces to a concentration with a range of from about 0.1 mg/L to about 90 mg/L. In some versions, the starting acetate concentration in the medium is within a range of from about 90 mg/L to about 500 g/L and sequentially reduces to a concentration with a range of from about 1 mg/L to about 90 mg/L.

The initial amount of total consumable carbon in the various media used in the sequential culturing is preferably approximately the same among the media. The initial amount of total consumable carbon preferably ranges from about 1 g/L to about 100 g/L, but may be higher or lower. Beyond the acetate, the balance of consumable carbon preferably comprises a sugar such as glucose or other carbohydrates or carbon sources known in the art. The sequential culturing may comprise passing the microorganism through the media in at least about 2, 3, 4, 5, 7, 10, 15, or 20 passages and/or up to about 5, 10, 15, 20, 30, 50 or more passages.

Some versions of the invention comprise microorganisms configured for increased production of ethanol. These microorganisms have the enzymes described above for producing pyruvate functionally deleted but additionally have pyruvate formate lyase functionally deleted.

Pyruvate formate lyases catalyze the reversible conversion of pyruvate and coenzyme-A into formate and acetyl-CoA. Pyruvate formate lyases include enzymes classified under EC 2.3.1.54. An exemplary pyruvate formate lyase is the PFL of *E. coli* (SEQ ID NO:42), which is encoded by pflB (SEQ ID NO:41). Other pyruvate formate lyases include homologs of the *E. coli* PFL.

In some versions of the invention, a pyruvate formate lyase activating enzyme in the recombinant microorganism is functionally deleted. Pyruvate formate lyase activating enzymes include enzymes classified under EC 1.97.1.4. Pyruvate formate lyase activating enzymes activate pyruvate formate lyases. Functionally deleting a pyruvate formate lyase activating enzyme constitutes a way to functionally delete a pyruvate formate lyase. An exemplary pyruvate formate lyase activating enzyme is the PFL activase of *E. coli* (SEQ ID NO:44), which is encoded by pflA (SEQ ID NO:43). Other pyruvate formate lyase activating enzymes include homologs of the *E. coli* PFL activase.

The enzymes described herein can be functionally deleted by mutating or disrupting expression of any one or all of the genes encoding the enzyme or its substituent subunits. Accordingly, the pyruvate dehydrogenase can be functionally deleted by mutating or disrupting expression of any one or more of aceE, aceF, and lpdA or homologs thereof. The 2-oxoglutarate dehydrogenase can be functionally deleted by mutating or disrupting expression of any one or more of lpdA, sucA, and sucB or homologs thereof. The phosphate acetyltransferase can be functionally deleted by mutating or disrupting expression of pta or homologs thereof. The acetate kinase can be functionally deleted by mutating or disrupting expression of ackA or homologs thereof. The pyruvate oxidase can be functionally deleted by mutating or disrupting expression of poxB or homologs thereof. The lactate dehydrogenase can be functionally deleted by mutating or disrupting expression of ldhA or homologs thereof. The cytochrome oxidase can be functionally deleted by mutating or disrupting expression of any one or more of cyoA, cyoB, cyoC, cyoD and cyoE or homologs thereof. The succinate dehydrogenase can be functionally deleted by mutating or disrupting expression of any one or more of sdhA, sdhB, sdhC, and sdhD or homologs thereof. The 6-phosphogluconate dehydrogenase can be functionally deleted by mutating or disrupting expression of gnd or homologs thereof. The glutamate dehydrogenase can be functionally deleted by mutating or disrupting expression of gdhA or homologs thereof. The pyruvate formate lyase can be functionally deleted by mutating or disrupting expression of pflB and pflA or homologs thereof.

The microorganisms of the invention may also be modified to increase expression of one or more enzymes. Modifying the microorganism to increase expression of an enzyme can be performed using any methods currently known in the art or discovered in the future. Examples include genetically modifying the microorganism and culturing the microorganism in the presence of factors that increase expression of the enzyme. Suitable methods for genetic modification include but are not limited to placing the coding sequence under the control of a more active promoter, increasing the copy number of the gene, introducing a translational enhancer on the gene (see, e.g., Olins et al. *Journal of Biological Chemistry*, 1989, 264(29):16973-16976), and/or increasing expression of transactivators. Increasing the copy number of the gene can be performed by introducing additional copies of the gene to the microorganism, i.e., by incorporating one or more exogenous copies of the native gene or a heterologous homolog thereof into the microbial genome, by introducing such copies to the microorganism on a plasmid or other vector, or by other means. "Exogenous" used in reference to a genetic element means the genetic element is introduced to a microorganism by genetic modification. "Heterologous" used in reference to a genetic element means that the genetic element is derived from a different species. A promoter that controls a particular coding sequence is herein described as being "operationally connected" to the coding sequence.

The microorganisms of the invention may include at least one recombinant nucleic acid configured to express or overexpress a particular enzyme. "Recombinant" as used herein with reference to a nucleic acid molecule or polypeptide is one that has a sequence that is not naturally occurring, has a sequence that is made by an artificial combination of two otherwise separated segments of sequence, or both. This artificial combination can be achieved, for example, by chemical synthesis or by the artificial manipulation of isolated segments of nucleic acid molecules or polypeptides, such as genetic engineering techniques. "Recombinant" is also used to describe nucleic acid molecules that have been artificially modified but contain the same regulatory sequences and coding regions that are found in the organism from which the nucleic acid was isolated. A recombinant cell or microorganism is one that contains a recombinant nucleic acid molecule or polypeptide. "Overexpress" as used herein means that a particular gene product is produced at a higher level in one cell, such as a recombinant cell, than in a corresponding cell. For example, a microorganism that includes a recombinant nucleic acid configured to overexpress an enzyme produces the enzyme at a greater amount than a microorganism that does not include the recombinant nucleic acid.

Exogenous, heterologous nucleic acids encoding enzymes to be expressed in the microorganism are preferably codon-optimized for the particular microorganism in which they are introduced. Codon optimization can be performed for any nucleic acid by a number of programs, including "GENEGPS"-brand expression optimization algorithm by DNA 2.0 (Menlo Park, Calif.), "GENEOPTIMIZER"-brand gene optimization software by Life Technologies (Grand Island, N.Y.), and "OPTIMUMGENE"-brand gene design system by GenScript (Piscataway, N.J.). Other codon optimization programs or services are well known and commercially available.

Microorganisms of the invention configured to increase production of ethanol may be modified to increase expression of pyruvate decarboxylase and alcohol dehydrogenase.

Pyruvate decarboxylases catalyze the decarboxylation of pyruvic acid to acetaldehyde and carbon dioxide. Pyruvate decarboxylases include enzymes classified under EC 4.1.1.1. An exemplary pyruvate decarboxylase is the PDC of Zymomonas mobilis (SEQ ID NO:46), which is encoded by pdc (SEQ ID NO:45). Other pyruvate decarboxylases include homologs of the Z. mobilis PDC.

Alcohol dehydrogenases catalyze the interconversion between alcohols and aldehydes or ketones with the reduction of nicotinamide adenine dinucleotide ($NAD^+$ to NADH). Alcohol dehydrogenases include enzymes classified under EC 1.1.1.1. An exemplary alcohol dehydrogenase is the ADH2 of Zymomonas mobilis (SEQ ID NO:48), which is encoded by adhB (SEQ ID NO:47). Other alcohol dehydrogenases include homologs of the Z. mobilis ADH2.

Increased expression of the pyruvate decarboxylase and/or the alcohol dehydrogenase can be included in a microorganism comprising a functional deletion of any of the genes or gene products, or combinations thereof, described herein.

Isocitrate lyase, encoded by aceA in E. coli or homologs thereof, can also be functionally deleted in any of the microorganisms described herein.

Homologs include genes or gene products (including enzymes) that are derived, naturally or artificially, from a common ancestral gene or gene product. Homology is generally inferred from sequence similarity between two or more genes or gene products. Homology between genes may be inferred from sequence similarity between the products of the genes. The precise percentage of similarity between sequences that is useful in establishing homology varies with the gene or gene product at issue, but as little as 25% sequence similarity (e.g., identity) over 50, 100, 150 or more residues (nucleotides or amino acids) is routinely used to establish homology (e.g., over the full length of the two sequences to be compared). Higher levels of sequence similarity (e.g., identity), e.g., 30%, 35% 40%, 45% 50%, 55%, 60%, 65%, 70%, 75%, 80%, 85%, 90%, 95%, or 99% or more, can also be used to establish homology. Accordingly, homologs of the coding sequences, genes, or gene products described herein include coding sequences, genes, or gene products, respectively, having at least about 30%, 35%, 40%, 45%, 50%, 55%, 60%, 65%, 70%, 75%, 80%, 85%, 90%, 95%, or 99% identity to the coding sequences, genes, or gene products, respectively, described herein. In some versions, homologs of the genes described herein include genes that have gene products at least about 30%, 35%, 40%, 45%, 50%, 55%, 60%, 65%, 70%, 75%, 80%, 85%, 90%, 95%, or 99% identical to the gene products of the genes described herein. Methods for determining sequence similarity percentages (e.g., BLASTP and BLASTN using default parameters) are described herein and are generally available. The homologous gene products should demonstrate comparable activities and, if an enzyme, participate in the same or analogous pathways. "Orthologs" are genes or coding sequences thereof in different species that evolved from a common ancestral gene by speciation. Normally, orthologs retain the same or similar function in the course of evolution. As used herein "orthologs" are included in the term "homologs." Homologs also include paralogs.

For sequence comparison and homology determination, one sequence typically acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence based on the designated program parameters. A typical reference sequence of the invention is a nucleic acid or amino acid sequence corresponding to coding sequences, genes, or gene products described herein.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see Current Protocols in Molecular Biology, F. M. Ausubel et al., eds., Current Protocols, a joint venture between Greene Publishing Associates, Inc. and John Wiley & Sons, Inc., (supplemented through 2008)).

One example of an algorithm that is suitable for determining percent sequence identity and sequence similarity for purposes of defining homologs is the BLAST algorithm, which is described in Altschul et al., J. Mol. Biol. 215:403-410 (1990). Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff (1989) Proc. Natl. Acad. Sci. USA 89:10915).

In addition to calculating percent sequence identity, the BLAST algorithm also performs a statistical analysis of the similarity between two sequences (see, e.g., Karlin & Altschul, Proc. Natl. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001. The above-described techniques are useful in identifying homologous sequences for use in the methods described herein.

The terms "identical" or "percent identity", in the context of two or more nucleic acid or polypeptide sequences, refers to two or more sequences or subsequences that are the same or have a specified percentage of amino acid residues or nucleotides that are the same, when compared and aligned for maximum correspondence, as measured using one of the sequence comparison algorithms described above (or other algorithms available to persons of skill) or by visual inspection.

The phrase "substantially identical", in the context of two nucleic acids or polypeptides refers to two or more sequences or subsequences that have at least about 60%, about 65%, about 70%, about 75%, about 80%, about 85%, about 90, about 95%, about 98%, or about 99% or more nucleotide or amino acid residue identity, when compared and aligned for maximum correspondence, as measured using a sequence comparison algorithm or by visual inspection. Such "substantially identical" sequences are typically considered to be "homologous" without reference to actual ancestry. Preferably, the "substantial identity" exists over a region of the sequences that is at least about 50 residues in length, more preferably over a region of at least about 100 residues, and most preferably, the sequences are substantially identical over at least about 150 residues, at least about 250 residues, or over the full length of the two sequences to be compared.

Accordingly, homologs of the genes described herein include genes with gene products at least about 80%, 85%, 90%, 95%, 97%, 98%, 99%, or more identical to the gene products of the genes described herein.

The microorganisms of the invention may be prokaryotic, such as bacteria or archaea, or eukaryotic, such as yeast. Among bacteria, any bacterium in the domain Bacteria, the kingdom Eubacteria, the phylum Proteobacteria, the class Gammaproteobacteria, the order Enterobacteriales, and the family Enterobacteriaceae are suitable. Gram-positive, gram-negative, and ungrouped bacteria are suitable. Phototrophs, lithotrophs, and organotrophs are also suitable. In exemplary versions of the invention, the microorganism is *E. coli*. In some versions of the invention, the microorganism is a cyanobacterium. Suitable cyanobacteria include those from the genuses *Agmenellum, Anabaena, Aphanocapsa, Arthrosprira, Gloeocapsa, Haplosiphon, Mastigocladus, Nostoc, Oscillatoria, Prochlorococcus, Scytonema, Synechococcus*, and *Synechocystis*. Preferred cyanobacteria include those selected from the group consisting of *Synechococcus* spp., spp., *Synechocystis* spp., and *Nostoc* spp.

An aspect of the present invention includes methods of producing commodity chemicals, such as pyruvate and/or ethanol, with the microorganisms of the invention. The methods involve culturing the microorganism in conditions suitable for growth of the microorganism. Such conditions include providing suitable carbon sources for the particular microorganism along with suitable micronutrients. For eukaryotic microorganisms and heterotrophic bacteria, suitable carbon sources include various carbohydrates. Such carbohydrates may include biomass or other suitable carbon sources known in the art. For phototrophic bacteria, suitable carbon sources include $CO_2$, which is provided together with light energy. The commodity chemical can be purified or isolated with methods known in the art.

In some versions of the invention, the microorganism may be cultured in a medium comprising a biomass hydrolysate. The biomass hydrolysate can be produced from any biomass feedstock. Exemplary types of biomass feedstocks include sucrose-rich feedstocks such as suger cane; starchy materials, such as corn grain; and lignocellulosic biomass, such as costal Bermuda grass, corn cobs, corn stover, cotton seed hairs, grasses, hardwood stems, leaves, newspaper, nut shells, paper, primary wastewater solids, softwood stems, solid cattle manure, sorted refuse, swine waste, switchgrass, waste papers from chemical pulps, wheat straw, wood, and woody residues.

Prior to hydrolysis, the biomass feedstock may be pretreated or non-pretreated. Pretreatment of biomass feedstock removes a large proportion of the lignin and other materials and enhances the porosity of the biomass prior to hydrolysis. The biomass feedstock may be pretreated by any method. Exemplary pretreatments include chipping, grinding, milling, steam pretreatment, ammonia fiber expansion (AFEX, also referred to as ammonia fiber explosion), ammonia recycle percolation (ARP), $CO_2$ explosion, steam explosion, ozonolysis, wet oxidation, acid hydrolysis, dilute-acid hydrolysis, alkaline hydrolysis, organosolv, and pulsed electrical field treatment, among others. See, e.g., Kumar, P.; Barrett, D. M.; Delwiche, M. J.; Stroeve, P., Methods for Pretreatment of Lignocellulosic Biomass for Efficient Hydrolysis and Biofuel Production. *Industrial & Engineering Chemistry Research* 2009, 48, (8), 3713-3729.

The pretreated or non-pretreated biomass may be hydrolyzed by any suitable method. Hydrolysis converts biomass polymers to fermentable sugars, such as glucose and xylose, and other monomeric or oligomeric components. Exemplary hydrolysis methods include enzymatic hydrolysis (e.g., with cellulases or other enzymes) and acid hydrolysis (e.g., with sulfurous, sulfuric, hydrochloric, hydrofluoric, phosphoric, nitric, and/or formic acids), among other methods.

Exemplary biomass hydrolysates include AFEX-pretreated corn stover hydrolysate (ACSH) (Schwalbach et al. *Appl. Environ. Microbiol.* 2012, 78, (9), 3442-3457) and AFEX-pretreated switchgrass hydrolysate (ASGH).

The medium comprising the biomass hydrolysate may comprise at least about 5%, about 10%, about 20%, about 30%, about 40%, about 50%, about 60%, about 70%, about 80%, about 90%, about 95%, or about 99% biomass hydrolysate by volume or by mass.

The term "increase," whether used to refer to an increase in production of an organic acid, an increase in expression of an enzyme, etc., generally refers to an increase from a baseline amount, whether the baseline amount is a positive amount or none at all.

The elements and method steps described herein can be used in any combination whether explicitly described or not.

The singular forms "a," "an," and "the" include plural referents unless the content clearly dictates otherwise.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 5 to 6, from 1 to 9, from 3.6 to 4.6, from 3.5 to 9.9, and so forth.

All patents, patent publications, and peer-reviewed publications (i.e., "references") cited herein are expressly incorporated by reference to the same extent as if each individual reference were specifically and individually indicated as being incorporated by reference. In case of conflict between the present disclosure and the incorporated references, the present disclosure controls.

It is understood that the invention is not confined to the particular construction and arrangement of parts herein illustrated and described, but embraces such modified forms thereof as come within the scope of the following claims.

EXAMPLES

Overview

Microbes produce a variety of useful chemicals. However, most strains have not evolved to produce compounds at industrially-relevant levels. Metabolic engineering develops biocatalysts to produce desired chemicals at high rates, yields, and titers. Strains have been engineered to produce a broad range of products, including transportation fuels (e.g. ethanol, butanol and biodiesel) [1-5], pharmaceuticals (e.g. alkeloids, polyketides, nonribosomal peptides and isoprenoids) [6-11] and bulk and fine chemicals (e.g. amino acids, organic acids, industrial solvents and polymer precursors) [12-16]. Metabolic engineering strategies involve increasing production of pathway precursors, recycling redox carriers, improving flux through biosynthesis pathways, reducing toxic intermediate concentrations, and/or increasing tolerance to intermediates and products. Increasing precursor(s) supply is often needed to generate more of a desired downstream product. For example, strains with elevated malonyl-CoA levels were engineered to produce phloroglucinol (a polyketide derived from malonyl-CoA) [17], and strains with higher oxaloacetate levels produced more succinate, threonine and lysine, which are all derived from oxaloacetate[18].

Pyruvate is a central metabolite and precursor to acetyl-CoA and several amino acids (including alanine, lysine, valine, isoleucine and leucine). Commodity chemicals (e.g. ethanol, acetic acid, lactic acid and acrylic acid), as well as active pharmaceutical ingredients (e.g. polyketides and isoprenoids) can also be derived from pyruvate. Pyruvate can be converted into >60 commercial chemicals within five reaction steps. Furthermore, pyruvate itself can be used as a food additive, weight loss agent, and anti-aging skin treatment. Microbial production of pyruvate is an attractive alternative to current chemical processes, which are expensive and toxic [21].

*Escherichia coli, Corynebacterium glutamicum*, and *Saccharomyces cerevisiae* strains have been genetically engineered to produce pyruvate [19-24]. However, most strains have low yields and use expensive medium components. Previous *E. coli* metabolic engineering strategies focused on blocking pyruvate consumption pathways to phosphoenolpyruvate (PEP), acetyl-CoA, ethanol, acetate, lactate and formate. Other strategies prevented conversion of PEP to oxaloacetate by deleting PEP synthase, increasing glycolytic flux by deleting F1-ATPase deletion mutant or reducing NADH availability [19-21], and reducing TCA cycle fluxes by deleting α-ketoglutarate dehydrogenase [21]. The highest reported yield is 0.75 g pyruvate/g glucose (78% of the theoretical maximum yield) using a thiamin supplemented salts minimal medium. Pyruvate overproducing strains have been further altered to produce other chemicals, including alanine and diacetyl [25].

The present examples design and construct pyruvate strains using a genome-scale metabolic model of *E. coli*. OptORF [26] was used to search for gene deletions that would have high pyruvate yields at their maximal growth rate. Four mutant strains were constructed and characterized for growth and pyruvate production, and two of the four strains were adaptively evolved to increase growth rates and further improve pyruvate production. The pyruvate strains were further engineered to produce ethanol, which is derived from pyruvate. The examples show strains achieving up to 95% of the maximum theoretic yields for pyruvate. The examples also show growth and production of chemicals in bioreactors and with media containing biomass hydrolysate.

Materials and Methods

Strains and Plasmids

*E. coli* BW25113 and the pCP20 plasmid were obtained from the *E. coli* genetic stock center (CGSC, Yale University). Single *E. coli* gene deletion strains were obtained from the Keio collection (Open Biosystems) and used to construct multiple gene deletion strains (listed in Table 1). To generate mutants with multiple gene deletions, the kanamycin resistance gene (kan) was removed using the pCP20 plasmid [39]. An additional gene was deleted (and kan re-inserted) using P1 transduction from a donor Keio mutant and selection on LB agar plates with 50 µg/mL kanamycin. This process was repeated for each additional knockout and the gene deletions were verified by PCR. The GLBRCE1 strain, pJGG2 plasmid, and its corresponding empty vector (pBBR-DSC5) were obtained from Robert Landick (University of Wisconsin-Madison). The pJGG2 plasmid is a low copy number plasmid with a lac promoter that controls expression of the *Zymomonas mobilis* PET cassette genes (pdc and adhB) that encode enzymes to produce ethanol from pyruvate. GLBRCE1 lacks ldhA, pflB and ackA and contains pJGG2 and a chromosomal copy of the PET cassette inserted in the pflB locus [36].

Media and Culture Conditions

For shake flask and hungate tube experiments, M9 minimal media [44] supplemented with glucose and acetate (at varying concentrations) was used. Gentamicin was added to the media (at 15 µg/mL) for strains containing pJGG2 or pBBR-DSC5 plasmids. All strains were precultured overnight in Luria Broth (LB), pelleted and washed twice in M9 media, and then resuspended in M9 media with an initial OD600 of 0.01. For aerobic flask experiments, cultures were grown aerobically in 250 mL flasks containing 100 mL of media.

For anaerobic hungate tube experiments, cultures were grown in hungate culture tubes with 10 mL of media and IPTG was added (at 200 µM) to induce the expression of PET cassette. Hungate tubes were vacuumed and flushed with argon three times. All experiments were carried out in triplicate at 37° C. in a shaking incubator. Samples were periodically taken for further analysis and cells were removed using 0.2 µm nylon filter.

For aerobic bioreactor experiments, a minimal salts medium (adapted from [40]) was used that included 3.5 g/L $KH_2PO_4$, 5 g/L $K_2HPO_4$, 3.5 g/L $(NH_4)_2HPO_4$, 2 mM $MgSO_4$, 0.1 mM $CaCl_2$, 0.01 mM $FeCl_3$ and 0.5 mL per L trace metal solution (described previously [40]). Glucose (30 g/L) and acetate (at reported concentrations) were added to the minimal salts medium. AFEX-pretreated switchgrass hydrolysate (ASGH) was provided by the Great Lakes Bioenergy Research Center. The initial concentrations of glucose, xylose and acetate in ASGH hydrolysate were quantified by HPLC. Bioreactor seed cultures were prepared by inoculating 100 mL of minimal salts medium (with 30 g/L glucose and 0.9 g/L acetate) from a 5 mL overnight LB culture such that the initial OD600 was 0.01. Cells were grown at 37° C. for 14 hours in a 250-mL shake flask and then transferred into three 250-mL flasks containing 100 mL of same medium. The cultures were grown at 37° C. for another 8 hours and used to inoculate the bioreactors. The starting OD600 in the bioreactors was 0.05.

Bioreactors

Batch and fed-batch experiments were conducted in a 3 L bioreactor (Applikon Biotechonology, Inc., Shiedam, Netherlands) using a 1 L working volume with the following parameters 37° C., 0.5 L/min air inflow and pH 7.0±0.1. Acid (0.5 M $H_2SO_4$) and base (2 M KOH) buffers were added to adjust the pH as needed. The stifling speed was set to 500-800 rpm by a single Rushton impeller to ensure the dissolved oxygen level was above 40% of saturation. Each bioreactor experiment was conducted in duplicate. Samples were taken periodically for sugar and end-product analysis after cells were removed by centrifugation. For fed-batch experiments, a 200 g/L acetate solution was added to the reactor when growth slowed. For PYR020, the fed-batch started with 30 g/L glucose and 0.6 g/L acetate, and an additional 0.3 g/L acetate was added (1.5 mL of 200 g/L solution). For PYR004, the fed-batch started with 30 g/L glucose and 1.5 g/L acetate, and an additional 1.5 g/L acetate was added (7.5 mL of 200 g/L solution).

Chemical Analyses

Glucose concentrations were determined using an enzyme assay from Sigma (GAGO20). Pyruvate, lactate, acetate, succinate, and formate concentrations in the medium were measured by HPLC using an Aminex HPX-87H with Cation-H guard column (Bio-Rad, cat#125-0140). The mobile phase contained 0.02 N $H_2SO_4$ (for samples from minimal medium) or 0.05 N $H_2SO_4$ (for samples from ammonia fiber expansion (AFEX)-pretreated switchgrass hydrolysate (ASGH)) and was run at a flow rate of 0.5 mL/min at 50° C. The end-products were quantified (from standard curves) based on their refractive index. The reported yields were all adjusted by taking into account evaporation and buffer addition to bioreactors. The uptake and secretion rates were determined from the metabolite and biomass concentration data during exponential growth. Biomass concentrations (gram of cell dry weight per liter, gDW/L) were calculated from OD600 values using a conversion factor 1 OD600=0.415 gDW/L [41].

Adaptive Evolution

PYR001 and PYR002 were adaptively evolved independently for 20 passages. The initial cultures were grown in M9 minimal medium with 1.6 g/L glucose and 0.4 g/L acetate. At an OD600~0.2, cells were transferred to fresh medium (such that starting OD600 was 0.01). During adaptive evolution, the amount of acetate in the medium was gradually reduced, while the glucose concentration increased so that the total carbon source was 2 g/L. After 15 passages, the medium contained 1.98 g/L glucose and 0.02 g/L acetate. Cultures from each passage were frozen and stored at −80° C.

Strain Design

OptORF was used to identify gene deletions that couple growth and pyruvate production [26]. This method finds mutants that would produce pyruvate at their highest biomass yield. OptORF was run using a tilted inner objective function (growth rate—0.001•pyruvate production rate) [42] and a gene deletion penalty equal to 1 in the outer objective function. All simulations were done for glucose aerobic conditions using the iJR904 E. coli genome-scale metabolic network [43], with a maximum glucose uptake rate of 10 mmol/gDW/hour and an unlimited oxygen uptake.

Results

In Silico Strain Design for Pyruvate Production

To improve pyruvate production, OptORF suggested four strategies which delete: (1) aceE, cyoA, cydB, pta, eutI, ldhA and dld; (2) lpdA, gnd, sdhA, poxB, pflB, pflD, tdcE and purU; (3) aceE, gdhA, poxB, ldhA, dld, atpE, pflB, pflD and tdcE; or (4) aceE, gnd poxB, ldhA, dld, atpE, pflB, pflD and tdcE (FIGS. 2A-2D). Given the large numbers of deletions, the identified genes were further evaluated and prioritized for deletion. Enzymes that are inactive under glucose aerobic conditions (e.g. due to regulation) were first excluded, including pyruvate formate lyases (PflB and PflD) [27, 28]. In addition, eutI, dld and tdcE encode minor isozymes for Pta, LdhA and PflB, respectively [29-32]. Deleting purU also had little impact on cell growth in glucose minimal media [33, 34]. Based on these considerations, pflB, pflD, eutI, dld, tdcE and purU were not deleted since they are likely to have low (if any) activity anyway. Additionally, the cydB and atpE deletions were experimentally lethal in combination with other suggested gene deletions (data not shown) and were not included in the constructed strains. The remaining genes identified by OptORF were deleted to create four engineered strains (PYR001-PYR004, Table 1).

The engineered strains each involved deletions that impacted metabolism and pyruvate production differently. Deleting aceE, lpdA, pta, poxB, and/or ldhA reduces the conversion of pyruvate into acetyl-CoA, acetate, and lactate. Deletion of cyoA, sdhA, and/or lpdA slows down the citric acid (TCA) cycle which would decrease ATP production, and thus biomass yields. With regard to gdhA and gnd, E. coli has two primary pathways for glutamate synthesis using NADPH, ammonia and α-ketoglutarate. The glutamate dehydrogenase (GDH) pathway (via gdhA) does not require ATP, while the other glutamine synthetase-glutamine oxoglutarate aminotransferase (GS-GOGAT) pathway consumes one ATP per glutamate formed. Deleting gdhA forces cells to use the GS-GOGAT pathway, increasing ATP consumption and decreasing biomass yields. Similarly, deleting gnd prevents NADPH production via the pentose phosphate pathway, and cells produce NADPH from NADH via pyridine nucleotide transhydrogenase. The transhydrogenase consumes energy, thereby lowering the maximum biomass yield. In both cases, lowering the maximum biomass yield (via gdhA or gnd deletions) will increase pyruvate yields, since pyruvate and biomass formation compete for carbon. The gene deletions either prevent pyruvate consumption or reduce growth, and synergistically enhance pyruvate production. Based on the computational results, four strains (PYR001-PYR004) were constructed and tested experimentally (see Table 1). The aceA deletion in PYR001 is not required.

TABLE 1

Strains and plasmids.

| Strains/Plasmid | Genotype/Relevant characteristics | Reference |
|---|---|---|
| *E. coli* strains | | |
| BW25113 | lacI$^q$ rrnBT14 ΔlacZWJ16 hsdR514 ΔaraBADAH33 ΔrhaBADLD78 | [39] |
| PYR001 | BW25113 aceE::kan ΔcyoA Δpta ΔldhA ΔaceA | This study |
| PYR002 | BW25113 lpdA::kan Δgnd ΔpoxB ΔsdhA | This study |
| PYR003 | BW25113 aceE::kan ΔgdhA ΔpoxB ΔldhA | This study |
| PYR004 | BW25113 aceE::kan Δgnd ΔpoxB ΔldhA | This study |
| PYR010 | Adaptively evolved strain of PYR001 (single isolate) | This study |
| PYR020 | Adaptively evolved strain of PYR002 (single isolate) | This study |
| GLBRCE1 | MG1655 ΔackA ΔldhA ΔpflB::PET crl(70insIS1) ylbE(253insG) gltB(G3384A) yodD(A85T) glpR(150delG) gatC(916insCC), pJGG2 | [36] |
| EH010-pflB | PYR010 ΔaceE pflB::kan pJGG2 | This study |
| EH020-pflB | PYR020 ΔlpdA pflB::kan pJGG2 | This study |
| EH030-pflB | PYR003 ΔaceE pflB::kan pJGG2 | This study |
| EH040-pflB | PYR004 ΔaceE pflB::kan pJGG2 | This study |
| Plasmids | | |
| pBBR1-MSC5 | pBBR oriT; P$_{lac}$; Gent$^R$ | [36] |
| pJGG2 | pBBR1-MSC5 with adhB and pdc (PET cassette) from pLOI295; Gent$^R$ | [36] |

Abbreviations:
kan, kanamycin resistance gene;
Gent$^R$, gentamicin resistance.

Characterization of Engineered Pyruvate Strains

Figure 3A:
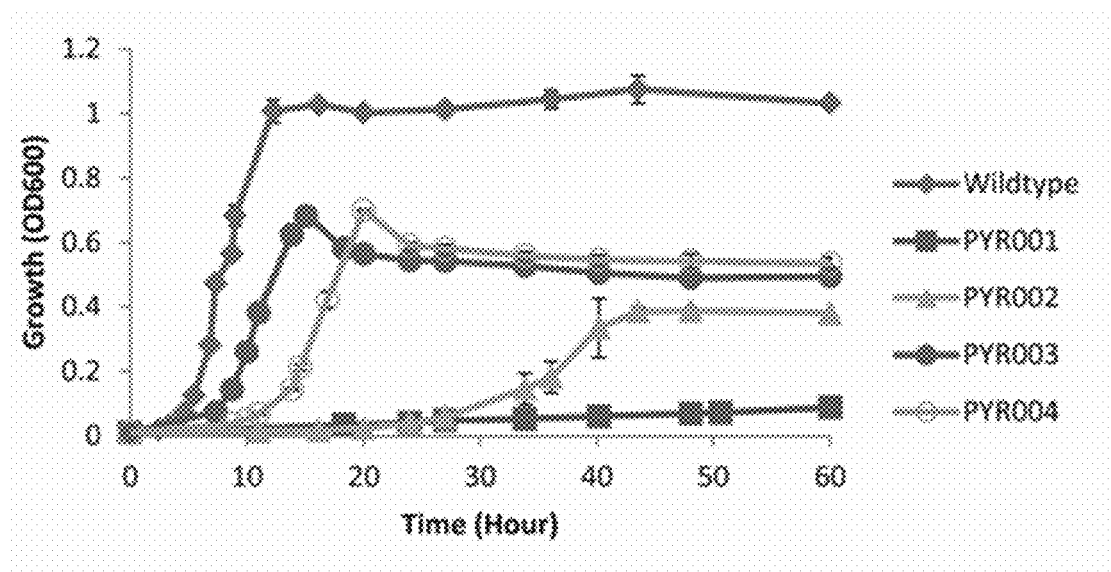
FIGS. 3A-3F show growth (FIGS. 3A and 3D), pyruvate production (FIGS. 3B and 3E), and glucose consumption (FIGS. 3C and 3F) of wild-type (BW25113) and mutant *E. coli* strains. Cells were grown in M9 minimal medium containing glucose and acetate. (See Table 2 for media details).
Figure 3B:
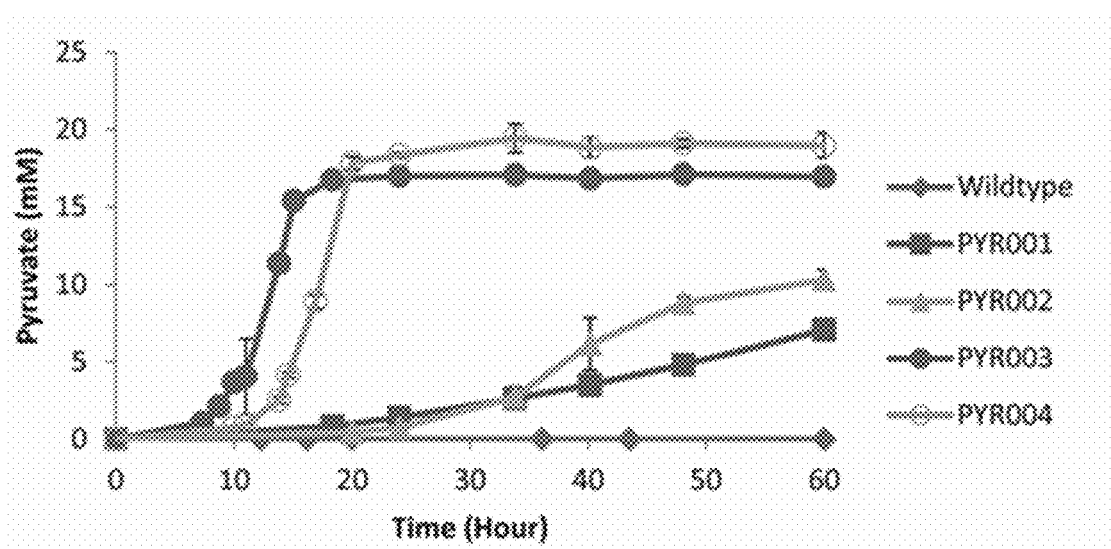
Figure 3C:
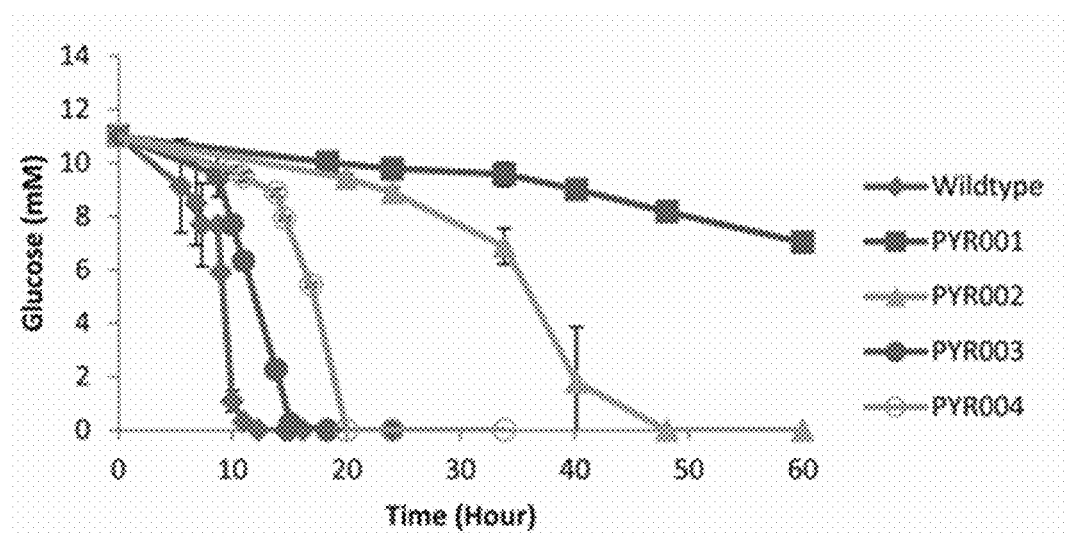

Pyruvate production was characterized in the parent *E. coli* (BW25113) and four mutant strains PYR001, PYR002, PYR003 and PYR004 in M9 minimal medium supplemented with glucose (FIGS. 3A-3C). All mutant strains contain either an aceE or lpdA deletion, which prevents synthesis of acetyl-CoA from pyruvate via pyruvate dehydrogenase. As a result, acetate was added to the media for all four mutant strains to allow for acetyl-CoA synthesis and growth (Table 2). The four mutants grew slower than the parent strain, but produced pyruvate as predicted by the model (FIGS. 3A-3C), whereas the parent strain did not secrete any pyruvate. Strain PYR001 grew the slowest and only consumed ~40% of glucose (~4.0 mM) within 60 hours. However, PYR001 converted most of the glucose consumed to pyruvate (79% of the theoretical maximum yield, Table 2). Strains PYR003 and PYR004 both completed growth within 20 hours and produced 17.0 and 19.4 mM pyruvate, respectively (79% and 87% of theoretical maximum yield). Among the four mutants, PYR002 had the lowest pyruvate yield (43%) and also exhibited a slower growth rate.

Figure 4:
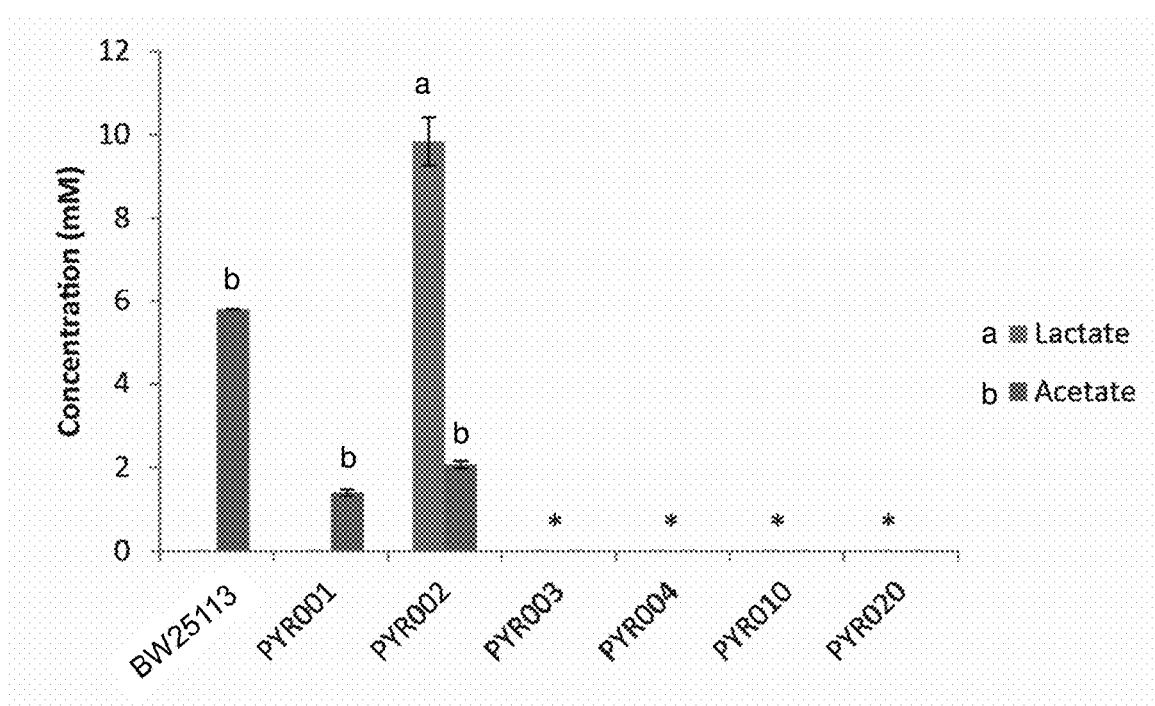
FIG. 4 shows (a) lactate and (b) acetate secretion for parent (BW25113) and mutant *E. coli* strains under aerobic conditions in shake flasks. The shown concentrations are the maximum acid concentrations observed over 60 hours during growth in M9 minimal medium supplemented with glucose and acetate. (See Table 2 for media details). Acetate accumulated in BW25113, PYR001 and PYR002 cultures and lactate accumulated in PYR002 cultures. * indicates concentrations of acetate and lactate that were below the detection level of the HPLC.

The secretion of metabolic by-products, such as succinate, formate, acetate, lactate and ethanol, was analyzed using HPLC (FIG. 4). Acetate was the main byproduct of the parent strain (BW25113). PYR001 and PYR002 each produced ~1 to 2 mM acetate (which was surprising since they required exogenous acetate for growth), while PYR003 and PYR004 consumed acetate, presumably for acetyl-CoA production. PYR002 was the only strain that produced lactate (~9.8 mM), which explains its relatively low pyruvate yield. Succinate, formate, and ethanol were below the limits of detection by HPLC.

TABLE 2

Production of pyruvate from the parent and mutant strains in shake flasks.

| | M9 Medium with | | Growth | Pyruvate Yield | | Pyruvate | Pyruvate Production Rate | |
|---|---|---|---|---|---|---|---|---|
| | Glucose | Acetate | Rate | % of max. theoretical | Conversion$^‡$ (g pyruvate/ | Titer | Volumetric | Specific$^¶$ (mmol/gDW/ |
| Strains | (g/L) | (g/L) | (hour$^{-1}$) | yield$^†$ | g substrate) | (g/L)$^§$ | (g/L/hour) | hour) |
| BW25113 | 2 | 0 | 0.59 ± 0.01 | 0 | 0 | 0 | 0 | 0 |
| PYR001 | 1.9 | 0.1 | 0.02 ± 0.00 | 79.15 ± 4.63 | 0.78 ± 0.05 | 0.62 ± 0.04 | 0.01 ± 0.00 | 6.04 ± 0.24 |
| PYR002 | 1.8 | 0.2* | 0.12 ± 0.01 | 43.24 ± 2.89 | 0.43 ± 0.03 | 0.91 ± 0.06 | 0.02 ± 0.00 | 5.47 ± 0.04 |
| PYR003 | 1.9 | 0.1 | 0.45 ± 0.03 | 79.05 ± 0.63 | 0.75 ± 0.00 | 1.50 ± 0.01 | 0.08 ± 0.00 | 20.36 ± 0.47 |
| PYR004 | 1.9 | 0.1 | 0.30 ± 0.00 | 86.60 ± 4.12 | 0.82 ± 0.04 | 1.71 ± 0.08 | 0.07 ± 0.01 | 19.11 ± 0.25 |
| PYR010 | 1.98 | 0.02 | 0.20 ± 0.04 | 68.33 ± 7.81 | 0.67 ± 0.08 | 1.39 ± 0.16 | 0.06 ± 0.00 | 14.91 ± 1.68 |
| PYR020 | 1.98 | 0.02 | 0.34 ± 0.00 | 95.23 ± 3.12 | 0.92 ± 0.03 | 1.95 ± 0.06 | 0.05 ± 0.00 | 23.73 ± 0.88 |

*PYR002 required more acetate than other strains to start growth within 48 hour.
$^†$Percent of theoretical yield is calculated as the pyruvate concentration divided by the theoretical maximum production of pyruvate (2 mmol of pyruvate per mmol of glucose). Acetate was also taken account for calculating the theoretical maximum production (0.5 mmol of pyruvate per mmol of acetate). The yield was adjusted by the culture volume loss due to the liquid evaporation in shake flasks under aerobic conditions.
$^‡$Conversion is expressed as the gram of pyruvate produced per gram of total carbon source (including glucose and acetate). It was adjusted by the culture volume loss due to the liquid evaporation in shake flasks under aerobic conditions.
$^§$The reported titer is the concentration determined by HPLC (and does not account for evaporative loss).
$^¶$The specific production rate is the pyruvate production rate per gram of cell dry weight (gDW) during exponential growth.
The numbers that follow the ± sign are standard deviations (SD) from triplicate experiments.

Adaptive Evolution to Improve Pyruvate Productivity

Figure 3D:
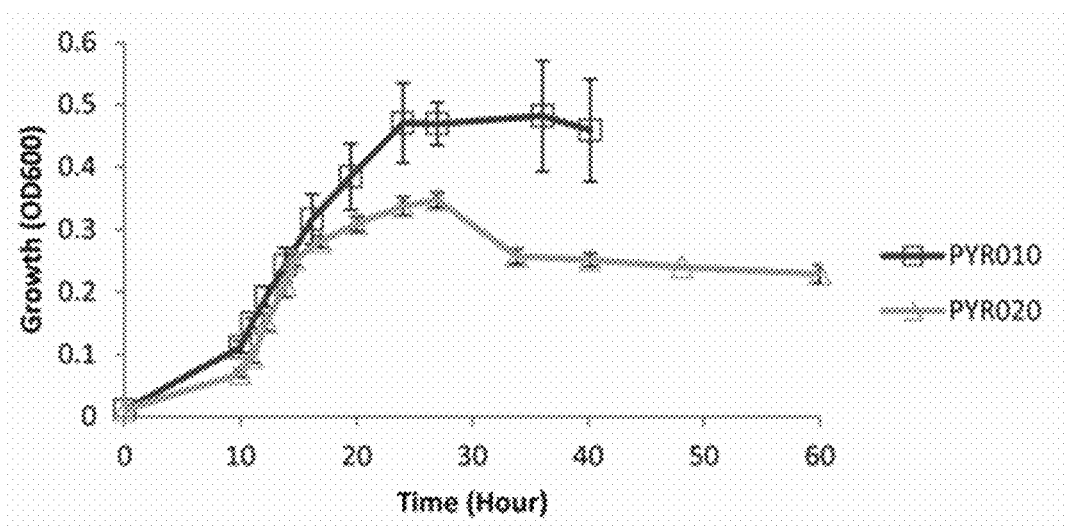
Figure 3E:
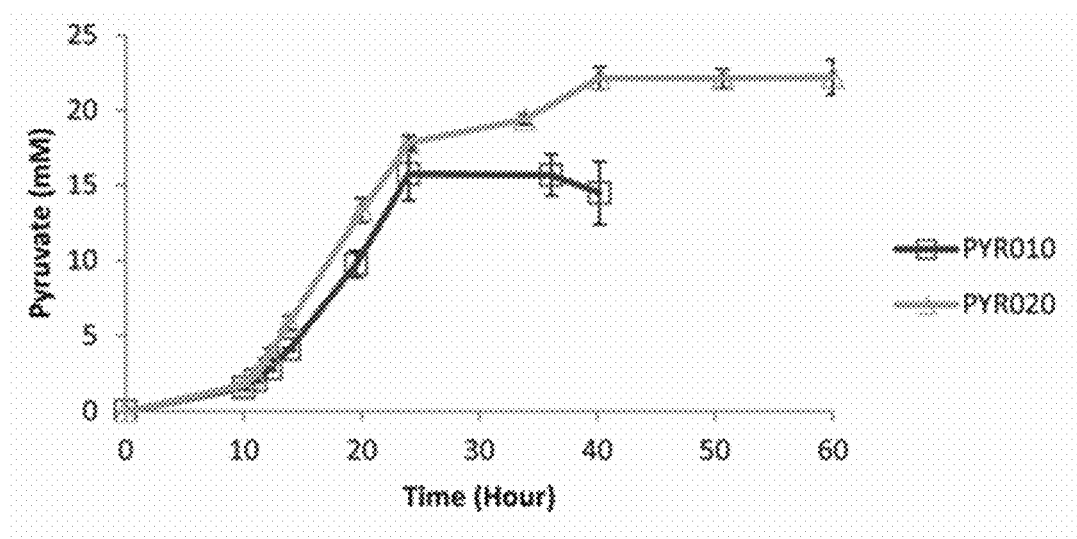
Figure 3F:
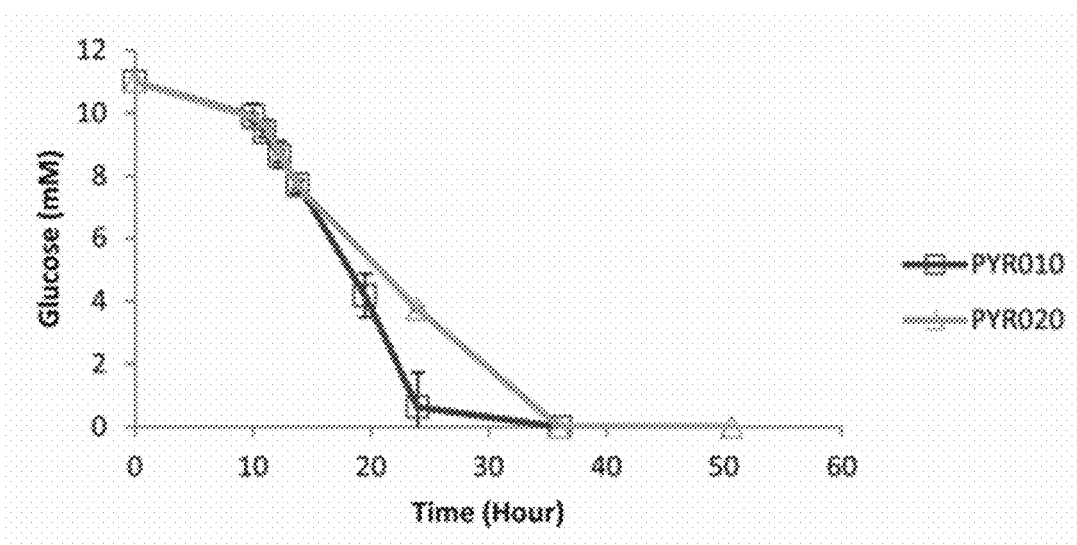

Strains PYR003 and PYR004 showed high pyruvate productivity, while strains PYR001 and PYR002 exhibited low pyruvate yields and/or production rates. All four pyruvate producing strains were designed such that at their maximum growth rate pyruvate production would be high. Therefore, an adaptive evolution approach was used to evolve PYR001 and PYR002 and select for faster growth, which should also select for higher pyruvate rates. Adaptive evolution was conducted under aerobic conditions for 20 passages at 37° C. in glucose+acetate M9 minimal medium. Acetate was added to the medium to enable cell growth, but the concentration was reduced over adaptive evolution (Table 2). Single colonies of the evolved populations, containing progenies of PYR001 and PYR002, were isolated from the last passage and are referred to as PYR010 and PYR020, respectively. The evolved isolates' growth and pyruvate production were characterized (Table 2 and FIGS. 3D-F). The evolved strains had a 10-fold (PYR010) and 3-fold (PYR020) increase in growth rate and ~2-fold increase in pyruvate titers (PYR010 and PYR020). In terms of pyruvate yield, PYR010 had a 10% lower yield than its unevolved strain (PYR001) while PYR020 had ~2-fold increase (PYR020). Interestingly, both evolved strains needed less acetate (5-fold and 10-fold decrease) in the medium to support their growth. Among the four unevolved strains and two evolved strains, PYR020 performed best with respect to yield and titer, followed by PYR004. Both strains were selected for further characterization in bioreactors (Table 3).

Culture in High Concentration of Carbon Source and Lignocellulosic Biomass

Strains with high yields, titers and volumetric production rates are desired for industrial application. While our engineered strains achieved high yields in shake flasks, their titers and volumetric production rate were low due to the low glucose concentrations in the medium. Therefore, a minimal salts medium with higher glucose concentrations (30 g/L) was used to evaluate production by two of the higher yielding pyruvate strains (PYR020 and PYR004). Acetate was the limiting nutrient for both mutants, and thus two different concentrations were used in different experiments (0.9 g/L and 1.5 g/L for PYR020, and 1.5 g/L and 3 g/L for PYR004). Experiments were conducted in 1 L volume, pH-controlled bioreactors, and the dissolved oxygen level was kept above 40% of saturation to maintain an aerobic environment.

Figure 5:
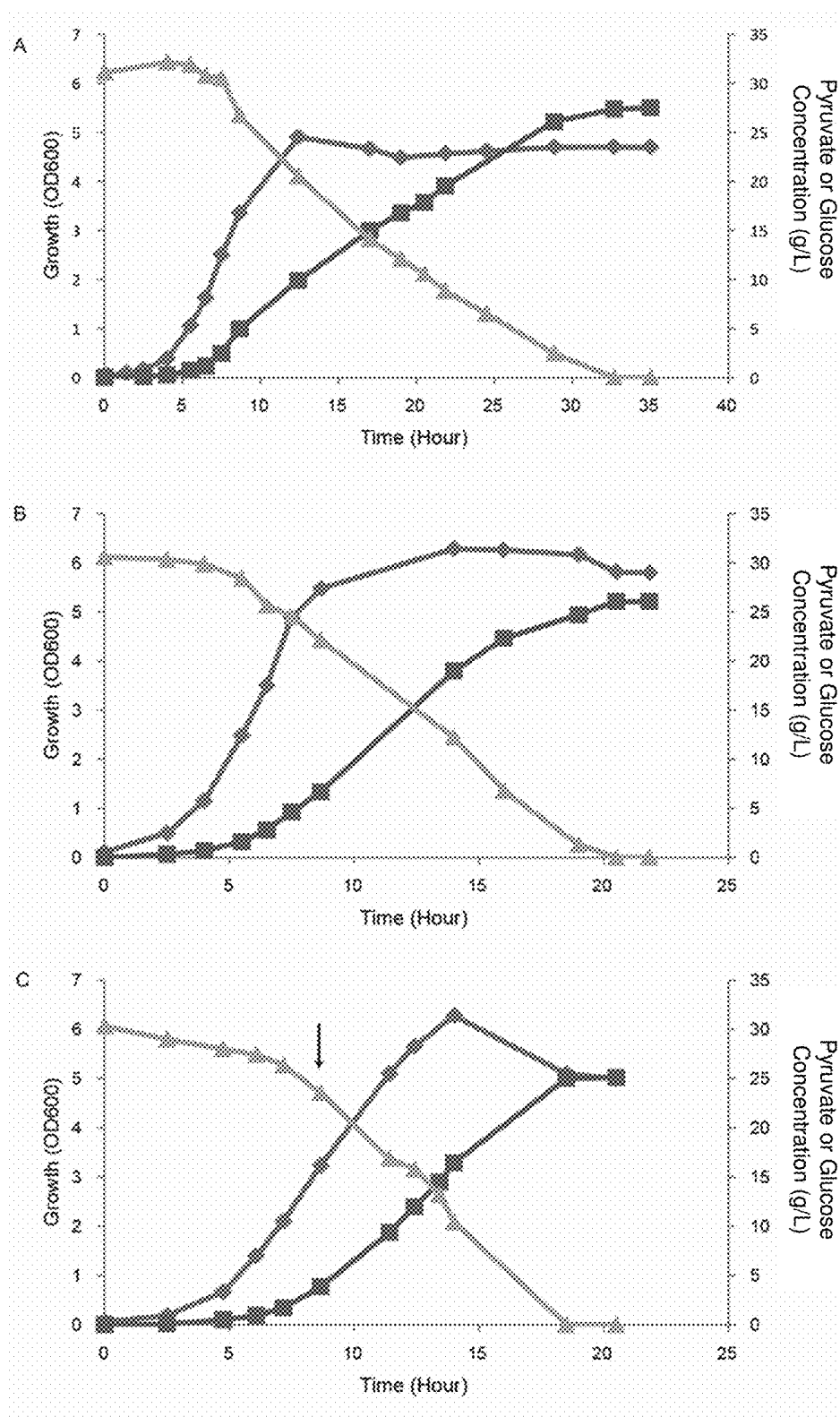
FIG. 5 shows growth, glucose consumption, and pyruvate production by PYR004 in bioreactors. Panels (A) and (B) show batch fermentation in minimal salts medium containing 30 g/L glucose with 1.5 g/L acetate (panel A) or 3 g/L acetate (panel B). Panel (C) shows fed-batch fermentation operated in minimal salts medium initially containing 30 g/L glucose and 1.5 g/L acetate. In the fed-batch operation, an additional 7.5 mL of 200 g/L acetate was added at 8.5 hours, indicated by the black arrow, for a total acetate concentration of 3.0 g/L. Experiments were performed in duplicate. Diamond: OD 600. Triangle: glucose concentration. Square: pyruvate concentration.
Figure 6:
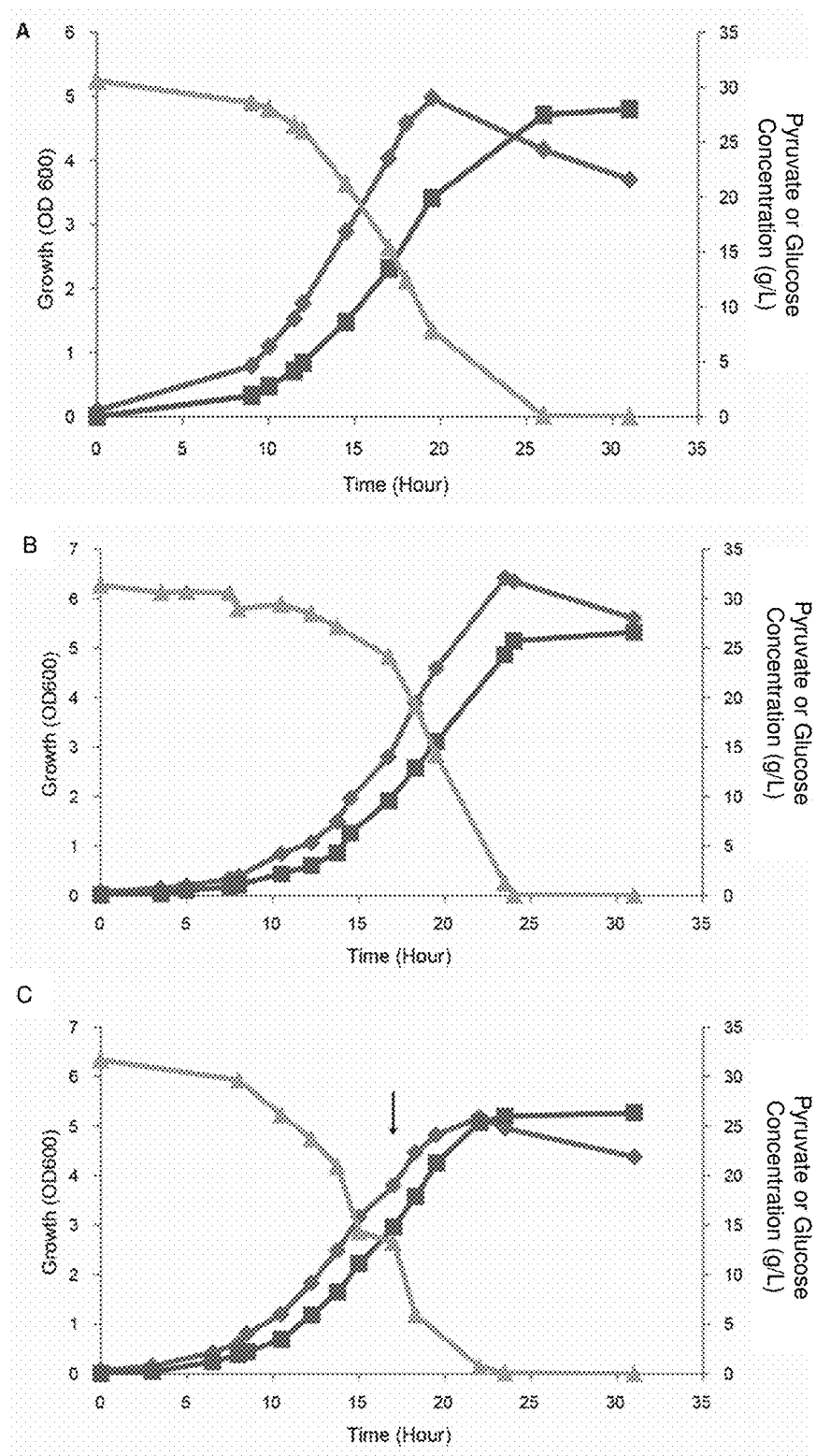
FIG. 6 shows growth, glucose consumption and pyruvate production by PYR020 in bioreactors. Panels (A) and (B) show batch fermentation in minimal salts medium containing 30 g/L glucose with 0.9 g/L acetate (Panel A) or 1.5 g/L acetate (Panel B). Panel (C) shows fed-batch fermentation operated in minimal salts medium initially containing 30 g/L glucose and 0.6 g/L acetate. In the fed-batch operation, an additional 1.5 mL of 200 g/L acetate was added at 17 hours, indicated by the black arrow. Experiments were performed in duplicate. Diamond: OD 600. Triangle: glucose concentration. Square: pyruvate concentration.

PYR020 and PYR004 were first grown in batch bioreactors in minimal salts media with 30 g/L glucose plus acetate. Both PYR004 and PYR020 had slightly higher growth rates, pyruvate yields and titers in media containing less acetate (1.5 g/L for PYR004 and 0.9 g/L for PYR020) (Table 3). For PYR004, higher acetate concentrations significantly reduced the time required to complete conversion of glucose to pyruvate (from ~33 hours to ~20 hours, FIG. 5). However, at the same acetate concentration (1.5 g/L) PYR020 was faster than PYR004 (FIG. 5, Panel (A), and FIG. 6, Panel (B)), presumably because PYR020 was evolved to grow at lower acetate concentrations. In batch conditions, both strains exhibited higher volumetric productivities when grown with higher acetate levels (Table 3). The two strains produce pyruvate at varying amounts during different stages of batch growth. PYR004 produced a large amount of pyruvate after growth stopped (~27% and ~63% of total pyruvate produced for 3 and 1.5 g/L acetate, respectively) (FIG. 5), while PYR020 produced most of the pyruvate during growth (~91% and 71% for 1.5 and 0.9 g/L acetate, respectively) (FIG. 6). In addition, PYR020 had ~33% higher specific pyruvate production rates (measured in mmol pyruvate/gDW/h) during exponential growth than PYR004 (Table 3).

Both strains were also grown in fed-batch bioreactors, where additional acetate was added once growth slowed. Compared to the batch results with the same total amount of acetate (0.9 g/L for PYR020 and 3 g/L for PYR004), both strains produced less pyruvate (~1.9 and ~2.2% lower yields for PYR020 and PYR004, respectively) in fed-batch experiments (Table 3, FIG. 5 and FIG. 6). However, both strains had higher volumetric pyruvate production rates when grown in fed-batch compared to batch growth with the same total amount of acetate. In both batch and fed-batch operation, tradeoffs appear to exist between volumetric productivities and pyruvate yields, with PYR004 tending to have higher volumetric productivities and PYR020 tending to have higher yields in the conditions tested (Table 3).

Figure 7:
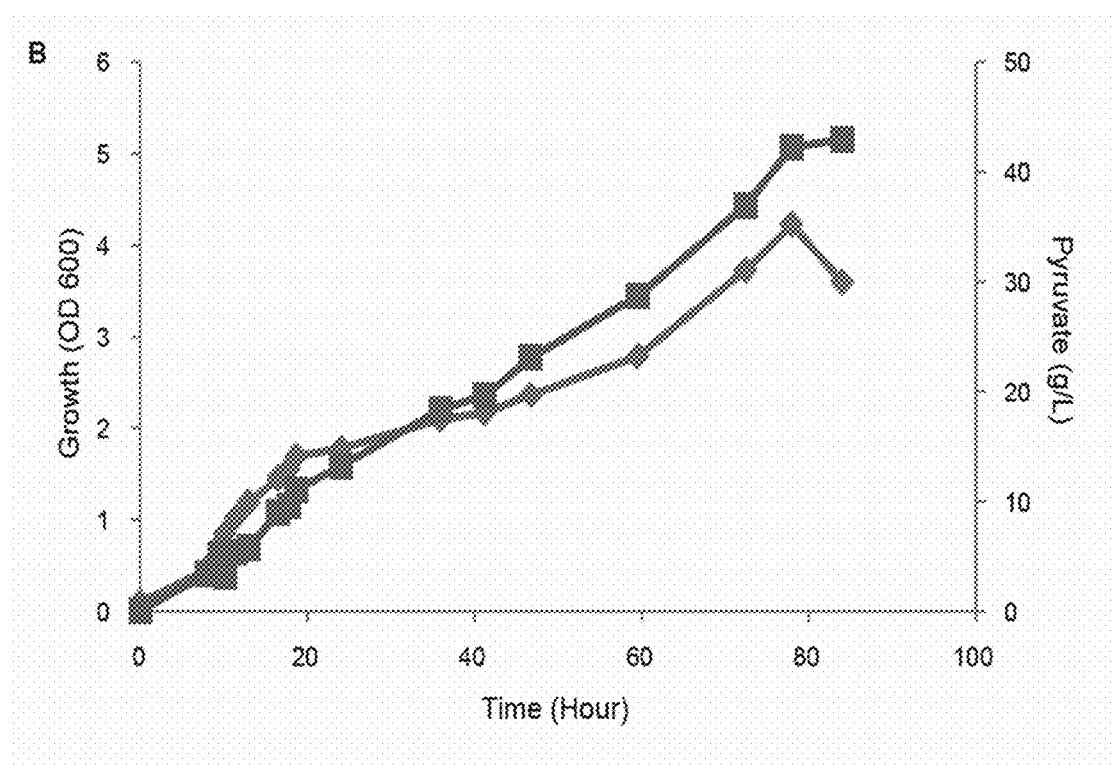
FIG. 7 shows batch production of pyruvate in ammonia fiber expansion (AFEX)-pretreated switchgrass hydrolysate (ASGH) by strain PYR020. Cells were grown in ASGH containing 48 g/L glucose, 27 g/L xylose, and 2.6 g/L acetate. Diamond: OD 600. Square: pyruvate concentration.

Since PYR020 had slightly higher pyruvate yields in minimal salts media than PYR004, PYR020 was further characterized in media derived from lignocellosic biomass. AFEX-pretreated switchgrass hydrolysate (ASGH) was used in batch bioreactor experiments, and contained 48 g/L glucose and 2.6 g/L acetate. The natural presence of acetate in ASGH (and other plant hydrolysates) meant no acetate supplementation was required. Compared to glucose minimal salts media, PYR020 had a similar exponential growth rate in ASGH (~0.22 hour$^{-1}$), but entered into a slower linear growth phase after ~20 hours (FIG. 7). Growth stopped at −80 hours, after all the glucose and most of the acetate (1.8 g/L) were utilized. However, xylose, another sugar present in ASGH, was hardly used. While pyruvate titers (40.7 g/L) and pyruvate yields (85.6%) were still high, the volumetric production rate was substantially lower in ASGH then minimal salts media due to slower growth (Table 3). Hydrolysates derived from lignocellulosic biomass contain microbial inhibitors (e.g., feruloyl amide) [35], whose presence reduces growth and xylose conversion. To further increase pyruvate production from lignocellulosic biomass, improvements in xylose conversion and inhibitor tolerance are likely needed.

TABLE 3

Production of pyruvate from the mutant strains in bioreactors.

| Strains | Bioreactor Mode | Medium# Glucose (g/L) | Medium# Acetate (g/L) | Growth Rate (hour$^{-1}$) | Pyruvate yield % of max. theoretical yield† | Pyruvate yield Conversion‡ (g pyruvate/ g substrate) | Pyruvate Titer (g/L)§ | Pyruvate Production Rate Volumetric (g/L/hour) | Pyruvate Production Rate Specific¶ (mmol/gDW/ hour) |
|---|---|---|---|---|---|---|---|---|---|
| PYR020 | Batch | 30 | 0.9 | 0.25 ± 0.02 | 92.35 ± 0.41 | 0.89 ± 0.01 | 27.38 ± 0.16 | 1.01 ± 0.01 | 20.91 ± 1.60 |
| PYR020 | Batch | 30 | 1.5 | 0.23 ± 0.00 | 89.95 ± 4.72 | 0.85 ± 0.05 | 26.85 ± 1.60 | 1.10 ± 0.07 | 20.06 ± 2.08 |
| PYR020 | Fed-batch | 30 | 0.9 | 0.27 ± 0.02 | 90.61 ± 1.46 | 0.86 ± 0.02 | 26.73 ± 0.58 | 1.14 ± 0.02 | 24.17 ± 2.05 |

TABLE 3-continued

Production of pyruvate from the mutant strains in bioreactors.

| Strains | Bioreactor Mode | Medium[#] Glucose (g/L) | Medium[#] Acetate (g/L) | Growth Rate (hour$^{-1}$) | Pyruvate yield % of max. theoretical yield[†] | Pyruvate yield Conversion[‡] (g pyruvate/ g substrate) | Pyruvate Titer (g/L)[§] | Pyruvate Production Rate Volumetric (g/L/hour) | Pyruvate Production Rate Specific[¶] (mmol/gDW/ hour) |
|---|---|---|---|---|---|---|---|---|---|
| PYR004 | Batch | 30 | 1.5 | 0.56 ± 0.03 | 91.17 ± 0.02 | 0.87 ± 0.00 | 27.35 ± 0.01 | 0.88 ± 0.00 | 15.11 ± 4.61 |
| PYR004 | Batch | 30 | 3.0 | 0.52 ± 0.01 | 86.63 ± 0.40 | 0.80 ± 0.01 | 26.36 ± 0.41 | 1.17 ± 0.02 | 11.45 ± 3.55 |
| PYR004 | Fed-batch | 30 | 3.0 | 0.53 ± 0.03 | 84.70 ± 2.70 | 0.77 ± 0.01 | 25.32 ± 0.43 | 1.37 ± 0.02 | 17.09 ± 6.71 |
| PYR020 | Batch* | 48 | 2.6 | 0.22 ± 0.02 | 85.63 ± 3.54 | 0.82 ± 0.04 | 40.74 ± 2.09 | 0.51 ± 0.04 | 26.36 ± 3.10 |

[#]The first six experiments were done in a minimal salts medium (not M9) supplemented with glucose and acetate (see methods for details). In the last experiment, the medium was ASGH hydrolysate which contained 48 g/L glucose, 27 g/L xylose and 2.6 g/L acetate (as determined by HPLC).
[†]Percent of theoretical yield is calculated as the pyruvate concentration divided by the theoretical maximum production of pyruvate (2 mmol of pyruvate per mmol of glucose). Acetate was also taken account for calculating the theoretical maximum production (0.5 mmol of pyruvate per mmol of acetate). The yield was adjusted by the culture volume loss due to the liquid evaporation in shake flasks under aerobic conditions.
[‡]Conversion is expressed as the gram of pyruvate produced per gram of total carbon source (including glucose and acetate). It was adjusted to account for the volume of added buffer to maintain the bioreactor at pH 7.
[§]The reported titer is the concentration determined by HPLC (and does not account for the volume of added buffer).
[¶]The specific production rate is the pyruvate production rate per gram of cell dry weight (gDW) during exponential growth.
The numbers that follow the ± sign are standard deviations (SD) from duplicate bioreactor experiments.

Production of Ethanol by PYR-Derived Strains

Pyruvate is a precursor to many metabolites, fuels, and chemicals. To test whether the engineered pyruvate strains could produce other chemicals, we further engineered the strains to convert pyruvate into ethanol. The pJGG2 plasmid was added which contains the PET cassette—pyruvate decarboxylase (pdc) and alcohol dehydrogenase (adhB)—from *Zymomonas mobilis* under the control of an IPTG inducible lac promoter. Ethanol production was measured under anaerobic conditions since producing ethanol recycles NADH generated by glycolysis. However, under anaerobic conditions pyruvate formate lyase (PflAB) converts pyruvate into acetyl-CoA and formate, and so pflB was additionally deleted from the pyruvate strains to create four ethanol strains: EH010-pflB, EH020-pflB, EH030-pflB and EH040-pflB.

Figure 8A:
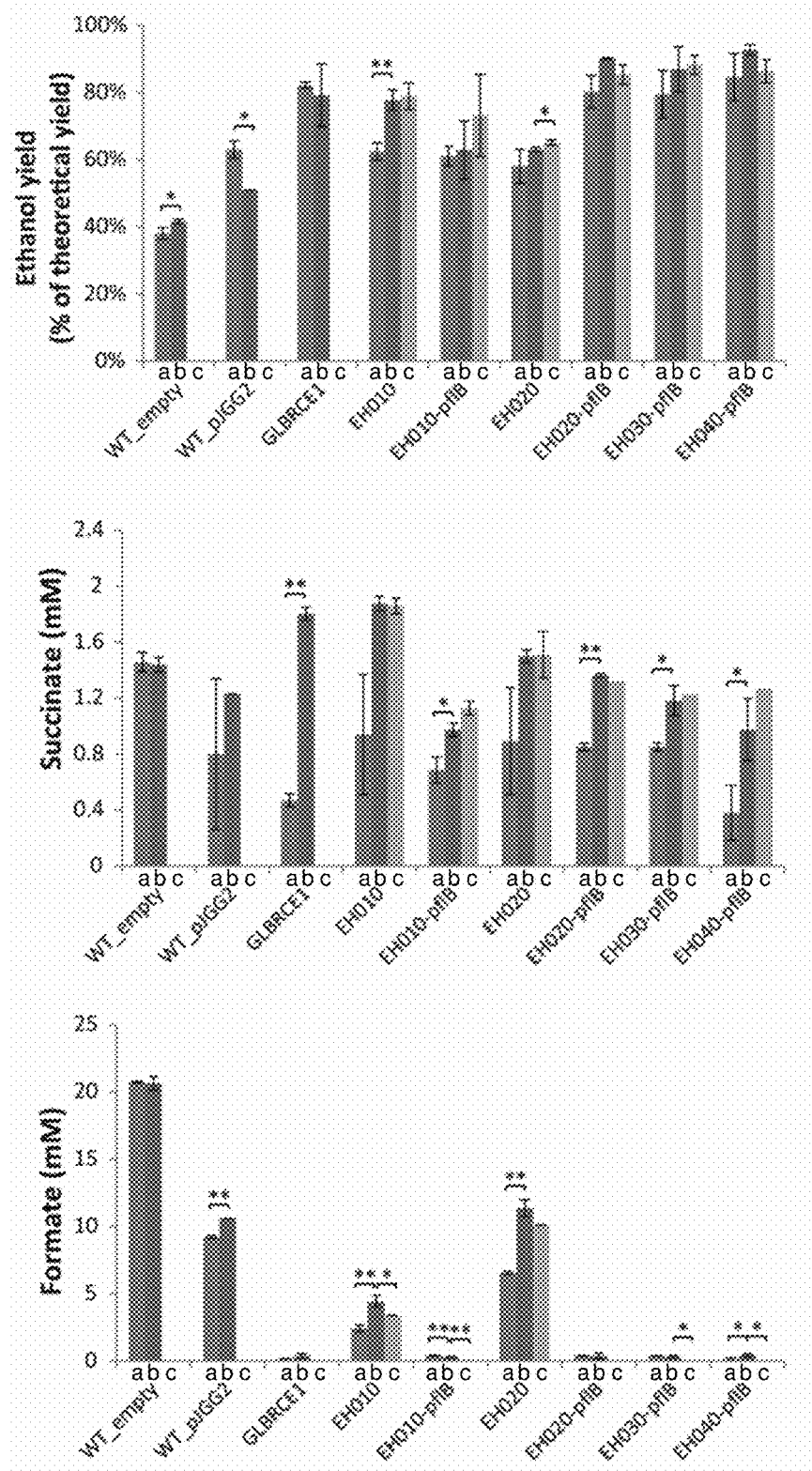
FIGS. 8A-8B show product secretion from various strains under anaerobic conditions. Secretion of ethanol, succinate, and formate is shown in FIG. 8A. Secretion of acetate and lactate is shown in FIG. 8B. All experiments were performed anaerobically in hungate tubes in M9 minimal media. Columns marked "a" correspond to fermentations containing 1.98 g/L glucose and 0.02 g/L acetate. Multiple samples were taken over 48 hours, which reduced the culture volume by about 50%. Columns marked (b) correspond to fermentations in M9 medium with 1.98 g/L glucose and 0.02 g/L acetate for 24 hours, but only three samples were taken at 16, 20 and 24 hours. Columns marked (c) correspond to fermentations in M9 minimal medium with more acetate (0.1 g/L) and 1.9 g/L glucose for 24 hours, with only three samples. Error bars represent standard errors among three replicates. Percent of theoretical yield was calculated as the ethanol concentration divided by the theoretical maximum production of ethanol (2 mmol of ethanol per mmol of glucose plus 0.67 mmol of ethanol per mmol of acetate). t-tests were used to determine significant differences in product concentrations between different fermentations (a, b, and c columns) where * and ** indicates the p-value is between 0.01 and 0.05, or less than 0.01, respectively.
Figure 8B:
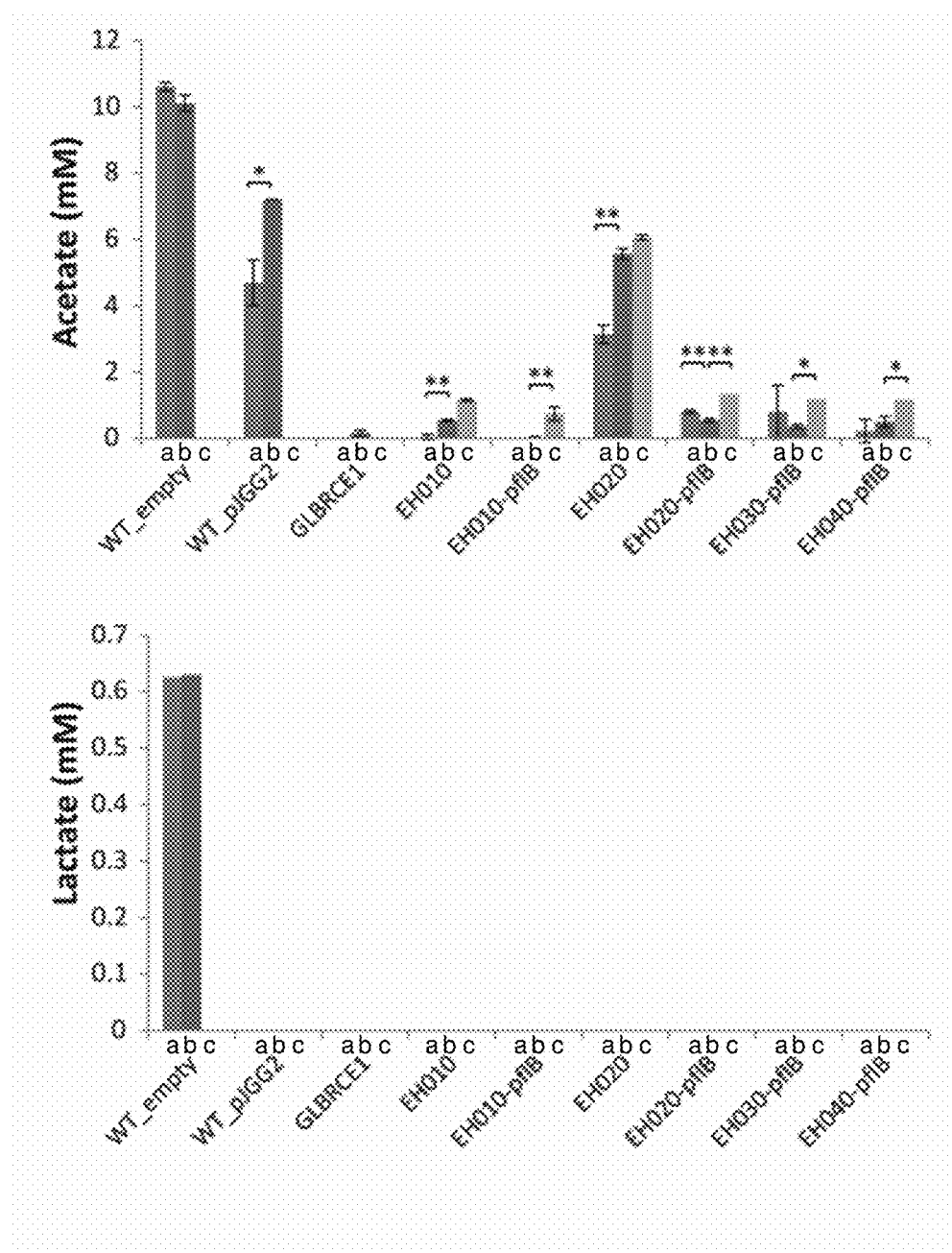

Anaerobic fermentations in M9 minimal media supplemented with glucose (1.98 g/L) and acetate (0.02 g/L) were carried out in hungate tubes. Three control strains were included: the parent strain (BW25113) with empty vector (pBBR1-MSC5), parent strain with pJGG2 plasmid, and an ethanol production strain, GLBRCE1 (which lacks ackA, NW, and ldhA and expresses the PET cassette from the chromosome and pJGG2 plasmid [36]). In the parent strain, expressing the PET cassette using pJGG2 increased the growth rate, ethanol yield (by ~66%), and ethanol production rate compared to the empty vector (Table 4). The improved growth and ethanol production is likely a result of enhanced NADH recycling. Compared to the parent strain with pJGG2, all strains engineered to produce ethanol (GLBRCE1, EH010-pflB, EH020-pflB, EH030-pflB and EH040-pflB) had lower growth rates (Table 4). Three mutants (EH020-pflB, EH030-pflB and EH040-pflB) had between ~16% and ~21% higher ethanol yields compared to the parent strain with pJGG2, and had similar yields to GLBRCE1 (FIG. 8A). Two of these mutants (EH020-pflB and EH040-pflB) had higher volumetric productivity than both GLBRCE1 and the parent strain with pJGG2 (Table 4). Additional fermentations were performed using medium with more acetate (0.1 g/L with 1.9 g/L glucose) and/or reduced sampling frequency, and the ethanol yields and byproduct concentrations did not appear to change when more acetate was supplemented (FIGS. 8A and 8B).

TABLE 4

Production of ethanol from the parent and mutant strains.

| Strains[§] | Growth Rate (hour$^{-1}$) | M9 Medium with Glucose (g/L) | M9 Medium with Acetate (g/L) | Ethanol yield % of max. theoretical yield[†] | Ethanol yield Conversion[‡] (g pyruvate/ g substrate) | Ethanol Titer (g/L) | Ethanol Production Rate Volumetric (g/L/hour) | Ethanol Production Rate Specific[¶] (mmol/gDW/ hour) |
|---|---|---|---|---|---|---|---|---|
| BW25113 + pBBR1-MSC5 | 0.28 ± 0.00 | 2 | 0 | 38.04 ± 1.70 | 0.19 ± 0.01 | 0.39 ± 0.02 | 0.02 ± 0.00 | 6.26 ± 0.10 |
| BW25113 + pJGG2 | 0.37 ± 0.02 | 2 | 0 | 63.06 ± 2.59 | 0.32 ± 0.01 | 0.64 ± 0.03 | 0.04 ± 0.00 | 11.71 ± 1.09 |
| GLBRCE1 | 0.16 ± 0.02 | 2 | 0 | 82.21 ± 0.91 | 0.42 ± 0.01 | 0.83 ± 0.01 | 0.03 ± 0.00 | 16.08 ± 0.78 |
| EH010-pflB | 0.18 ± 0.01 | 1.98 | 0.02 | 61.81 ± 6.77 | 0.31 ± 0.03 | 0.62 ± 0.07 | 0.02 ± 0.00 | 16.61 ± 1.15 |
| EH020-pflB | 0.25 ± 0.02 | 1.98 | 0.02 | 80.23 ± 4.84 | 0.41 ± 0.02 | 0.81 ± 0.05 | 0.04 ± 0.00 | 23.10 ± 1.48 |
| EH030-pflB | 0.19 ± 0.05 | 1.98 | 0.02 | 79.47 ± 7.12 | 0.40 ± 0.04 | 0.80 ± 0.07 | 0.02 ± 0.00 | 19.29 ± 1.12 |
| EH040-pflB | 0.22 ± 0.03 | 1.98 | 0.02 | 84.59 ± 7.03 | 0.43 ± 0.04 | 0.85 ± 0.07 | 0.04 ± 0.00 | 22.37 ± 2.28 |

[§]Strains GLBRCE1, EH010-pflB, EH020-pflB, EH030-pflB, and EH040-pflB all contain pJGG2.
[†]Percent of theoretical yield is calculated as the ethanol concentration divided by the theoretical maximum production of ethanol (2 mmol of ethanol per mmol of glucose). Acetate is also taken account for calculating the theoretical maximum production (0.67 mmol of ethanol per mmol of glucose).
[‡]The conversion is expressed as the gram of ethanol produced per gram of carbon.
[¶]The specific production rate is the pyruvate production rate per gram of cell dry weight (gDW) during exponential growth. The numbers that follow the ± sign are standard deviations (SD) from triplicate experiments.

Discussion

Optimizing production of a specific metabolite usually involves increasing synthesis of its precursors. Pyruvate is a starting compound for synthesizing a variety of biofuels (e.g., ethanol, 1-butanol and isobutanol) and chemicals. A high-yield pyruvate producing strain has great potential for creating strains to produce valuable chemicals. In this study, a genome-scale metabolic model of *E. coli* and OptORF were used to identify gene deletion targets to improve pyruvate production. Strains constructed based on the computational predictions produced high levels of pyruvate and adaptive evolution of two strains increased pyruvate yields, titers and volumetric production rates. Further engineering of these platform pyruvate strains resulted in strains with high ethanol production.

All the designed strains over-produced pyruvate. The gene targets prevented pyruvate consumption by removing competing pathways and reduced growth by eliminating more energetically efficient routes for NADPH and glutamate production. The mutations involved shutting down the pentose phosphate pathway, reducing TCA cycle flux, and lowering biomass production (FIGS. 2A-2D). All of the mutants were predicted to have increased glycolytic fluxes and coupling between growth and pyruvate production. Two of the strains immediately exhibited high pyruvate yields, while two other strains were adaptively evolved to improve production rates and/or yields.

All the pyruvate strains have pyruvate dehydrogenase subunits deleted (either aceE or lpdA). The model predicted that other pathways (besides pyruvate-formate lyase) could be used to produce acetyl-CoA. Acetyl-CoA could be made from acetaldehyde via acetaldehyde dehydrogenase (MhpF), where acetaldehyde is produced by threonine degradation and other reactions. Acetyl-CoA could also be produced by 2-amino-3-ketobutyrate CoA ligase (Kbl) from threonine degradation. However, all of the mutants were unable to grow in the absence of acetate, suggesting that these other pathways are not active at high enough levels. Acetate was consumed by all the pyruvate strains, except PYR001, presumably to generate acetyl-CoA by acetyl-CoA synthetase. The amount of acetate available (0.34-3.4 mM) was greater than or close to the amount acetyl-CoA needed for biomass (estimated as the product of the biomass concentration and acetyl-CoA biomass requirement, which is 3.7 mmol acetyl-CoA per gDW) [37]. In the ethanol production study, the mutants with increased fluxes of ethanol synthesis were observed to grow faster, which is also probably caused by the generation of acetaldehyde and then converted to acetyl-CoA, while another possibility is the balancing of NADH.

When the resulting pyruvate strains were re-engineered for ethanol production, three of the resulting strains achieved high ethanol yields (EH020-pflB, EH030-pflB and EH040-pflB) under anaerobic conditions. Deleting pflB and expressing the PET cassette increased ethanol as expected, except for EH010-pflB. EH010-pflB (derived from PYR010), had the lowest yield of the mutants with pflB deletion and PET addition. Among all the strains tested, EH010-pflB is closest genetically to GLBRCE1. Both EH010-pflB and GLBRCE1 have ldhA, pta and pflB deletions. Even though EH010-pflB has two additional deletions, aceE and cyoA, neither gene would be expected to be expressed anaerobically [38]. Thus, the significantly lower ethanol yield in EH010-pflB compared with GLBRCE1 was unexpected. GLBRCE1 was derived from a closely-related background strain (MG1655, compared to BW25113) and has an extra chromosomal copy of the PET cassette. This additional copy of the PET cassette could lead to higher PET expression levels and ethanol production in GLBRCE1. When compared to EH010, EH010-pflB should have reduced formate production (which it does, see FIG. 8A) and increased availability of pyruvate. However, EH010-pflB and EH010 exhibited similar ethanol yields (FIG. 8A). For the EH010-pflB strain, only 80% of the carbon was recovered in the biomass and measured products (which is lower than the other strains) and so it is possible that some other metabolite (not detected by HPLC) was secreted by EH010-pflB.

Yeast and bacterial strains have previously been engineered for pyruvate production [20, 22-24]. The strains usually require additional nutrients besides glucose (e.g., yeast extract, tryptone, thiamine) which will increase the cost for commercial production. An *E. coli* strain TC44 was previously reported to show the highest pyruvate production with 78% of theoretical yield and 1.2 g/L/hour production rate, when supplemented with thiamine. Our strain, PYR020, uses only mineral salt medium and reaches significantly higher yield (92% of theoretical yield) and a high production rate of 1.01 g/L/hour. This strain also could utilize cheaper hydrolysate feedstock to produce pyruvate with a high yield and titer. While PYR020 requires acetate for growth, acetate is commonly found in lignocellulosic hydrolysates. The PYR020 and PYR004 strains have the highest pyruvate production yield reported so far, and will be an ideal platform to create new strains to produce other important chemicals derived from pyruvate.

REFERENCES

1. Ingram L O, Conway T, Clark D P, Sewell G W, Preston J F. Genetic-Engineering of Ethanol-Production in *Escherichia-Coli*. Appl Environ Microb. 1987; 53(10): 2420-5. PubMed PMID: WOS:A1987K354800024.
2. Atsumi S, Hanai T, Liao J C. Non-fermentative pathways for synthesis of branched-chain higher alcohols as biofuels. Nature. 2008; 451(7174):86-U13. doi: Doi 10.1038/Nature06450. PubMed PMID: WOS:000252079300039.
3. Steen E J, Kang Y S, Bokinsky G, Hu Z H, Schirmer A, McClure A, et al. Microbial production of fatty-acid-derived fuels and chemicals from plant biomass. Nature. 2010; 463(7280):559-U182. doi: Doi 10.1038/Nature08721. PubMed PMID: WOS:000273981100055.
4. Beller H R, Goh E B, Keasling J D. Genes Involved in Long-Chain Alkene Biosynthesis in *Micrococcus luteus*. Appl Environ Microb. 2010; 76(4):1212-23. doi: Doi 10.1128/Aem.02312-09. PubMed PMID: WOS: 000274328900029.
5. Schirmer A, Rude M A, Li X Z, Popova E, del Cardayre S B. Microbial Biosynthesis of Alkanes. Science. 2010; 329(5991):559-62. doi: DOI 10.1126/science. 1187936. PubMed PMID: WOS:000280483500035.
6. Hawkins K M, Smolke C D. Production of benzylisoquinoline alkaloids in *Saccharomyces cerevisiae*. Nat Chem Biol. 2008; 4(9):564-73. doi: Doi 10.1038/Nchembio.105. PubMed PMID: WOS:000258597700015.
7. Pfeifer B A, Admiraal S J, Gramajo H, Cane D E, Khosla C. Biosynthesis of complex polyketides in a metabolically engineered strain of *E-coli*. Science. 2001; 291(5509): 1790-2. doi: DOI 10.1126/science.1058092. PubMed PMID: WOS:000167320600060.
8. Siewers V, San-Bento R, Nielsen J. Implementation of Communication-Mediating Domains for Non-Ribosomal Peptide Production in *Saccharomyces cerevisiae*. Biotechnol Bioeng. 2010; 106(5):841-4. doi: Doi 10.1002/Bit.22739. PubMed PMID: WOS:000280058800014.
9. Ro D K, Paradise E M, Ouellet M, Fisher K J, Newman K L, Ndungu J M, et al. Production of the antimalarial drug precursor artemisinic acid in engineered yeast. Nature. 2006; 440(7086):940-3. doi: Doi 10.1038/Nature04640. PubMed PMID: WOS:000236736700042.
10. Leonard E, Ajikumar P K, Thayer K, Xiao W H, Mo J D, Tidor B, et al. Combining metabolic and protein engineering of a terpenoid biosynthetic pathway for overproduction and selectivity control. Proceedings of the National Academy of Sciences of the United States of America. 2010; 107(31):13654-9. doi: DOI 10.1073/pnas.1006138107. PubMed PMID: WOS:000280605900021.
11. Asadollahi M A, Maury J, Patil K R, Schalk M, Clark A, Nielsen J. Enhancing sesquiterpene production in *Saccharomyces cerevisiae* through in silico driven metabolic engineering. Metab Eng. 2009; 11(6):328-34. doi: DOI 10.1016/j.ymben.2009.07.001. PubMed PMID: WOS:000272036700002.
12. Park J H, Lee K H, Kim T Y, Lee S Y. Metabolic engineering of *Escherichia coli* for the production of L-valine based on transcriptome analysis and in silico gene knockout simulation. Proceedings of the National Academy of Sciences of the United States of America. 2007; 104(19):7797-802. doi: DOI 10.1073/pnas.0702609104. PubMed PMID: WOS:000246461500015.
13. Fong S S, Burgard A P, Herring C D, Knight E M, Blattner F R, Maranas C D, et al. In silico design and adaptive evolution of *Escherichia coli* for production of lactic acid. Biotechnol Bioeng. 2005; 91(5):643-8. doi: Doi 10.1002/Bit.20542. PubMed PMID: WOS:000231523600012.
14. Zhang X L, Jantama K, Moore J C, Jarboe L R, Shanmugam K T, Ingram L O. Metabolic evolution of energy-conserving pathways for succinate production in *Escherichia coli*. Proceedings of the National Academy of Sciences of the United States of America. 2009; 106(48): 20180-5. doi: DOI 10.1073/pnas.0905396106. PubMed PMID: WOS:000272254400012.
15. Nakamura C E, Whited G M. Metabolic engineering for the microbial production of 1,3-propanediol. Curr Opin Biotech. 2003; 14(5):454-9. doi: DOI 10.1016/j.copbio.2003.08.005. PubMed PMID: WOS:000186448200002.
16. Wierckx N J P, Ballerstedt H, de Bont J A M, Wery J. Engineering of solvent-tolerant *Pseudomonas putida* S12 for bioproduction of phenol from glucose. Appl Environ Microb. 2005; 71(12):8221-7. doi: Doi 10.1128/Aem.71.12.8221-8227.2005. PubMed PMID: WOS:000234417600072.
17. Zha W J, Rubin-Pitel S B, Shao Z Y, Zhao H M. Improving cellular malonyl-CoA level in *Escherichia coli* via metabolic engineering. Metab Eng. 2009; 11(3):192-8. doi: DOI 10.1016/j.ymben.2009.01.005. PubMed PMID: WOS:000265565300008.
18. Ravi R. Gokarn M A E, Elliot Altman, inventor Pyruvate carboxylase overexpression for enhanced production of oxaloacetate-derived biochemicals in microbial cells 1999.
19. Zhu Y H, Eiteman M A, Altman R, Altman E. High Glycolytic Flux Improves Pyruvate Production by a Metabolically Engineered *Escherichia coli* Strain. Appl Environ Microb. 2008; 74(21):6649-55. doi: Doi 10.1128/Aem.01610-08. PubMed PMID: WOS:000260429600020.
20. Tomar A, Eiteman M A, Altman E. The effect of acetate pathway mutations on the production of pyruvate in *Escherichia coli*. Applied Microbiology and Biotechnology. 2003; 62(1):76-82. doi: DOI 10.1007/s00253-003-1234-6. PubMed PMID: WOS:000184014000010.
21. Causey T B, Shanmugam K T, Yomano L P, Ingram L O. Engineering *Escherichia coli* for efficient conversion of glucose to pyruvate. Proceedings of the National Academy of Sciences of the United States of America. 2004; 101(8):2235-40. doi: DOI 10.1073/pnas.0308171100. PubMed PMID: WOS:000220140400004.
22. Xu G Q, Hua Q, Duan N J, Liu L M, Chen J. Regulation of thiamine synthesis in *Saccharomyces cerevisiae* for improved pyruvate production. Yeast. 2012; 29(6):209-17. doi: Doi 10.1002/Yea.2902. PubMed PMID: WOS:000305078900002.
23. Wang Z K, Gao C J, Wang Q, Liang Q F, Qi Q S. Production of pyruvate in *Saccharomyces cerevisiae* through adaptive evolution and rational cofactor metabolic engineering. Biochem Eng J. 2012; 67:126-31. doi: DOI 10.1016/j.bej.2012.06.006. PubMed PMID: WOS:000310945100017.
24. Wieschalka S, Blombach B, Eikmanns B J. Engineering *Corynebacterium glutamicum* for the production of pyruvate. Applied Microbiology and Biotechnology. 2012; 94(2):449-59. doi: DOI 10.1007/s00253-011-3843-9. PubMed PMID: WOS:000302035500014.
25. Mark A. Eiteman E A, inventorMicrobial production of pyruvate and pyruvate derivatives patent US 20,100,304, 450. 2012.
26. Kim J, Reed J L. OptORF: Optimal metabolic and regulatory perturbations for metabolic engineering of microbial strains. Bmc Syst Biol. 2010; 4. doi: Artn 53 Doi 10.1186/1752-0509-4-53. PubMed PMID: WOS:000278257700002.
27. Peng L, Shimizu K. Global metabolic regulation analysis for *Escherichia coli* K12 based on protein expression by 2-dimensional electrophoresis and enzyme activity measurement. Applied Microbiology and Biotechnology. 2003; 61(2):163-78. doi: DOI 10.1007/s00253-002-1202-6. PubMed PMID: WOS:000182702800011.
28. Sawers G, Watson G. A glycyl radical solution: oxygen-dependent interconversion of pyruvate formate-lyase. Molecular Microbiology. 1998; 29(4):945-54. doi: DOI 10.1046/j.1365-2958.1998.00941.x. PubMed PMID: WOS:000075451700002.
29. Bologna F P, Campos-Bermudez V A, Saavedra D D, Andreo C S, Drincovich M F. Characterization of *Escherichia coli* EutD: a Phosphotransacetylase of the Ethanolamine Operon. J Microbiol. 2010; 48(5):629-36. doi: DOI 10.1007/s12275-010-0091-0. PubMed PMID: WOS:000283630100012.
30. Zhou L, Zuo Z R, Chen X Z, Niu D D, Tian K M, Prior B A, et al. Evaluation of Genetic Manipulation Strategies on d-Lactate Production by *Escherichia coli*. Curr Microbiol. 2011; 62(3):981-9. doi: DOI 10.1007/s00284-010-9817-9. PubMed PMID: WOS:000287754500044.
31. Tarmy E M, Kaplan N O. Kinetics of *Escherichia Coli* B D-Lactate Dehydrogenase and Evidence for Pyruvate-Controlled Change in Conformation. Journal of Biological Chemistry. 1968; 243(10):2587-&. PubMed PMID: WOS:A1968B201700019.
32. Sawers G, Hesslinger C, Muller N, Kaiser M. The glycyl radical enzyme TdcE can replace pyruvate formate-lyase in glucose fermentation. Journal of Bacteriology. 1998; 180(14):3509-16. PubMed PMID: WOS:000074720100003.
33. Nagy P L, Marolewski A, Benkovic S J, Zalkin H. Formyltetrahydrofolate Hydrolase, a Regulatory Enzyme That Functions to Balance Pools of Tetrahydrofolate and One-Carbon Tetrahydrofolate Adducts in Escherichia-Coli. Journal of Bacteriology. 1995; 177(5):1292-8. PubMed PMID: WOS:A1995QJ43900023.
34. Baba T, Ara T, Hasegawa M, Takai Y, Okumura Y, Baba M, et al. Construction of Escherichia coli K-12 in-frame, single-gene knockout mutants: the Keio collection. Mol Syst Biol. 2006; 2. doi: Artn 2006.0008 Doi 10.1038/Msb4100050. PubMed PMID: WOS:000243245400009.
35. Mills T Y, Sandoval N R, Gill R T. Cellulosic hydrolysate toxicity and tolerance mechanisms in Escherichia coli. Biotechnol Biofuels. 2009; 2. doi: Artn 26 10.1186/1754-6834-2-26. PubMed PMID: WOS:000272095400002.
36. Schwalbach M S, Keating D H, Tremaine M, Marner W D, Zhang Y P, Bothfeld W, et al. Complex Physiology and Compound Stress Responses during Fermentation of Alkali-Pretreated Corn Stover Hydrolysate by an Escherichia coli Ethanologen. Appl Environ Microb. 2012; 78(9):3442-57. doi: Doi 10.1128/Aem.07329-11. PubMed PMID: WOS:000302807500047.
37. Neidhardt F C, John L. Ingraham, and Moselio Schaechter. Physiology of the bacterial cell: a molecular approach. Sunderland, Mass.: Sinauer Associates; 1990.
38. Toya Y, Nakahigashi K, Tomita M, Shimizu K. Metabolic regulation analysis of wild-type and arcA mutant Escherichia coli under nitrate conditions using different levels of omics data. Molecular bioSystems. 2012; 8(10): 2593-604. Epub 2012/07/14. doi: 10.1039/c2mb25069a. PubMed PMID: 22790675.
39. Datsenko K A, Wanner B L. One-step inactivation of chromosomal genes in Escherichia coli K-12 using PCR products. Proceedings of the National Academy of Sciences of the United States of America. 2000; 97(12): 6640-5. doi: DOI 10.1073/pnas.120163297. PubMed PMID: WOS:000087526300074.
40. Causey T B, Zhou S, Shanmugam K T, Ingram L O. Engineering the metabolism of Escherichia coli W3110 for the conversion of sugar to redox-neutral and oxidized products: Homoacetate production. Proceedings of the National Academy of Sciences of the United States of America. 2003; 100(3):825-32. doi: 10.1073/pnas.0337684100. PubMed PMID: WOS:000180838100014.
41. Baumler D J, Peplinski R G, Reed J L, Glasner J D, Perna N T. The evolution of metabolic networks of E. coli. Bmc Syst Biol. 2011; 5:182. doi: Artn 182 Doi 10.1186/1752-0509-5-182. PubMed PMID: WOS:000297698400001.
42. Feist A M, Zielinski D C, Orth J D, Schellenberger J, Herrgard M J, Palsson B O. Model-driven evaluation of the production potential for growth-coupled products of Escherichia coli. Metab Eng. 2010; 12(3):173-86. doi: DOI 10.1016/j.ymben.2009.10.003. PubMed PMID: WOS:000276821400001.
43. Reed J L, Vo T D, Schilling C H, Palsson B O. An expanded genome-scale model of Escherichia coli K-12 (iJR904 GSM/GPR). Genome Biol. 2003; 4(9). doi: Artn R54 Doi 10.1186/Gb-2003-4-9-R54. PubMed PMID: WOS:000185048100007.
44. Miller, J. H. Experiments in Molecular Genetics. Cold Spring Harbor Laboratory, (1972), 433.

We claim:

1. A microorganism comprising activity-reducing or activity-ablating mutations in endogenous genes encoding a pyruvate dehydrogenase, a pyruvate oxidase, a lactate dehydrogenase, and one or more enzymes selected from the group consisting of a 6-phosphogluconate dehydrogenase and a glutamate dehydrogenase.

2. The microorganism of claim 1 wherein the microorganism comprises an activity-reducing or activity-ablating mutation in an endogenous gene encoding a 6-phosphogluconate dehydrogenase.

3. The microorganism of claim 1 wherein the microorganism comprises an activity-reducing or activity-ablating mutation in an endogenous gene encoding a glutamate dehydrogenase.

4. The microorganism of claim 1 wherein the microorganism comprises an activity-reducing or activity-ablating mutation in an endogenous gene encoding a 6-phosphogluconate dehydrogenase and an endogenous gene encoding a glutamate dehydrogenase.

5. The microorganism of claim 1 further comprising an activity-reducing or activity-ablating mutation in an endogenous gene encoding an enzyme selected from the group consisting of a pyruvate formate lyase and a pyruvate formate lyase activating enzyme.

6. The microorganism of claim 1 wherein the microorganism is modified to express a pyruvate decarboxylase and an alcohol dehydrogenase.

7. The microorganism of claim 1 wherein the microorganism comprises one or more recombinant genes encoding one or more enzymes selected from the group consisting of a pyruvate decarboxylase and an alcohol dehydrogenase.

8. The microorganism of claim 7 further comprising an activity-reducing or activity-ablating mutation in an endogenous gene encoding an enzyme selected from the group consisting of a pyruvate formate lyase and a pyruvate formate lyase activating enzyme.

9. The microorganism of claim 1 wherein the activity-reducing or activity-ablating mutations in the endogenous genes are independently selected from the group consisting of a nucleotide substitution in the endogenous gene, a nucleotide insertion in the endogenous gene, a partial deletion of the endogenous gene, and a complete deletion of the endogenous gene.

10. The microorganism of claim 1 wherein the microorganism is a bacterium or a yeast.

11. The microorganism of claim 1 wherein the microorganism is a bacterium.

12. The microorganism of claim 1 wherein the microorganism is an evolved microorganism produced by sequentially culturing a precursor microorganism in media comprising decreasing concentrations of acetate, wherein the precursor microorganism comprises activity-reducing or activity-ablating mutations in (a) endogenous genes encoding a pyruvate dehydrogenase, a pyruvate oxidase, and a lactate dehydrogenase, and (b) one or more endogenous genes encoding one or more enzymes selected from the group consisting of a 6-phosphogluconate dehydrogenase and a glutamate dehydrogenase, wherein the evolved microorganism exhibits one or more of increased growth rate compared to the precursor microorganism and increased pyruvate production compared to the precursor microorganism, and wherein the evolved microorganism comprises the activity-reducing or activity-ablating mutations in the endogenous genes of (a) and (b).

13. The microorganism of claim 12 wherein the concentrations of acetate in the media in which the precursor microorganism is sequentially cultured to produce the microorganism range from about 0.1 mg/L acetate to about 3 g/L acetate.

14. The microorganism of claim 12 wherein the evolved microorganism further comprises an activity-reducing or activity-ablating mutation in an endogenous gene encoding an enzyme selected from the group consisting of a pyruvate formate lyase and a pyruvate formate lyase activating enzyme.

15. The microorganism of claim 12 wherein the evolved microorganism is modified to express a pyruvate decarboxylase and an alcohol dehydrogenase.

16. The microorganism of claim 12 wherein the evolved microorganism comprises one or more recombinant genes encoding one or more enzymes selected from the group consisting of a pyruvate decarboxylase and an alcohol dehydrogenase.

17. A method of producing a chemical comprising culturing the microorganism of claim 1.

18. The method of claim 17 wherein the microorganism further comprises:
   an activity-reducing or activity-ablating mutation in an endogenous gene encoding an enzyme selected from the group consisting of a pyruvate formate lyase and a pyruvate formate lyase activating enzyme; and
   one or more recombinant genes encoding one or more enzymes selected from the group consisting of a pyruvate decarboxylase and an alcohol dehydrogenase.

19. The method of claim 17 wherein the culturing comprises culturing the microorganism in a medium, the chemical is selected from the group consisting of pyruvate and ethanol, and the method further comprises purifying the chemical from the medium.

20. The method of claim 17 wherein the culturing comprises culturing the microorganism in a medium comprising a biomass hydrolysate.

21. The method of claim 17 wherein the microorganism is an evolved microorganism produced by sequentially culturing a precursor microorganism in media comprising decreasing concentrations of acetate, wherein the precursor microorganism comprises activity-reducing or activity-ablating mutations in (a) endogenous genes encoding a pyruvate dehydrogenase, a pyruvate oxidase, and a lactate dehydrogenase, and (b) one or more endogenous genes encoding one or more enzymes selected from the group consisting of a 6-phosphogluconate dehydrogenase and a glutamate dehydrogenase, wherein the evolved microorganism exhibits one or more of increased growth rate compared to the precursor microorganism and increased pyruvate production compared to the precursor microorganism, and wherein the evolved microorganism comprises the activity-reducing or activity-ablating mutations in the endogenous genes of (a) and (b).

* * * * *

SEQUENCE LISTING

```
<160> NUMBER OF SEQ ID NOS: 48

<210> SEQ ID NO 1
<211> LENGTH: 2664
<212> TYPE: DNA
<213> ORGANISM: Escherichia coli

<400> SEQUENCE: 1
atgtcagaac gtttcccaaa tgacgtggat ccgatcgaaa ctcgcgactg gctccaggcg      60
atcgaatcgg tcatccgtga agaaggtgtt gagcgtgctc agtatctgat cgaccaactg     120
cttgctgaag cccgcaaagg cggtgtaaac gtagccgcag gcacaggtat cagcaactac     180
atcaacacca tccccgttga agaacaaccg gagtatccgg gtaatctgga actggaacgc     240
cgtattcgtt cagctatccg ctggaacgcc atcatgacgg tgctgcgtgc gtcgaaaaaa     300
gacctcgaac tgggcggcca tatggcgtcc ttccagtctt ccgcaaccat ttatgatgtg     360
tgctttaacc acttcttccg tgcacgcaac gagcaggatg gcggcgacct ggtttacttc     420
cagggccaca tctccccggg cgtgtacgct cgtgctttcc tggaaggtcg tctgactcag     480
gagcagctgg ataacttccg tcaggaagtt cacggcaatg gcctctcttc ctatccgcac     540
ccgaaactga tgccggaatt ctggcagttc ccgaccgtat ctatgggtct gggtccgatt     600
ggtgctattt accaggctaa attcctgaaa tatctggaac accgtggcct gaaagatacc     660
tctaaacaaa ccgtttacgc gttcctcggt gacggtgaaa tggacgaacc ggaatccaaa     720
ggtgcgatca ccatcgctac ccgtgaaaaa ctggataacc tggtcttcgt tatcaactgt     780
```

|  |  |
|---|---|
| aacctgcagc gtcttgacgg cccggtcacc ggtaacggca agatcatcaa cgaactggaa | 840 |
| ggcatcttcg aaggtgctgg ctggaacgtg atcaaagtga tgtggggtag ccgttgggat | 900 |
| gaactgctgc gtaaggatac cagcggtaaa ctgatccagc tgatgaacga aaccgttgac | 960 |
| ggcgactacc agaccttcaa atcgaaagat ggtgcgtacg ttcgtgaaca cttcttcggt | 1020 |
| aaatatcctg aaccgcagc actggttgca gactggactg acgagcagat ctgggcactg | 1080 |
| aaccgtggtg gtcacgatcc gaagaaaatc tacgctgcat tcaagaaagc gcaggaaacc | 1140 |
| aaaggcaaag cgacagtaat ccttgctcat accattaaag gttacggcat gggcgacgcg | 1200 |
| gctgaaggta aaacatcgc gcaccaggtt aagaaaatga catgacgg tgtgcgtcat | 1260 |
| atccgcgacc gtttcaatgt gccggtgtct gatgcagata tcgaaaaact gccgtacatc | 1320 |
| accttcccgg aaggttctga agagcatacc tatctgcacg ctcagcgtca gaaactgcac | 1380 |
| ggttatctgc caagccgtca gccgaacttc accgagaagc ttgagctgcc gagcctgcaa | 1440 |
| gacttcggcg cgctgttgga agagcagagc aaagagatct ctaccactat cgctttcgtt | 1500 |
| cgtgctctga acgtgatgct gaagaacaag tcgatcaaag atcgtctggt accgatcatc | 1560 |
| gccgacgaag cgcgtacttt cggtatggaa ggtctgttcc gtcagattgg tatttacagc | 1620 |
| ccgaacggtc agcagtacac cccgcaggac cgcgagcagg ttgcttacta taagaagac | 1680 |
| gagaaaggtc agattctgca ggaagggatc aacgagctgg cgcaggttg ttcctggctg | 1740 |
| gcagcggcga cctcttacag caccaacaat ctgccgatga tcccgttcta catctattac | 1800 |
| tcgatgttcg gcttccagcg tattggcgat ctgtgctggg cggctggcga ccagcaagcg | 1860 |
| cgtggcttcc tgatcggcgg tacttccggt cgtaccaccc tgaacggcga aggtctgcag | 1920 |
| cacgaagatg gtcacagcca cattcagtcg ctgactatcc gaactgtat ctcttacgac | 1980 |
| ccggcttacg cttacgaagt tgctgtcatc atgcatgacg gtctggagcg tatgtacggt | 2040 |
| gaaaaacaag agaacgttta ctactacatc actacgctga acgaaaacta ccacatgccg | 2100 |
| gcaatgccgg aaggtgctga ggaaggtatc cgtaaaggta tctacaaact cgaaactatt | 2160 |
| gaaggtagca aaggtaaagt tcagctgctc ggctccggtt ctatcctgcg tcacgtccgt | 2220 |
| gaagcagctg agatcctggc gaaagattac ggcgtaggtt ctgacgttta tagcgtgacc | 2280 |
| tccttcaccg agctggcgcg tgatggtcag gattgtgaac gctggaacat gctgcacccg | 2340 |
| ctggaaactc cgcgcgttcc gtatatcgct caggtgatga acgacgctcc ggcagtggca | 2400 |
| tctaccgact atatgaaact gttcgctgag caggtccgta cttacgtacc ggctgacgac | 2460 |
| taccgcgtac tgggtactga tggcttcggt cgttccgaca gccgtgagaa cctgcgtcac | 2520 |
| cacttcgaag ttgatgcttc ttatgtcgtg gttgcggcgc tgggcgaact ggctaaacgt | 2580 |
| ggcgaaatcg ataagaaagt ggttgctgac gcaatcgcca aattcaacat cgatgcagat | 2640 |
| aaagttaacc cgcgtctggc gtaa | 2664 |

<210> SEQ ID NO 2
<211> LENGTH: 887
<212> TYPE: PRT
<213> ORGANISM: Escherichia coli

<400> SEQUENCE: 2

Met Ser Glu Arg Phe Pro Asn Asp Val Asp Pro Ile Glu Thr Arg Asp
1               5                   10                  15

Trp Leu Gln Ala Ile Glu Ser Val Ile Arg Glu Glu Gly Val Glu Arg
            20                  25                  30

Ala Gln Tyr Leu Ile Asp Gln Leu Leu Ala Glu Ala Arg Lys Gly Gly

```
            35                  40                  45
Val Asn Val Ala Ala Gly Thr Gly Ile Ser Asn Tyr Ile Asn Thr Ile
 50                  55                  60
Pro Val Glu Glu Gln Pro Glu Tyr Pro Gly Asn Leu Glu Leu Glu Arg
65                  70                  75                  80
Arg Ile Arg Ser Ala Ile Arg Trp Asn Ala Ile Met Thr Val Leu Arg
                 85                  90                  95
Ala Ser Lys Lys Asp Leu Glu Leu Gly Gly His Met Ala Ser Phe Gln
                100                 105                 110
Ser Ser Ala Thr Ile Tyr Asp Val Cys Phe Asn His Phe Phe Arg Ala
            115                 120                 125
Arg Asn Glu Gln Asp Gly Gly Asp Leu Val Tyr Phe Gln Gly His Ile
        130                 135                 140
Ser Pro Gly Val Tyr Ala Arg Ala Phe Leu Glu Gly Arg Leu Thr Gln
145                 150                 155                 160
Glu Gln Leu Asp Asn Phe Arg Gln Glu Val His Gly Asn Gly Leu Ser
                165                 170                 175
Ser Tyr Pro His Pro Lys Leu Met Pro Glu Phe Trp Gln Phe Pro Thr
            180                 185                 190
Val Ser Met Gly Leu Gly Pro Ile Gly Ala Ile Tyr Gln Ala Lys Phe
        195                 200                 205
Leu Lys Tyr Leu Glu His Arg Gly Leu Lys Asp Thr Ser Lys Gln Thr
210                 215                 220
Val Tyr Ala Phe Leu Gly Asp Gly Glu Met Asp Glu Pro Glu Ser Lys
225                 230                 235                 240
Gly Ala Ile Thr Ile Ala Thr Arg Glu Lys Leu Asp Asn Leu Val Phe
                245                 250                 255
Val Ile Asn Cys Asn Leu Gln Arg Leu Asp Gly Pro Val Thr Gly Asn
            260                 265                 270
Gly Lys Ile Ile Asn Glu Leu Glu Gly Ile Phe Glu Gly Ala Gly Trp
        275                 280                 285
Asn Val Ile Lys Val Met Trp Gly Ser Arg Trp Asp Glu Leu Leu Arg
290                 295                 300
Lys Asp Thr Ser Gly Lys Leu Ile Gln Leu Met Asn Glu Thr Val Asp
305                 310                 315                 320
Gly Asp Tyr Gln Thr Phe Lys Ser Lys Asp Gly Ala Tyr Val Arg Glu
                325                 330                 335
His Phe Phe Gly Lys Tyr Pro Glu Thr Ala Ala Leu Val Ala Asp Trp
            340                 345                 350
Thr Asp Glu Gln Ile Trp Ala Leu Asn Arg Gly Gly His Asp Pro Lys
        355                 360                 365
Lys Ile Tyr Ala Ala Phe Lys Ala Gln Glu Thr Lys Gly Lys Ala
    370                 375                 380
Thr Val Ile Leu Ala His Thr Ile Lys Gly Tyr Gly Met Gly Asp Ala
385                 390                 395                 400
Ala Glu Gly Lys Asn Ile Ala His Gln Val Lys Lys Met Asn Met Asp
                405                 410                 415
Gly Val Arg His Ile Arg Asp Arg Phe Asn Val Pro Val Ser Asp Ala
            420                 425                 430
Asp Ile Glu Lys Leu Pro Tyr Ile Thr Phe Pro Glu Gly Ser Glu Glu
        435                 440                 445
His Thr Tyr Leu His Ala Gln Arg Gln Lys Leu His Gly Tyr Leu Pro
    450                 455                 460
```

```
Ser Arg Gln Pro Asn Phe Thr Glu Lys Leu Glu Leu Pro Ser Leu Gln
465                 470                 475                 480

Asp Phe Gly Ala Leu Leu Glu Glu Gln Ser Lys Glu Ile Ser Thr Thr
                485                 490                 495

Ile Ala Phe Val Arg Ala Leu Asn Val Met Leu Lys Asn Lys Ser Ile
            500                 505                 510

Lys Asp Arg Leu Val Pro Ile Ile Ala Asp Glu Ala Arg Thr Phe Gly
        515                 520                 525

Met Glu Gly Leu Phe Arg Gln Ile Gly Ile Tyr Ser Pro Asn Gly Gln
    530                 535                 540

Gln Tyr Thr Pro Gln Asp Arg Glu Gln Val Ala Tyr Tyr Lys Glu Asp
545                 550                 555                 560

Glu Lys Gly Gln Ile Leu Gln Glu Gly Ile Asn Glu Leu Gly Ala Gly
                565                 570                 575

Cys Ser Trp Leu Ala Ala Ala Thr Ser Tyr Ser Thr Asn Asn Leu Pro
            580                 585                 590

Met Ile Pro Phe Tyr Ile Tyr Tyr Ser Met Phe Gly Phe Gln Arg Ile
        595                 600                 605

Gly Asp Leu Cys Trp Ala Ala Gly Asp Gln Gln Ala Arg Gly Phe Leu
    610                 615                 620

Ile Gly Gly Thr Ser Gly Arg Thr Thr Leu Asn Gly Glu Gly Leu Gln
625                 630                 635                 640

His Glu Asp Gly His Ser His Ile Gln Ser Leu Thr Ile Pro Asn Cys
                645                 650                 655

Ile Ser Tyr Asp Pro Ala Tyr Ala Tyr Glu Val Ala Val Ile Met His
            660                 665                 670

Asp Gly Leu Glu Arg Met Tyr Gly Glu Lys Gln Glu Asn Val Tyr Tyr
        675                 680                 685

Tyr Ile Thr Thr Leu Asn Glu Asn Tyr His Met Pro Ala Met Pro Glu
    690                 695                 700

Gly Ala Glu Glu Gly Ile Arg Lys Gly Ile Tyr Lys Leu Glu Thr Ile
705                 710                 715                 720

Glu Gly Ser Lys Gly Lys Val Gln Leu Leu Gly Ser Gly Ser Ile Leu
                725                 730                 735

Arg His Val Arg Glu Ala Ala Glu Ile Leu Ala Lys Asp Tyr Gly Val
            740                 745                 750

Gly Ser Asp Val Tyr Ser Val Thr Ser Phe Thr Glu Leu Ala Arg Asp
        755                 760                 765

Gly Gln Asp Cys Glu Arg Trp Asn Met Leu His Pro Leu Glu Thr Pro
    770                 775                 780

Arg Val Pro Tyr Ile Ala Gln Val Met Asn Asp Ala Pro Ala Val Ala
785                 790                 795                 800

Ser Thr Asp Tyr Met Lys Leu Phe Ala Glu Gln Val Arg Thr Tyr Val
                805                 810                 815

Pro Ala Asp Asp Tyr Arg Val Leu Gly Thr Asp Gly Phe Gly Arg Ser
            820                 825                 830

Asp Ser Arg Glu Asn Leu Arg His His Phe Glu Val Asp Ala Ser Tyr
        835                 840                 845

Val Val Val Ala Ala Leu Gly Glu Leu Ala Lys Arg Gly Glu Ile Asp
    850                 855                 860

Lys Lys Val Val Ala Asp Ala Ile Ala Lys Phe Asn Ile Asp Ala Asp
865                 870                 875                 880
```

Lys Val Asn Pro Arg Leu Ala
            885

<210> SEQ ID NO 3
<211> LENGTH: 1893
<212> TYPE: DNA
<213> ORGANISM: Escherichia coli

<400> SEQUENCE: 3

| | | | | | |
|---|---|---|---|---|---|
| atggctatcg | aaatcaaagt | accggacatc | ggggctgatg | aagttgaaat | caccgagatc | 60 |
| ctggtcaaag | tgggcgacaa | agttgaagcc | gaacagtcgc | tgatcaccgt | agaaggcgac | 120 |
| aaagcctcta | tggaagttcc | gtctccgcag | gcgggtatcg | ttaaagagat | caaagtctct | 180 |
| gttggcgata | aacccagac | cggcgcactg | attatgattt | tcgattccgc | cgacggtgca | 240 |
| gcagacgctg | cacctgctca | ggcagaagag | aagaaagaag | cagctccggc | agcagcacca | 300 |
| gcggctgcgg | cggcaaaaga | cgttaacgtt | ccggatatcg | gcagcgacga | agttgaagtg | 360 |
| accgaaatcc | tggtgaaagt | tggcgataaa | gttgaagctg | aacagtcgct | gatcaccgta | 420 |
| gaaggcgaca | aggcttctat | ggaagttccg | gctccgtttg | ctggcaccgt | gaaagagatc | 480 |
| aaagtgaacg | tgggtgacaa | agtgtctacc | ggctcgctga | ttatggtctt | cgaagtcgcg | 540 |
| ggtgaagcag | gcgcggcagc | tccggccgct | aaacaggaag | cagctccggc | agcggcccct | 600 |
| gcaccagcgg | ctggcgtgaa | agaagttaac | gttccggata | tcggcggtga | cgaagttgaa | 660 |
| gtgactgaag | tgatggtgaa | agtgggcgac | aaagttgccg | ctgaacagtc | actgatcacc | 720 |
| gtagaaggcg | acaaagcttc | tatggaagtt | ccggcgccgt | ttgcaggcgt | cgtgaaggaa | 780 |
| ctgaaagtca | acgttggcga | taaagtgaaa | actggctcgc | tgattatgat | cttcgaagtt | 840 |
| gaaggcgcag | cgcctgcggc | agctcctgcg | aaacaggaag | cggcagcgcc | ggcaccggca | 900 |
| gcaaaagctg | aagcccggc | agcagcacca | gctgcgaaag | cggaaggcaa | atctgaattt | 960 |
| gctgaaaacg | acgcttatgt | tcacgcgact | ccgctgatcc | gccgtctggc | acgcgagttt | 1020 |
| ggtgttaacc | ttgcgaaagt | gaagggcact | ggccgtaaag | gtcgtatcct | gcgcgaagac | 1080 |
| gttcaggctt | acgtgaaaga | agctatcaaa | cgtgcagaag | cagctccggc | agcgactggc | 1140 |
| ggtggtatcc | ctggcatgct | gccgtggccg | aaggtggact | tcagcaagtt | tggtgaaatc | 1200 |
| gaagaagtgg | aactgggccg | catccagaaa | atctctggtg | cgaacctgag | ccgtaactgg | 1260 |
| gtaatgatcc | cgcatgttac | tcacttcgac | aaaaccgata | tcaccgagtt | ggaagcgttc | 1320 |
| cgtaaacagc | agaacgaaga | agcggcgaaa | cgtaagctgg | atgtgaagat | caccccggtt | 1380 |
| gtcttcatca | tgaaagccgt | tgctgcagct | cttgagcaga | tgcctcgctt | caatagttcg | 1440 |
| ctgtcggaag | acgtcagcg | tctgacccctg | aagaaataca | tcaacatcgg | tgtggcggtg | 1500 |
| gataccccga | acgtctggt | tgttccggta | ttcaaagacg | tcaacaagaa | aggcatcatc | 1560 |
| gagctgtctc | gcgagctgat | gactatttct | aagaaagcgc | gtgacggtaa | gctgactgcg | 1620 |
| ggcgaaatgc | agggcggttg | cttcaccatc | tccagcatcg | gcggcctggg | tactacccac | 1680 |
| ttcgcgccga | ttgtgaacgc | gccggaagtg | gctatcctcg | gcgtttccaa | gtccgcgatg | 1740 |
| gagccggtgt | ggaatggtaa | agagttcgtg | ccgcgtctga | tgctgccgat | ttctctctcc | 1800 |
| ttcgaccacc | gcgtgatcga | cggtgctgat | ggtgcccgtt | tcattaccat | cattaacaac | 1860 |
| acgctgtctg | acattcgccg | tctggtgatg | taa | | | 1893 |

<210> SEQ ID NO 4
<211> LENGTH: 630
<212> TYPE: PRT

<213> ORGANISM: Escherichia coli

<400> SEQUENCE: 4

```
Met Ala Ile Glu Ile Lys Val Pro Asp Ile Gly Ala Asp Glu Val Glu
1               5                   10                  15
Ile Thr Glu Ile Leu Val Lys Val Gly Asp Lys Val Glu Ala Glu Gln
                20                  25                  30
Ser Leu Ile Thr Val Glu Gly Asp Lys Ala Ser Met Glu Val Pro Ser
            35                  40                  45
Pro Gln Ala Gly Ile Val Lys Glu Ile Lys Val Ser Val Gly Asp Lys
        50                  55                  60
Thr Gln Thr Gly Ala Leu Ile Met Ile Phe Asp Ser Ala Asp Gly Ala
65                  70                  75                  80
Ala Asp Ala Ala Pro Ala Gln Ala Glu Glu Lys Lys Glu Ala Ala Pro
                85                  90                  95
Ala Ala Ala Pro Ala Ala Ala Ala Lys Asp Val Asn Val Pro Asp
                100                 105                 110
Ile Gly Ser Asp Glu Val Glu Val Thr Glu Ile Leu Val Lys Val Gly
            115                 120                 125
Asp Lys Val Glu Ala Glu Gln Ser Leu Ile Thr Val Glu Gly Asp Lys
    130                 135                 140
Ala Ser Met Glu Val Pro Ala Pro Phe Ala Gly Thr Val Lys Glu Ile
145                 150                 155                 160
Lys Val Asn Val Gly Asp Lys Val Ser Thr Gly Ser Leu Ile Met Val
                165                 170                 175
Phe Glu Val Ala Gly Glu Ala Gly Ala Ala Ala Pro Ala Ala Lys Gln
            180                 185                 190
Glu Ala Ala Pro Ala Ala Ala Pro Ala Pro Ala Ala Gly Val Lys Glu
        195                 200                 205
Val Asn Val Pro Asp Ile Gly Gly Asp Glu Val Glu Val Thr Glu Val
    210                 215                 220
Met Val Lys Val Gly Asp Lys Val Ala Ala Glu Gln Ser Leu Ile Thr
225                 230                 235                 240
Val Glu Gly Asp Lys Ala Ser Met Glu Val Pro Ala Pro Phe Ala Gly
                245                 250                 255
Val Val Lys Glu Leu Lys Val Asn Val Gly Asp Lys Val Lys Thr Gly
            260                 265                 270
Ser Leu Ile Met Ile Phe Glu Val Glu Gly Ala Ala Pro Ala Ala Ala
        275                 280                 285
Pro Ala Lys Gln Glu Ala Ala Pro Ala Pro Ala Ala Lys Ala Glu
    290                 295                 300
Ala Pro Ala Ala Ala Pro Ala Ala Lys Ala Glu Gly Lys Ser Glu Phe
305                 310                 315                 320
Ala Glu Asn Asp Ala Tyr Val His Ala Thr Pro Leu Ile Arg Arg Leu
                325                 330                 335
Ala Arg Glu Phe Gly Val Asn Leu Ala Lys Val Lys Gly Thr Gly Arg
            340                 345                 350
Lys Gly Arg Ile Leu Arg Glu Asp Val Gln Ala Tyr Val Lys Glu Ala
        355                 360                 365
Ile Lys Arg Ala Glu Ala Ala Pro Ala Ala Thr Gly Gly Gly Ile Pro
    370                 375                 380
Gly Met Leu Pro Trp Pro Lys Val Asp Phe Ser Lys Phe Gly Glu Ile
385                 390                 395                 400
```

```
Glu Glu Val Glu Leu Gly Arg Ile Gln Lys Ile Ser Gly Ala Asn Leu
                405                 410                 415

Ser Arg Asn Trp Val Met Ile Pro His Val Thr His Phe Asp Lys Thr
            420                 425                 430

Asp Ile Thr Glu Leu Glu Ala Phe Arg Lys Gln Gln Asn Glu Glu Ala
        435                 440                 445

Ala Lys Arg Lys Leu Asp Val Lys Ile Thr Pro Val Phe Ile Met
    450                 455                 460

Lys Ala Val Ala Ala Leu Glu Gln Met Pro Arg Phe Asn Ser Ser
465                 470                 475                 480

Leu Ser Glu Asp Gly Gln Arg Leu Thr Leu Lys Lys Tyr Ile Asn Ile
                485                 490                 495

Gly Val Ala Val Asp Thr Pro Asn Gly Leu Val Val Pro Val Phe Lys
            500                 505                 510

Asp Val Asn Lys Lys Gly Ile Ile Glu Leu Ser Arg Glu Leu Met Thr
        515                 520                 525

Ile Ser Lys Lys Ala Arg Asp Gly Lys Leu Thr Ala Gly Glu Met Gln
    530                 535                 540

Gly Gly Cys Phe Thr Ile Ser Ser Ile Gly Gly Leu Gly Thr Thr His
545                 550                 555                 560

Phe Ala Pro Ile Val Asn Ala Pro Glu Val Ala Ile Leu Gly Val Ser
                565                 570                 575

Lys Ser Ala Met Glu Pro Val Trp Asn Gly Lys Glu Phe Val Pro Arg
            580                 585                 590

Leu Met Leu Pro Ile Ser Leu Ser Phe Asp His Arg Val Ile Asp Gly
        595                 600                 605

Ala Asp Gly Ala Arg Phe Ile Thr Ile Ile Asn Asn Thr Leu Ser Asp
    610                 615                 620

Ile Arg Arg Leu Val Met
625                 630

<210> SEQ ID NO 5
<211> LENGTH: 1488
<212> TYPE: DNA
<213> ORGANISM: Escherichia coli

<400> SEQUENCE: 5
gtggataatg gcgtcataa aaaaaacgtc agacccgccg gagataaata tatagaggtc       60
atgatgagta ctgaaatcaa aactcaggtc gtggtacttg gggcaggccc cgcaggttac     120
tccgctgcct tccgttgcgc tgatttaggt ctggaaaccg taatcgtaga acgttacaac     180
actcttggcg tgtttgcct gaacgtcggc tgtatcccctt ctaaagcact gctgcacgta     240
gcaaaagtta tcgaagaagc caaagcgctg gctaacacg gtatcgtctt cggcgaaccg     300
aaaaccgata tcgacaagat tcgtacctgg aaagagaaag taatcaatca gctgaccggt     360
ggtctggctg gtatggcgaa aggccgcaaa gtcaaagtgg tcaacggtct gggtaaattt     420
accggggcta acaccctgga agttgaaggt gagaacggta aaaccgtgat caacttcgac     480
aacgcgatca ttgcagcggg ttctcgcccg attcaactgc cgtttattcc gcatgaagat     540
ccgcgtatct gggactccac tgacgcgctg gaactgaaag aagtaccaga acgcctgctg     600
gtaatgggtg gcggtatcat cggtctggaa atgggcaccg tataccacgc gctgggttca     660
cagattgacg tggttgaaat gttcgaccag gtcatcccgg cagctgataa agacatcgtt     720
aaagtcttta ccaagcgtat cagcaagaaa ttcaacctga tgctggaaac caaagttacc     780
```

-continued

```
gccgttgaag cgaaagaaga cggcatttat gtgacgatgg aaggcaaaaa agcacccgct    840
gaaccgcagc gttacgacgc cgtgctggta gcgattggtc gtgtgccgaa cggtaaaaac    900
ctcgacgcag gcaaagctgg cgtggaagtt gacgaccgtg gtttcatccg cgttgacaaa    960
cagctgcgta ccaacgtacc gcacatcttt gctatcggcg atatcgtcgg tcagccgatg   1020
ctggcacaca aaggtgttca cgaaggtcac gttgccgctg aagttatcgc cggtaagaaa   1080
cactacttcg atccgaaagt tatcccgtcc atcgcctata ccgaaccaga agttgcatgg   1140
gtaggtctga ctgagaaaga agcgaaagag aaaggcatca gctatgaaac cgccaccttc   1200
ccgtgggctg cttctggtcg tgctatcgct tccgactgcg cagacggtat gaccaagctg   1260 atttttcgaca aagaatctca ccgtgtgatc ggtggtgcaa ttgtcggtac taacggtggt   1320
gagctgctgg gtgaaatcgg cctggcaatc gaaatgggtt gtgacgctga agacatcgca   1380
ctgaccatcc atgcgcaccc gactctgcac gagtctgtgg gcctggcggc agaagtgttc   1440
gaaggtagca ttaccgacct gccgaacccg aaagcgaaga agaagtaa                1488
```

<210> SEQ ID NO 6
<211> LENGTH: 495
<212> TYPE: PRT
<213> ORGANISM: Escherichia coli

<400> SEQUENCE: 6

```
Met Asp Asn Gly Arg His Lys Lys Asn Val Arg Pro Ala Gly Asp Lys
1               5                   10                  15

Tyr Ile Glu Val Met Met Ser Thr Glu Ile Lys Thr Gln Val Val
            20                  25                  30

Leu Gly Ala Gly Pro Ala Gly Tyr Ser Ala Ala Phe Arg Cys Ala Asp
            35                  40                  45

Leu Gly Leu Glu Thr Val Ile Val Glu Arg Tyr Asn Thr Leu Gly Gly
        50                  55                  60

Val Cys Leu Asn Val Gly Cys Ile Pro Ser Lys Ala Leu Leu His Val
65                  70                  75                  80

Ala Lys Val Ile Glu Glu Ala Lys Ala Leu Ala Glu His Gly Ile Val
                85                  90                  95

Phe Gly Glu Pro Lys Thr Asp Ile Asp Lys Ile Arg Thr Trp Lys Glu
            100                 105                 110

Lys Val Ile Asn Gln Leu Thr Gly Gly Leu Ala Gly Met Ala Lys Gly
        115                 120                 125

Arg Lys Val Lys Val Val Asn Gly Leu Gly Lys Phe Thr Gly Ala Asn
    130                 135                 140

Thr Leu Glu Val Glu Gly Glu Asn Gly Lys Thr Val Ile Asn Phe Asp
145                 150                 155                 160

Asn Ala Ile Ile Ala Ala Gly Ser Arg Pro Ile Gln Leu Pro Phe Ile
                165                 170                 175

Pro His Glu Asp Pro Arg Ile Trp Asp Ser Thr Asp Ala Leu Glu Leu
            180                 185                 190

Lys Glu Val Pro Glu Arg Leu Leu Val Met Gly Gly Gly Ile Ile Gly
        195                 200                 205

Leu Glu Met Gly Thr Val Tyr His Ala Leu Gly Ser Gln Ile Asp Val
    210                 215                 220

Val Glu Met Phe Asp Gln Val Ile Pro Ala Ala Asp Lys Asp Ile Val
225                 230                 235                 240

Lys Val Phe Thr Lys Arg Ile Ser Lys Lys Phe Asn Leu Met Leu Glu
                245                 250                 255
```

Thr Lys Val Thr Ala Val Glu Ala Lys Glu Asp Gly Ile Tyr Val Thr
            260                 265                 270
Met Glu Gly Lys Lys Ala Pro Ala Glu Pro Gln Arg Tyr Asp Ala Val
        275                 280                 285
Leu Val Ala Ile Gly Arg Val Pro Asn Gly Lys Asn Leu Asp Ala Gly
        290                 295                 300
Lys Ala Gly Val Glu Val Asp Asp Arg Gly Phe Ile Arg Val Asp Lys
305                 310                 315                 320
Gln Leu Arg Thr Asn Val Pro His Ile Phe Ala Ile Gly Asp Ile Val
                325                 330                 335
Gly Gln Pro Met Leu Ala His Lys Gly Val His Glu Gly His Val Ala
            340                 345                 350
Ala Glu Val Ile Ala Gly Lys Lys His Tyr Phe Asp Pro Lys Val Ile
        355                 360                 365
Pro Ser Ile Ala Tyr Thr Glu Pro Glu Val Ala Trp Val Gly Leu Thr
    370                 375                 380
Glu Lys Glu Ala Lys Glu Lys Gly Ile Ser Tyr Glu Thr Ala Thr Phe
385                 390                 395                 400
Pro Trp Ala Ala Ser Gly Arg Ala Ile Ala Ser Asp Cys Ala Asp Gly
                405                 410                 415
Met Thr Lys Leu Ile Phe Asp Lys Glu Ser His Arg Val Ile Gly Gly
            420                 425                 430
Ala Ile Val Gly Thr Asn Gly Gly Glu Leu Leu Gly Glu Ile Gly Leu
        435                 440                 445
Ala Ile Glu Met Gly Cys Asp Ala Glu Asp Ile Ala Leu Thr Ile His
        450                 455                 460
Ala His Pro Thr Leu His Glu Ser Val Gly Leu Ala Ala Glu Val Phe
465                 470                 475                 480
Glu Gly Ser Ile Thr Asp Leu Pro Asn Pro Lys Ala Lys Lys Lys
                485                 490                 495

<210> SEQ ID NO 7
<211> LENGTH: 2802
<212> TYPE: DNA
<213> ORGANISM: Escherichia coli

<400> SEQUENCE: 7
atgcagaaca gcgctttgaa agcctggttg gactcttctt acctctctgg cgcaaaccag    60
agctggatag aacagctcta tgaagacttc ttaaccgatc ctgactcggt tgacgctaac   120
tggcgttcga cgttccagca gttacctggt acgggagtca aaccggatca attccactct   180
caaacgcgtg aatatttccg ccgcctggcg aaagacgctt cacgttactc ttcaacgatc   240
tccgaccctg acaccaatgt gaagcaggtt aaagtcctgc agctcattaa cgcataccgc   300
ttccgtggtc accagcatgc gaatctcgat ccgctgggac tgtggcagca agataaagtg   360
gccgatctgg atccgtcttt ccacgatctg accgaagcag acttccagga gaccttcaac   420
gtcggttcat tgccagcgg caaagaaacc atgaaactcg gcgagctgct ggaagccctc   480
aagcaaacct actgcggccc gattggtgcc gagtatatgc acattaccag caccgaagaa   540
aaacgctgga tccaacagcg tatcgagtct ggtcgcgcga ctttcaatag cgaagagaaa   600
aaacgcttct taagcgaact gaccgccgct gaaggtcttg aacgttacct cggcgcaaaa   660
ttccctggcg caaacgcttt ctcgctggaa ggcggtgacg cgttaatccc gatgcttaaa   720
gagatgatcc gccacgctgg caacagcggc acccgcgaag tggttctcgg gatggcgcac   780

```
cgtggtcgtc tgaacgtgct ggtgaacgtg ctgggtaaaa aaccgcaaga cttgttcgac    840
gagttcgccg gtaaacataa agaacacctc ggcacgggtg acgtgaaata ccacatgggc    900
ttctcgtctg acttccagac cgatggcggc ctggtgcacc tggcgctggc gtttaacccg    960
tctcaccttg agattgtaag cccggtagtt atcggtctg ttcgtgcccg ctggacaga    1020
cttgatgagc cgagcagcaa caaagtgctg ccaatcacca tccacggtga cgccgcagtg   1080
accgggcagg cgtggttca ggaaaccctg aacatgtcga agcgcgtgg ttatgaagtt     1140
ggcggtacgg tacgtatcgt tatcaacaac caggttggtt tcaccacctc taatccgctg   1200
gatgcccgtt ctacgccgta ctgtactgat atcggtaaga tggttcaggc cccgattttc   1260
cacgttaacg cggacgatcc ggaagccgtt gcctttgtga cccgtctggc gctcgatttc   1320
cgtaacacct ttaaacgtga tgtcttcatc gacctggtgt gctaccgccg tcacggccac   1380
aacgaagccg acgagccgag cgcaacccag ccgctgatgt atcagaaaat caaaaaacat   1440
ccgacaccgc gcaaaatcta cgctgacaag ctggagcagg aaaaagtggc gacgctggaa   1500
gatgccaccg agatggttaa cctgtaccgc gatgcgctgg atgctggcga ttgcgtagtg   1560
gcagagtggc gtccgatgaa catgcactct ttcacctggt cgccgtacct caaccacgaa   1620
tgggacgaag agtacccgaa caaagttgag atgaagcgcc tgcaggagct ggcgaaacgc   1680
atcagcacg tgccggaagc agttgaaatg cagtctcgcg ttgccaagat ttatggcgat    1740
cgccaggcga tggctgccgg tgagaaactg ttcgactggg gcggtgcgga aaacctcgct   1800
tacgccacgc tggttgatga aggcattccg gttcgcctgt cgggtgaaga ctccggtcgc   1860
ggtaccttct tccaccgcca cgcggtgatc cacaaccagt ctaacggttc cacttacacg   1920
ccgctgcaac atatccataa cgggcagggc gcgttccgtg tctgggactc cgtactgtct   1980
gaagaagcag tgctggcgtt tgaatatggt tatgccaccg cagaaccacg cactctgacc   2040
atctgggaag cgcagttcgg tgacttcgcc aacggtgcgc aggtggttat cgaccagttc   2100
atctcctctg gcgaacagaa atggggccgg atgtgtggtc tggtgatgtt gctgccgcac   2160
ggttacgaag ggcagggggcc ggagcactcc tccgcgcgtc tggaacgtta tctgcaactt   2220
tgtgctgagc aaaacatgca ggtttgcgta ccgtctaccc cggcacaggt ttaccacatg   2280
ctgcgtcgtc aggcgctgcg cgggatgcgt cgtccgctgg tcgtgatgtc gccgaaatcc   2340
ctgctgcgtc atccgctggc ggtttccagc ctcgaagaac tggcgaacgg caccttcctg   2400
ccagccatcg gtgaaatcga cgagcttgat ccgaagggcg tgaagcgcgt agtgatgtgt   2460
tctggtaagg tttattacga cctgctggaa cagcgtcgta agaacaatca acacgatgtc   2520
gccattgtgc gtatcgagca actctacccg ttcccgcata aagcgatgca ggaagtgttg   2580
cagcagtttg ctcacgtcaa ggattttgtc tggtgccagg aagagccgct caaccagggc   2640
gcatggtact gcagccagca tcatttccgt gaagtgattc cgtttggggc ttctctgcgt   2700
tatgcaggcc gccggcctc cgcctctccg gcggtagggt atatgtccgt tcaccagaaa   2760
cagcaacaag atctggttaa tgacgcgctg aacgtcgaat aa                       2802
```

<210> SEQ ID NO 8
<211> LENGTH: 933
<212> TYPE: PRT
<213> ORGANISM: Escherichia coli

<400> SEQUENCE: 8

Met Gln Asn Ser Ala Leu Lys Ala Trp Leu Asp Ser Ser Tyr Leu Ser
1               5                   10                  15

Gly Ala Asn Gln Ser Trp Ile Glu Gln Leu Tyr Glu Asp Phe Leu Thr
            20                  25                  30

Asp Pro Asp Ser Val Asp Ala Asn Trp Arg Ser Thr Phe Gln Gln Leu
        35                  40                  45

Pro Gly Thr Gly Val Lys Pro Asp Gln Phe His Ser Gln Thr Arg Glu
    50                  55                  60

Tyr Phe Arg Arg Leu Ala Lys Asp Ala Ser Arg Tyr Ser Ser Thr Ile
65                  70                  75                  80

Ser Asp Pro Asp Thr Asn Val Lys Gln Val Lys Val Leu Gln Leu Ile
                85                  90                  95

Asn Ala Tyr Arg Phe Arg Gly His Gln His Ala Asn Leu Asp Pro Leu
            100                 105                 110

Gly Leu Trp Gln Gln Asp Lys Val Ala Asp Leu Asp Pro Ser Phe His
        115                 120                 125

Asp Leu Thr Glu Ala Asp Phe Gln Glu Thr Phe Asn Val Gly Ser Phe
    130                 135                 140

Ala Ser Gly Lys Glu Thr Met Lys Leu Gly Glu Leu Leu Glu Ala Leu
145                 150                 155                 160

Lys Gln Thr Tyr Cys Gly Pro Ile Gly Ala Glu Tyr Met His Ile Thr
                165                 170                 175

Ser Thr Glu Glu Lys Arg Trp Ile Gln Gln Arg Ile Glu Ser Gly Arg
            180                 185                 190

Ala Thr Phe Asn Ser Glu Glu Lys Lys Arg Phe Leu Ser Glu Leu Thr
        195                 200                 205

Ala Ala Glu Gly Leu Glu Arg Tyr Leu Gly Ala Lys Phe Pro Gly Ala
    210                 215                 220

Lys Arg Phe Ser Leu Glu Gly Gly Asp Ala Leu Ile Pro Met Leu Lys
225                 230                 235                 240

Glu Met Ile Arg His Ala Gly Asn Ser Gly Thr Arg Glu Val Val Leu
                245                 250                 255

Gly Met Ala His Arg Gly Arg Leu Asn Val Leu Val Asn Val Leu Gly
            260                 265                 270

Lys Lys Pro Gln Asp Leu Phe Asp Glu Phe Ala Gly Lys His Lys Glu
        275                 280                 285

His Leu Gly Thr Gly Asp Val Lys Tyr His Met Gly Phe Ser Ser Asp
    290                 295                 300

Phe Gln Thr Asp Gly Gly Leu Val His Leu Ala Leu Ala Phe Asn Pro
305                 310                 315                 320

Ser His Leu Glu Ile Val Ser Pro Val Val Ile Gly Ser Val Arg Ala
                325                 330                 335

Arg Leu Asp Arg Leu Asp Glu Pro Ser Ser Asn Lys Val Leu Pro Ile
            340                 345                 350

Thr Ile His Gly Asp Ala Ala Val Thr Gly Gln Gly Val Val Gln Glu
        355                 360                 365

Thr Leu Asn Met Ser Lys Ala Arg Gly Tyr Glu Val Gly Gly Thr Val
    370                 375                 380

Arg Ile Val Ile Asn Asn Gln Val Gly Phe Thr Thr Ser Asn Pro Leu
385                 390                 395                 400

Asp Ala Arg Ser Thr Pro Tyr Cys Thr Asp Ile Gly Lys Met Val Gln
                405                 410                 415

Ala Pro Ile Phe His Val Asn Ala Asp Asp Pro Glu Ala Val Ala Phe
            420                 425                 430

```
Val Thr Arg Leu Ala Leu Asp Phe Arg Asn Thr Phe Lys Arg Asp Val
            435                 440                 445

Phe Ile Asp Leu Val Cys Tyr Arg Arg His Gly His Asn Glu Ala Asp
    450                 455                 460

Glu Pro Ser Ala Thr Gln Pro Leu Met Tyr Gln Lys Ile Lys Lys His
465                 470                 475                 480

Pro Thr Pro Arg Lys Ile Tyr Ala Asp Lys Leu Glu Gln Glu Lys Val
                485                 490                 495

Ala Thr Leu Glu Asp Ala Thr Glu Met Val Asn Leu Tyr Arg Asp Ala
            500                 505                 510

Leu Asp Ala Gly Asp Cys Val Val Ala Glu Trp Arg Pro Met Asn Met
    515                 520                 525

His Ser Phe Thr Trp Ser Pro Tyr Leu Asn His Glu Trp Asp Glu Glu
530                 535                 540

Tyr Pro Asn Lys Val Glu Met Lys Arg Leu Gln Glu Leu Ala Lys Arg
545                 550                 555                 560

Ile Ser Thr Val Pro Glu Ala Val Glu Met Gln Ser Arg Val Ala Lys
                565                 570                 575

Ile Tyr Gly Asp Arg Gln Ala Met Ala Ala Gly Glu Lys Leu Phe Asp
            580                 585                 590

Trp Gly Gly Ala Glu Asn Leu Ala Tyr Ala Thr Leu Val Asp Glu Gly
    595                 600                 605

Ile Pro Val Arg Leu Ser Gly Glu Asp Ser Gly Arg Gly Thr Phe Phe
610                 615                 620

His Arg His Ala Val Ile His Asn Gln Ser Asn Gly Ser Thr Tyr Thr
625                 630                 635                 640

Pro Leu Gln His Ile His Asn Gly Gln Gly Ala Phe Arg Val Trp Asp
                645                 650                 655

Ser Val Leu Ser Glu Glu Ala Val Leu Ala Phe Glu Tyr Gly Tyr Ala
            660                 665                 670

Thr Ala Glu Pro Arg Thr Leu Thr Ile Trp Glu Ala Gln Phe Gly Asp
    675                 680                 685

Phe Ala Asn Gly Ala Gln Val Val Ile Asp Gln Phe Ile Ser Ser Gly
690                 695                 700

Glu Gln Lys Trp Gly Arg Met Cys Gly Leu Val Met Leu Leu Pro His
705                 710                 715                 720

Gly Tyr Glu Gly Gln Gly Pro Glu His Ser Ser Ala Arg Leu Glu Arg
                725                 730                 735

Tyr Leu Gln Leu Cys Ala Glu Gln Asn Met Gln Val Cys Val Pro Ser
            740                 745                 750

Thr Pro Ala Gln Val Tyr His Met Leu Arg Arg Gln Ala Leu Arg Gly
    755                 760                 765

Met Arg Arg Pro Leu Val Val Met Ser Pro Lys Ser Leu Leu Arg His
770                 775                 780

Pro Leu Ala Val Ser Ser Leu Glu Glu Leu Ala Asn Gly Thr Phe Leu
785                 790                 795                 800

Pro Ala Ile Gly Glu Ile Asp Glu Leu Asp Pro Lys Gly Val Lys Arg
                805                 810                 815

Val Val Met Cys Ser Gly Lys Val Tyr Tyr Asp Leu Leu Glu Gln Arg
            820                 825                 830

Arg Lys Asn Asn Gln His Asp Val Ala Ile Val Arg Ile Glu Gln Leu
    835                 840                 845

Tyr Pro Phe Pro His Lys Ala Met Gln Glu Val Leu Gln Gln Phe Ala
```

|  |  |  | 850 |  |  |  | 855 |  |  |  | 860 |  |
|---|---|---|---|---|---|---|---|---|---|---|---|---|

His Val Lys Asp Phe Val Trp Cys Gln Glu Glu Pro Leu Asn Gln Gly
865                         870                     875                     880

Ala Trp Tyr Cys Ser Gln His His Phe Arg Glu Val Ile Pro Phe Gly
                          885                     890                         895

Ala Ser Leu Arg Tyr Ala Gly Arg Pro Ala Ser Ala Ser Pro Ala Val
            900                     905                     910

Gly Tyr Met Ser Val His Gln Lys Gln Gln Gln Asp Leu Val Asn Asp
        915                     920                     925

Ala Leu Asn Val Glu
    930

<210> SEQ ID NO 9
<211> LENGTH: 1218
<212> TYPE: DNA
<213> ORGANISM: Escherichia coli

<400> SEQUENCE: 9

```
atgagtagcg tagatattct ggtccctgac ctgcctgaat ccgtagccga tgccaccgtc      60
gcaacctggc ataaaaaacc cggcgacgca gtcgtacgtg atgaagtgct ggtagaaatc     120
gaaactgaca aagtggtact ggaagtaccg gcatcagcag acggcattct ggatgcggtt     180
ctggaagatg aagtacaac ggtaacgtct cgtcagatcc ttggtcgcct gcgtgaaggc     240
aacagcgccg gtaaagaaac cagcgccaaa tctgaagaga aagcgtccac tccggcgcaa     300
cgccagcagg cgtctctgga gagcaaaaac aacgatgcgt taagcccggc gatccgtcgc     360
ctgctggctg aacacaatct cgacgccagc gccattaaag gcaccggtgt gggtggtcgt     420
ctgactcgtg aagatgtgga aaacatctg gcgaaagccc cggcgaaaga gtctgctccg     480
gcagcggctg ctccggcggc gcaaccggct ctggctgcac gtagtgaaaa acgtgtcccg     540
atgactcgcc tgcgtaagcg tgtggcagag cgtctgctgg aagcgaaaaa ctccaccgcc     600
atgctgacca cgttcaacga agtcaacatg aagccgatta tggatctgcg taagcagtac     660
ggtgaagcgt ttgaaaaacg ccacggcatc cgtctgggct ttatgtcctt ctacgtgaaa     720
gcggtggttg aagccctgaa acgttacccg gaagtgaacg cttctatcga cggcgatgac     780
gtggtttacc acaactattt cgacgtcagc atggcggttt ctacgccgcg cggcctggtg     840
acgccggttc tgcgtgatgt cgatacccctc ggcatggcag acatcgagaa gaaaatcaaa     900
gagctggcag tcaaaggccg tgacggcaag ctgaccgttg aagatctgac cggtggtaac     960
ttcaccatca ccaacggtgg tgtgttcggt tccctgatgt ctacgccgat catcaacccg    1020
ccgcagagcg caattctggg tatgcacgct atcaaagatc gtccgatggc ggtgaatggt    1080
caggttgaga tcctgccgat gatgtacctg gcgctgtcct acgatcaccg tctgatcgat    1140
ggtcgcgaat ccgtgggctt cctggtaacg atcaaagagt tgctggaaga tccgacgcgt    1200
ctgctgctgg acgtgtag                                                  1218
```

<210> SEQ ID NO 10
<211> LENGTH: 405
<212> TYPE: PRT
<213> ORGANISM: Escherichia coli

<400> SEQUENCE: 10

Met Ser Ser Val Asp Ile Leu Val Pro Asp Leu Pro Glu Ser Val Ala
1                 5                     10                     15

Asp Ala Thr Val Ala Thr Trp His Lys Lys Pro Gly Asp Ala Val Val

```
                    20                  25                  30
Arg Asp Glu Val Leu Val Glu Ile Glu Thr Asp Lys Val Leu Glu
                35                  40                  45

Val Pro Ala Ser Ala Asp Gly Ile Leu Asp Ala Val Leu Glu Asp Glu
 50                  55                  60

Gly Thr Thr Val Thr Ser Arg Gln Ile Leu Gly Arg Leu Arg Glu Gly
 65                  70                  75                  80

Asn Ser Ala Gly Lys Glu Thr Ser Ala Lys Ser Glu Glu Lys Ala Ser
                 85                  90                  95

Thr Pro Ala Gln Arg Gln Gln Ala Ser Leu Glu Glu Gln Asn Asn Asp
                100                 105                 110

Ala Leu Ser Pro Ala Ile Arg Leu Leu Ala Glu His Asn Leu Asp
            115                 120                 125

Ala Ser Ala Ile Lys Gly Thr Gly Val Gly Gly Arg Leu Thr Arg Glu
            130                 135                 140

Asp Val Glu Lys His Leu Ala Lys Ala Pro Ala Lys Glu Ser Ala Pro
145                 150                 155                 160

Ala Ala Ala Ala Pro Ala Ala Gln Pro Ala Leu Ala Ala Arg Ser Glu
                165                 170                 175

Lys Arg Val Pro Met Thr Arg Leu Arg Lys Arg Val Ala Glu Arg Leu
                180                 185                 190

Leu Glu Ala Lys Asn Ser Thr Ala Met Leu Thr Thr Phe Asn Glu Val
            195                 200                 205

Asn Met Lys Pro Ile Met Asp Leu Arg Lys Gln Tyr Gly Glu Ala Phe
            210                 215                 220

Glu Lys Arg His Gly Ile Arg Leu Gly Phe Met Ser Phe Tyr Val Lys
225                 230                 235                 240

Ala Val Val Glu Ala Leu Lys Arg Tyr Pro Glu Val Asn Ala Ser Ile
                245                 250                 255

Asp Gly Asp Asp Val Val Tyr His Asn Tyr Phe Asp Val Ser Met Ala
            260                 265                 270

Val Ser Thr Pro Arg Gly Leu Val Thr Pro Val Leu Arg Asp Val Asp
            275                 280                 285

Thr Leu Gly Met Ala Asp Ile Glu Lys Lys Ile Lys Glu Leu Ala Val
            290                 295                 300

Lys Gly Arg Asp Gly Lys Leu Thr Val Glu Asp Leu Thr Gly Gly Asn
305                 310                 315                 320

Phe Thr Ile Thr Asn Gly Gly Val Phe Gly Ser Leu Met Ser Thr Pro
                325                 330                 335

Ile Ile Asn Pro Pro Gln Ser Ala Ile Leu Gly Met His Ala Ile Lys
            340                 345                 350

Asp Arg Pro Met Ala Val Asn Gly Gln Val Glu Ile Leu Pro Met Met
            355                 360                 365

Tyr Leu Ala Leu Ser Tyr Asp His Arg Leu Ile Asp Gly Arg Glu Ser
            370                 375                 380

Val Gly Phe Leu Val Thr Ile Lys Glu Leu Leu Glu Asp Pro Thr Arg
385                 390                 395                 400

Leu Leu Leu Asp Val
                405

<210> SEQ ID NO 11
<211> LENGTH: 2145
<212> TYPE: DNA
<213> ORGANISM: Escherichia coli
```

<400> SEQUENCE: 11

```
gtgtcccgta ttattatgct gatccctacc ggaaccagcg tcggtctgac cagcgtcagc      60
cttggcgtga tccgtgcaat ggaacgcaaa ggcgttcgtc tgagcgtttt caaacctatc     120
gctcagccgc gtaccggtgg cgatgcgccc gatcagacta cgactatcgt gcgtgcgaac     180
tcttccacca cgacggccgc tgaaccgctg aaaatgagct acgttgaagg tctgctttcc     240
agcaatcaga aagatgtgct gatggaagag atcatcgcga actaccacgc taacaccaaa     300
gacgctgaag tcgttctggt ggaaggtctg gtcccgacac gtaagcacca gtttgcccag     360
tctctgaact acgaaatcgc caaaacgctg aacgcagaaa tcgtcttcgt tatgtctcag     420
ggcactgata ctccggaaca gttgaaagag cgtatcgaac tgactcgcaa cagcttcggc     480
ggtgcaaaaa acaccaatat taccggcgtt atcgttaaca aactgaacgc tccggttgat     540
gagcagggtc gtacccgtcc ggatctgtcc gagattttg acgactccac caaagcaaaa     600
gtgaacaacg ttgatccggc gaagctgcaa gaatccagcc cgctgccggt tctcggcgct     660
gtgccgtgga gctttgacct gatcgcgact cgtgcgatcg atatggctcg ccacctgaat     720
gcgaccatca tcaacgaagg cgacatcaat actcgccgcg ttaaatccgt cactttctgc     780
gcacgcagca ttccgcacat gctggagcac ttccgtgccg gttctctgct ggtgacttcc     840
gcagaccgcc ctgacgtgct ggttgccgct gcctggctg ccatgaacgg cgtagaaatc     900
ggtgccctgc tgctgactgg cggctacgaa atggacgcgc gcatttctaa actgtgcgaa     960
cgtgctttcg ctactggcct gccggtattt atggtgaaca ccaacacctg gcagacttct    1020
cttagcctgc agagcttcaa cctggaagtt ccggttgacg atcatgagcg tatcgaaaaa    1080
gttcaggaat acgtggctaa ctacatcaac gctgactgga tcgattctct gactgccact    1140
tctgagcgca gccgtcgtct gtctccgcca gcgttccgtt atcagctgac tgaacttgcg    1200
cgcaaagcgg gcaaacgtat cgttctgccg gaaggtgacg aaccgcgtac cgttaaagca    1260
gccgctatct gtgctgaacg tggtatcgca acttgcgtac tgctgggtaa tccggcagag    1320
atcaaccgtg ttgcagcctc tcagggtgta gaactgggtg caggcattga aatcgttgat    1380
ccagaagtgg ttcgcgaaaa ctatgttggt cgtctggtcg aactgcgtaa gaacaaaggc    1440
atgaccgaaa ccgttgcccg cgaacagctg gaagacaacg tggttctcgg tacgctgatg    1500
ctggaacaag atgaagttga tggtctggtt tccgtgctgc ttcacaccac cgcaaacacc    1560
atccgtccgc cgctgcagct gatcaaaact gcaccgggca gctccctggt atcttccgtg    1620
ttcttcatgc tgttgccgga acaggtttac gtttacggtg actgtgcgat caacccggat    1680
ccgaccgcag aacagctggc agaaatcgcg attcagtccg ctgattccgc tgcggccttc    1740
ggtatcgaac cgcgcgttgc tatgctctcc tactccaccg gtacttctgg tgctggtagc    1800
gacgtagaaa aagttcgcga agcaactcgt ctggcgcagg aaaaacgtcc tgatctgatg    1860
atcgacggtc cgctgcagta cgacgctgcg gtaatgctga cgttgcgaa atccaaagca    1920
ccgaactctc cggttgcagg tcgcgctacc gtgttcatct tcccggatct gaacaccggt    1980
aacaccacct acaaagcggt acagcgttct gctgacctga tctctatcgg accgatgctg    2040
cagggtatgc gcaagccggt taacgacctg tcccgtggcg cactggttga tgatatcgtc    2100
tacaccatcg cgctgactgc gattcagtct gcacagcagc agtaa                    2145
```

<210> SEQ ID NO 12
<211> LENGTH: 714
<212> TYPE: PRT

<213> ORGANISM: Escherichia coli

<400> SEQUENCE: 12

```
Met Ser Arg Ile Ile Met Leu Ile Pro Thr Gly Thr Ser Val Gly Leu
  1               5                  10                  15

Thr Ser Val Ser Leu Gly Val Ile Arg Ala Met Glu Arg Lys Gly Val
             20                  25                  30

Arg Leu Ser Val Phe Lys Pro Ile Ala Gln Pro Arg Thr Gly Gly Asp
         35                  40                  45

Ala Pro Asp Gln Thr Thr Thr Ile Val Arg Ala Asn Ser Ser Thr Thr
 50                  55                  60

Thr Ala Ala Glu Pro Leu Lys Met Ser Tyr Val Glu Gly Leu Leu Ser
 65                  70                  75                  80

Ser Asn Gln Lys Asp Val Leu Met Glu Glu Ile Ile Ala Asn Tyr His
                 85                  90                  95

Ala Asn Thr Lys Asp Ala Glu Val Val Leu Val Glu Gly Leu Val Pro
            100                 105                 110

Thr Arg Lys His Gln Phe Ala Gln Ser Leu Asn Tyr Glu Ile Ala Lys
        115                 120                 125

Thr Leu Asn Ala Glu Ile Val Phe Val Met Ser Gln Gly Thr Asp Thr
130                 135                 140

Pro Glu Gln Leu Lys Glu Arg Ile Glu Leu Thr Arg Asn Ser Phe Gly
145                 150                 155                 160

Gly Ala Lys Asn Thr Asn Ile Thr Gly Val Ile Val Asn Lys Leu Asn
                165                 170                 175

Ala Pro Val Asp Glu Gln Gly Arg Thr Arg Pro Asp Leu Ser Glu Ile
            180                 185                 190

Phe Asp Asp Ser Thr Lys Ala Lys Val Asn Asn Val Asp Pro Ala Lys
        195                 200                 205

Leu Gln Glu Ser Ser Pro Leu Pro Val Leu Gly Ala Val Pro Trp Ser
210                 215                 220

Phe Asp Leu Ile Ala Thr Arg Ala Ile Asp Met Ala Arg His Leu Asn
225                 230                 235                 240

Ala Thr Ile Ile Asn Glu Gly Asp Ile Asn Thr Arg Arg Val Lys Ser
                245                 250                 255

Val Thr Phe Cys Ala Arg Ser Ile Pro His Met Leu Glu His Phe Arg
            260                 265                 270

Ala Gly Ser Leu Leu Val Thr Ser Ala Asp Arg Pro Asp Val Leu Val
        275                 280                 285

Ala Ala Cys Leu Ala Ala Met Asn Gly Val Glu Ile Gly Ala Leu Leu
290                 295                 300

Leu Thr Gly Gly Tyr Glu Met Asp Ala Arg Ile Ser Lys Leu Cys Glu
305                 310                 315                 320

Arg Ala Phe Ala Thr Gly Leu Pro Val Phe Met Val Asn Thr Asn Thr
                325                 330                 335

Trp Gln Thr Ser Leu Ser Leu Gln Ser Phe Asn Leu Glu Val Pro Val
            340                 345                 350

Asp Asp His Glu Arg Ile Glu Lys Val Gln Glu Tyr Val Ala Asn Tyr
        355                 360                 365

Ile Asn Ala Asp Trp Ile Asp Ser Leu Thr Ala Thr Ser Glu Arg Ser
370                 375                 380

Arg Arg Leu Ser Pro Pro Ala Phe Arg Tyr Gln Leu Thr Glu Leu Ala
385                 390                 395                 400
```

Arg Lys Ala Gly Lys Arg Ile Val Leu Pro Glu Gly Asp Glu Pro Arg
            405                 410                 415

Thr Val Lys Ala Ala Ile Cys Ala Glu Arg Gly Ile Ala Thr Cys
            420                 425                 430

Val Leu Leu Gly Asn Pro Ala Glu Ile Asn Arg Val Ala Ala Ser Gln
            435                 440                 445

Gly Val Glu Leu Gly Ala Gly Ile Glu Ile Val Asp Pro Glu Val Val
450                 455                 460

Arg Glu Asn Tyr Val Arg Leu Val Glu Leu Arg Lys Asn Lys Gly
465                 470                 475                 480

Met Thr Glu Thr Val Ala Arg Glu Gln Leu Glu Asp Asn Val Val Leu
            485                 490                 495

Gly Thr Leu Met Leu Glu Gln Asp Glu Val Asp Gly Leu Val Ser Gly
            500                 505                 510

Ala Val His Thr Thr Ala Asn Thr Ile Arg Pro Pro Leu Gln Leu Ile
            515                 520                 525

Lys Thr Ala Pro Gly Ser Ser Leu Val Ser Ser Val Phe Phe Met Leu
            530                 535                 540

Leu Pro Glu Gln Val Tyr Val Tyr Gly Asp Cys Ala Ile Asn Pro Asp
545                 550                 555                 560

Pro Thr Ala Glu Gln Leu Ala Glu Ile Ala Ile Gln Ser Ala Asp Ser
            565                 570                 575

Ala Ala Ala Phe Gly Ile Glu Pro Arg Val Ala Met Leu Ser Tyr Ser
            580                 585                 590

Thr Gly Thr Ser Gly Ala Gly Ser Asp Val Glu Lys Val Arg Glu Ala
            595                 600                 605

Thr Arg Leu Ala Gln Glu Lys Arg Pro Asp Leu Met Ile Asp Gly Pro
            610                 615                 620

Leu Gln Tyr Asp Ala Ala Val Met Ala Asp Val Ala Lys Ser Lys Ala
625                 630                 635                 640

Pro Asn Ser Pro Val Ala Gly Arg Ala Thr Val Phe Ile Phe Pro Asp
            645                 650                 655

Leu Asn Thr Gly Asn Thr Thr Tyr Lys Ala Val Gln Arg Ser Ala Asp
            660                 665                 670

Leu Ile Ser Ile Gly Pro Met Leu Gln Gly Met Arg Lys Pro Val Asn
            675                 680                 685

Asp Leu Ser Arg Gly Ala Leu Val Asp Asp Ile Val Tyr Thr Ile Ala
            690                 695                 700

Leu Thr Ala Ile Gln Ser Ala Gln Gln Gln
705                 710

<210> SEQ ID NO 13
<211> LENGTH: 1203
<212> TYPE: DNA
<213> ORGANISM: Escherichia coli

<400> SEQUENCE: 13
atgtcgagta agttagtact ggttctgaac tgcggtagtt cttcactgaa atttgccatc    60
atcgatgcag taatggtga agagtacctt tctggtttag ccgaatgttt ccacctgccc    120
gaagcacgta tcaaatggaa aatggacggc aataaacagg aagcggcttt aggtgcaggc    180
gccgctcaca gcgaagcgct caactttatc gttaatacta ttctggcaca aaaaccagaa    240
ctgtctgcgc agctgactgc tatcggtcac cgtatcgtac acggcggcga aaagtatacc    300
agctccgtag tgatcgatga gtctgttatt cagggtatca agatgcagc ttcttttgca    360

```
ccgctgcaca acccggctca cctgatcggt atcgaagaag ctctgaaatc tttcccacag    420
ctgaaagaca aaacgttgc tgtatttgac accgcgttcc accagactat gccggaagag    480
tcttacctct acgccctgcc ttacaacctg tacaaagagc acggcatccg tcgttacggc    540
gcgcacggca ccagccactt ctatgtaacc caggaagcgg caaaaatgct gaacaaaccg    600
gtagaagaac tgaacatcat cacctgccac ctgggcaacg gtggttccgt ttctgctatc    660
cgcaacggta atgcgttga cacctctatg ggcctgaccc cgctggaagg tctggtcatg    720
ggtacccgtt ctggtgatat cgatccggcg atcatcttcc acctgcacga caccctgggc    780
atgagcgttg acgcaatcaa caaactgctg accaaagagt ctggcctgct gggtctgacc    840
gaagtgacca gcgactgccg ctatgttgaa gacaactacg cgacgaaaga agacgcgaag    900
cgcgcaatgg acgtttactg ccaccgcctg gcgaaataca tcggtgccta cactgcgctg    960
atggatggtc gtctggacgc tgttgtattc actggtggta tcggtgaaaa tgccgcaatg    1020
gttcgtgaac tgtctctggg caaactgggc gtgctgggct ttgaagttga tcatgaacgc    1080
aacctggctg cacgtttcgg caaatctggt ttcatcaaca agaaggtac ccgtcctgcg    1140 gtggttatcc caaccaacga agaactggtt atcgcgcaag acgcgagccg cctgactgcc    1200
tga                                                                  1203
```

<210> SEQ ID NO 14
<211> LENGTH: 400
<212> TYPE: PRT
<213> ORGANISM: Escherichia coli

<400> SEQUENCE: 14

```
Met Ser Ser Lys Leu Val Leu Val Leu Asn Cys Gly Ser Ser Ser Leu
1               5                   10                  15

Lys Phe Ala Ile Ile Asp Ala Val Asn Gly Glu Glu Tyr Leu Ser Gly
            20                  25                  30

Leu Ala Glu Cys Phe His Leu Pro Glu Ala Arg Ile Lys Trp Lys Met
        35                  40                  45

Asp Gly Asn Lys Gln Glu Ala Ala Leu Gly Ala Gly Ala Ala His Ser
    50                  55                  60

Glu Ala Leu Asn Phe Ile Val Asn Thr Ile Leu Ala Gln Lys Pro Glu
65                  70                  75                  80

Leu Ser Ala Gln Leu Thr Ala Ile Gly His Arg Ile Val His Gly Gly
                85                  90                  95

Glu Lys Tyr Thr Ser Ser Val Val Ile Asp Glu Ser Val Ile Gln Gly
            100                 105                 110

Ile Lys Asp Ala Ala Ser Phe Ala Pro Leu His Asn Pro Ala His Leu
        115                 120                 125

Ile Gly Ile Glu Glu Ala Leu Lys Ser Phe Pro Gln Leu Lys Asp Lys
    130                 135                 140

Asn Val Ala Val Phe Asp Thr Ala Phe His Gln Thr Met Pro Glu Glu
145                 150                 155                 160

Ser Tyr Leu Tyr Ala Leu Pro Tyr Asn Leu Tyr Lys Glu His Gly Ile
                165                 170                 175

Arg Arg Tyr Gly Ala His Gly Thr Ser His Phe Tyr Val Thr Gln Glu
            180                 185                 190

Ala Ala Lys Met Leu Asn Lys Pro Val Glu Glu Leu Asn Ile Ile Thr
        195                 200                 205

Cys His Leu Gly Asn Gly Gly Ser Val Ser Ala Ile Arg Asn Gly Lys
```

```
            210                 215                 220
Cys Val Asp Thr Ser Met Gly Leu Thr Pro Leu Glu Gly Leu Val Met
225                 230                 235                 240

Gly Thr Arg Ser Gly Asp Ile Asp Pro Ala Ile Ile Phe His Leu His
            245                 250                 255

Asp Thr Leu Gly Met Ser Val Asp Ala Ile Asn Lys Leu Leu Thr Lys
                260                 265                 270

Glu Ser Gly Leu Leu Gly Leu Thr Glu Val Thr Ser Asp Cys Arg Tyr
            275                 280                 285

Val Glu Asp Asn Tyr Ala Thr Lys Glu Asp Ala Lys Arg Ala Met Asp
            290                 295                 300

Val Tyr Cys His Arg Leu Ala Lys Tyr Ile Gly Ala Tyr Thr Ala Leu
305                 310                 315                 320

Met Asp Gly Arg Leu Asp Ala Val Val Phe Thr Gly Gly Ile Gly Glu
                325                 330                 335

Asn Ala Ala Met Val Arg Glu Leu Ser Leu Gly Lys Leu Gly Val Leu
                340                 345                 350

Gly Phe Glu Val Asp His Glu Arg Asn Leu Ala Ala Arg Phe Gly Lys
            355                 360                 365

Ser Gly Phe Ile Asn Lys Glu Gly Thr Arg Pro Ala Val Val Ile Pro
            370                 375                 380

Thr Asn Glu Glu Leu Val Ile Ala Gln Asp Ala Ser Arg Leu Thr Ala
385                 390                 395                 400

<210> SEQ ID NO 15
<211> LENGTH: 1719
<212> TYPE: DNA
<213> ORGANISM: Escherichia coli

<400> SEQUENCE: 15
atgaaacaaa cggttgcagc ttatatcgcc aaaacactcg aatcggcagg ggtgaaacgc      60
atctggggag tcacaggcga ctctctgaac ggtcttagtg acagtcttaa tcgcatgggc     120
accatcgagt ggatgtccac ccgccacgaa gaagtggcgg cctttgccgc tggcgctgaa     180
gcacaactta gcggagaact ggcggtctgc gccggatcgt gcggcccegg caacctgcac     240 ttaatcaacg gcctgttcga ttgccaccgc aatcacgttc cggtactggc gattgccgct     300
catattccct ccagcgaaat tggcagcggc tatttccagg aaacccaccc acaagagcta     360
ttccgcgaat gtagtcacta ttgcgagctg gtttccagcc ggagcagat cccacaagta     420 ctggcgattg ccatgcgcaa agcggtgctt aaccgtggcg tttcggttgt cgtgttacca     480
ggcgacgtgg cgttaaaaac ctgcgccaga ggggcaacca tgcactggta tcatgcgcca     540
caaccagtcg tgacgccgga agaagaagag ttacgcaaac tggcgcaact gctgcgttat     600
tccagcaata tcgccctgat gtgtggcagc ggctgcgcgg ggcgcataa agagttagtt     660 gagtttgccg ggaaaattaa agcgcctatt gttcatgccc tgcgcggtaa agaacatgtc     720
gaatacgata atccgtatga tgttggaatg accgggttaa tcggcttctc gtcaggtttc     780 ataccatga tgaacgccga cacgttagtg ctactcggca cgcaatttcc ctaccgcgcc     840
ttctacccga ccgatgccaa aatcattcag attgatatca cccagccag catcggcgct     900 cacagcaagg tggatatggc actggtcggc gatatcaagt cgactctgcg tgcattgctt     960
ccattggtgg aagaaaaagc cgatcgcaag tttctggata aagcgctgga agattaccgc    1020
gacgcccgca aagggctgga cgatttagct aaaccgagcg agaaagccat tcacccgcaa    1080
```

-continued

```
tatctggcgc agcaaattag tcattttgcc gccgatgacg ctattttcac ctgtgacgtt    1140
ggtacgccaa cggtgtgggc ggcacgttat ctaaaaatga acggcaagcg tcgcctgtta    1200
ggttcgttta accacggttc gatggctaac gccatgccgc aggcgctggg tgcgcaggcg    1260
acagagccag aacgtcaggt ggtcgccatg tgcggcgatg cggttttag catgttgatg     1320 ggcgatttcc tctcagtagt gcagatgaaa ctgccagtga aaattgtcgt ctttaacaac    1380
agcgtgctgg gctttgtggc gatggagatg aaagctggtg gctatttgac tgacggcacc    1440
gaactacacg acacaaactt tgcccgcatt gccgaagcgt gcggcattac gggtatccgt    1500
gtagaaaaag cgtctgaagt tgatgaagcc ctgcaacgcg ccttctccat cgacggtccg    1560
gtgttggtgg atgtggtggt cgccaaagaa gagttagcca ttccaccgca gatcaaactc    1620
gaacaggcca aggtttcag cctgtatatg ctgcgcgcaa tcatcagcgg acgcggtgat    1680
gaagtgatcg aactggcgaa acaaactgg ctaaggtaa                            1719
```

<210> SEQ ID NO 16
<211> LENGTH: 572
<212> TYPE: PRT
<213> ORGANISM: Escherichia coli

<400> SEQUENCE: 16

```
Met Lys Gln Thr Val Ala Ala Tyr Ile Ala Lys Thr Leu Glu Ser Ala
1               5                   10                  15

Gly Val Lys Arg Ile Trp Gly Val Thr Gly Asp Ser Leu Asn Gly Leu
            20                  25                  30

Ser Asp Ser Leu Asn Arg Met Gly Thr Ile Glu Trp Met Ser Thr Arg
        35                  40                  45

His Glu Glu Val Ala Ala Phe Ala Ala Gly Ala Glu Ala Gln Leu Ser
    50                  55                  60

Gly Glu Leu Ala Val Cys Ala Gly Ser Cys Gly Pro Gly Asn Leu His
65                  70                  75                  80

Leu Ile Asn Gly Leu Phe Asp Cys His Arg Asn His Val Pro Val Leu
                85                  90                  95

Ala Ile Ala Ala His Ile Pro Ser Ser Glu Ile Gly Ser Gly Tyr Phe
            100                 105                 110

Gln Glu Thr His Pro Gln Glu Leu Phe Arg Glu Cys Ser His Tyr Cys
        115                 120                 125

Glu Leu Val Ser Ser Pro Glu Gln Ile Pro Gln Val Leu Ala Ile Ala
    130                 135                 140

Met Arg Lys Ala Val Leu Asn Arg Gly Val Ser Val Val Val Leu Pro
145                 150                 155                 160

Gly Asp Val Ala Leu Lys Pro Ala Pro Glu Gly Ala Thr Met His Trp
                165                 170                 175

Tyr His Ala Pro Gln Pro Val Val Thr Pro Glu Glu Glu Leu Arg
            180                 185                 190

Lys Leu Ala Gln Leu Leu Arg Tyr Ser Ser Asn Ile Ala Leu Met Cys
        195                 200                 205

Gly Ser Gly Cys Ala Gly Ala His Lys Glu Leu Val Glu Phe Ala Gly
    210                 215                 220

Lys Ile Lys Ala Pro Ile Val His Ala Leu Arg Gly Lys Glu His Val
225                 230                 235                 240

Glu Tyr Asp Asn Pro Tyr Asp Val Gly Met Thr Gly Leu Ile Gly Phe
                245                 250                 255

Ser Ser Gly Phe His Thr Met Met Asn Ala Asp Thr Leu Val Leu Leu
```

```
                 260                 265                 270
Gly Thr Gln Phe Pro Tyr Arg Ala Phe Tyr Pro Thr Asp Ala Lys Ile
            275                 280                 285

Ile Gln Ile Asp Ile Asn Pro Ala Ser Ile Gly Ala His Ser Lys Val
        290                 295                 300

Asp Met Ala Leu Val Gly Asp Ile Lys Ser Thr Leu Arg Ala Leu Leu
305                 310                 315                 320

Pro Leu Val Glu Glu Lys Ala Asp Arg Lys Phe Leu Asp Lys Ala Leu
                325                 330                 335

Glu Asp Tyr Arg Asp Ala Arg Lys Gly Leu Asp Asp Leu Ala Lys Pro
            340                 345                 350

Ser Glu Lys Ala Ile His Pro Gln Tyr Leu Ala Gln Gln Ile Ser His
        355                 360                 365

Phe Ala Ala Asp Asp Ala Ile Phe Thr Cys Asp Val Gly Thr Pro Thr
    370                 375                 380

Val Trp Ala Ala Arg Tyr Leu Lys Met Asn Gly Lys Arg Arg Leu Leu
385                 390                 395                 400

Gly Ser Phe Asn His Gly Ser Met Ala Asn Ala Met Pro Gln Ala Leu
                405                 410                 415

Gly Ala Gln Ala Thr Glu Pro Glu Arg Gln Val Val Ala Met Cys Gly
            420                 425                 430

Asp Gly Gly Phe Ser Met Leu Met Gly Asp Phe Leu Ser Val Val Gln
        435                 440                 445

Met Lys Leu Pro Val Lys Ile Val Phe Asn Asn Ser Val Leu Gly
    450                 455                 460

Phe Val Ala Met Glu Met Lys Ala Gly Gly Tyr Leu Thr Asp Gly Thr
465                 470                 475                 480

Glu Leu His Asp Thr Asn Phe Ala Arg Ile Ala Glu Ala Cys Gly Ile
                485                 490                 495

Thr Gly Ile Arg Val Glu Lys Ala Ser Glu Val Asp Glu Ala Leu Gln
            500                 505                 510

Arg Ala Phe Ser Ile Asp Gly Pro Val Leu Val Asp Val Val Ala
        515                 520                 525

Lys Glu Glu Leu Ala Ile Pro Pro Gln Ile Lys Leu Glu Gln Ala Lys
    530                 535                 540

Gly Phe Ser Leu Tyr Met Leu Arg Ala Ile Ile Ser Gly Arg Gly Asp
545                 550                 555                 560

Glu Val Ile Glu Leu Ala Lys Thr Asn Trp Leu Arg
                565                 570

<210> SEQ ID NO 17
<211> LENGTH: 990
<212> TYPE: DNA
<213> ORGANISM: Escherichia coli

<400> SEQUENCE: 17
atgaaactcg ccgtttatag cacaaaacag tacgacaaga agtacctgca acaggtgaac      60
gagtcctttg ctttgagct ggaatttttt gactttctgc tgacggaaaa aaccgctaaa     120
actgccaatg gctgcgaagc ggtatgtatt ttcgtaaacg atgacggcag ccgcccggtg     180
ctggaagagc tgaaaaagca cggcgttaaa tatatcgcct tgcgctgtgc cggtttcaat     240
aacgtcgacc ttgacgcggc aaaagaactg gggctcaaag tagtccgtgt tccagcctat     300
gatccagagg ccgttgctga acacgccatc ggtatgatga tgacgctgaa ccgccgtatt     360
```

-continued

```
caccgcgcat atcagcgtac ccgtgacgct aacttctctc tggaaggtct gaccggcttt    420
actatgtatg caaaacggc aggcgttatc ggtaccggta aaatcggtgt ggcaatgctg     480
cgcattctga aaggttttgg tatgcgtctg ctggcgttcg atccgtatcc aagtgcggcg    540
gcgctggaac tcggtgtgga gtatgtcgat ctgccaaccc tgttctctga atcagacgtt    600
atctctctgc actgcccgct gacaccggaa aactaccatc tgttgaacga agccgccttc    660
gatcasatga aaaatggcgt gatgatcgtc aataccagtc gcggtgcatt gattgattct    720
caggcggcaa ttgaagcgct gaaaaatcag aaaattggtt cgttgggtat ggacgtgtat    780
gagaacgaac gcgatctgtt ctttgaagat aaatccaacg acgtgatcca ggatgacgta    840
ttccgtcgct tgtctgcctg ccacaacgtg ttgtttaccg ggcaccaggc attcctgaca    900
gcagaagctc tgaccagtat ttctcagact acgctgcaaa acttaagcaa tctggaaaaa    960
ggcgaaacct gcccgaacga actggtttaa                                     990
```

<210> SEQ ID NO 18
<211> LENGTH: 329
<212> TYPE: PRT
<213> ORGANISM: Escherichia coli
<220> FEATURE:
<221> NAME/KEY: misc_feature
<222> LOCATION: (222)..(222)
<223> OTHER INFORMATION: Xaa can be any naturally occurring amino acid

<400> SEQUENCE: 18

Met Lys Leu Ala Val Tyr Ser Thr Lys Gln Tyr Asp Lys Lys Tyr Leu
1               5                   10                  15

Gln Gln Val Asn Glu Ser Phe Gly Phe Glu Leu Glu Phe Phe Asp Phe
            20                  25                  30

Leu Leu Thr Glu Lys Thr Ala Lys Thr Ala Asn Gly Cys Glu Ala Val
        35                  40                  45

Cys Ile Phe Val Asn Asp Asp Gly Ser Arg Pro Val Leu Glu Glu Leu
    50                  55                  60

Lys Lys His Gly Val Lys Tyr Ile Ala Leu Arg Cys Ala Gly Phe Asn
65                  70                  75                  80

Asn Val Asp Leu Asp Ala Ala Lys Glu Leu Gly Leu Lys Val Val Arg
                85                  90                  95

Val Pro Ala Tyr Asp Pro Glu Ala Val Ala Glu His Ala Ile Gly Met
            100                 105                 110

Met Met Thr Leu Asn Arg Arg Ile His Arg Ala Tyr Gln Arg Thr Arg
        115                 120                 125

Asp Ala Asn Phe Ser Leu Glu Gly Leu Thr Gly Phe Thr Met Tyr Gly
    130                 135                 140

Lys Thr Ala Gly Val Ile Gly Thr Gly Lys Ile Gly Val Ala Met Leu
145                 150                 155                 160

Arg Ile Leu Lys Gly Phe Gly Met Arg Leu Leu Ala Phe Asp Pro Tyr
                165                 170                 175

Pro Ser Ala Ala Ala Leu Glu Leu Gly Val Glu Tyr Val Asp Leu Pro
            180                 185                 190

Thr Leu Phe Ser Glu Ser Asp Val Ile Ser Leu His Cys Pro Leu Thr
        195                 200                 205

Pro Glu Asn Tyr His Leu Leu Asn Glu Ala Ala Phe Asp Xaa Met Lys
    210                 215                 220

Asn Gly Val Met Ile Val Asn Thr Ser Arg Gly Ala Leu Ile Asp Ser
225                 230                 235                 240

Gln Ala Ala Ile Glu Ala Leu Lys Asn Gln Lys Ile Gly Ser Leu Gly
            245                 250                 255

Met Asp Val Tyr Glu Asn Glu Arg Asp Leu Phe Phe Glu Asp Lys Ser
        260                 265                 270

Asn Asp Val Ile Gln Asp Val Phe Arg Arg Leu Ser Ala Cys His
        275                 280                 285

Asn Val Leu Phe Thr Gly His Gln Ala Phe Leu Thr Ala Glu Ala Leu
        290                 295                 300

Thr Ser Ile Ser Gln Thr Thr Leu Gln Asn Leu Ser Asn Leu Glu Lys
305                 310                 315                 320

Gly Glu Thr Cys Pro Asn Glu Leu Val
            325

<210> SEQ ID NO 19
<211> LENGTH: 948
<212> TYPE: DNA
<213> ORGANISM: Escherichia coli

<400> SEQUENCE: 19
atgagactca ggaaatacaa taaaagtttg ggatggttgt cattatttgc aggcactgta      60
ttgctcagtg gctgtaattc tgcgctgtta gatcccaaag acagattgg tctggagcaa     120
cgttcactga tactgacggc atttggcctg atgttgattg tcgttattcc cgcaatcttg     180
atggctgttg gtttcgcctg gaagtaccgt gcgagcaata aagatgctaa gtacagcccg     240
aactggtcac actccaataa agtggaagct gtggtctgga cggtacctat cttaatcatc     300
atcttccttg cagtactgac ctggaaaacc actcacgctc ttgagcctag caagccgctg     360
gcacacgacg agaagcccat taccatcgaa gtggtttcca tggactggaa atggttcttc     420
atctaccgg aacagggcat tgctaccgtg aatgaaatcg ctttcccggc gaacactccg     480
gtgtacttca agtgaccctc caactccgtg atgaactcct tcttcattcc cgtctgggt     540
agccagattt atgccatggc cggtatgcag actcgcctgc atctgatcgc caacgaaccc     600
ggcacttatg acggtatctc cgccagctac agcggcccgg gcttctcagg catgaagttc     660
aaagctattg caacaccgga tcgcgccgca ttcgaccagt gggtcgcaaa agcgaagcag     720
tcgccgaaca ccatgtctga catggctgcg ttcgaaaaac tggccgcgcc tagcgaatac     780
aaccaggtgg aatatttctc caacgtgaaa ccagacttgt tgccgatgt aattaacaag     840
tttatggctc acggtaagag catggacatg acccagccag aaggtgagca cagcgcacac     900
gaaggtatgg aaggcatgga catgagccac gcggaatccg cccattaa                 948

<210> SEQ ID NO 20
<211> LENGTH: 315
<212> TYPE: PRT
<213> ORGANISM: Escherichia coli

<400> SEQUENCE: 20

Met Arg Leu Arg Lys Tyr Asn Lys Ser Leu Gly Trp Leu Ser Leu Phe
1               5                   10                  15

Ala Gly Thr Val Leu Leu Ser Gly Cys Asn Ser Ala Leu Leu Asp Pro
            20                  25                  30

Lys Gly Gln Ile Gly Leu Glu Gln Arg Ser Leu Ile Leu Thr Ala Phe
        35                  40                  45

Gly Leu Met Leu Ile Val Val Ile Pro Ala Ile Leu Met Ala Val Gly
    50                  55                  60

Phe Ala Trp Lys Tyr Arg Ala Ser Asn Lys Asp Ala Lys Tyr Ser Pro

```
                65                  70                  75                  80
Asn Trp Ser His Ser Asn Lys Val Glu Ala Val Val Trp Thr Val Pro
                    85                  90                  95

Ile Leu Ile Ile Ile Phe Leu Ala Val Leu Thr Trp Lys Thr Thr His
                100                 105                 110

Ala Leu Glu Pro Ser Lys Pro Leu Ala His Asp Glu Lys Pro Ile Thr
            115                 120                 125

Ile Glu Val Val Ser Met Asp Trp Lys Trp Phe Phe Ile Tyr Pro Glu
        130                 135                 140

Gln Gly Ile Ala Thr Val Asn Glu Ile Ala Phe Pro Ala Asn Thr Pro
145                 150                 155                 160

Val Tyr Phe Lys Val Thr Ser Asn Ser Val Met Asn Ser Phe Phe Ile
                165                 170                 175

Pro Arg Leu Gly Ser Gln Ile Tyr Ala Met Ala Gly Met Gln Thr Arg
            180                 185                 190

Leu His Leu Ile Ala Asn Glu Pro Gly Thr Tyr Asp Gly Ile Ser Ala
        195                 200                 205

Ser Tyr Ser Gly Pro Gly Phe Ser Gly Met Lys Phe Lys Ala Ile Ala
    210                 215                 220

Thr Pro Asp Arg Ala Ala Phe Asp Gln Trp Val Ala Lys Ala Lys Gln
225                 230                 235                 240

Ser Pro Asn Thr Met Ser Asp Met Ala Ala Phe Glu Lys Leu Ala Ala
                245                 250                 255

Pro Ser Glu Tyr Asn Gln Val Glu Tyr Phe Ser Asn Val Lys Pro Asp
            260                 265                 270

Leu Phe Ala Asp Val Ile Asn Lys Phe Met Ala His Gly Lys Ser Met
        275                 280                 285

Asp Met Thr Gln Pro Glu Gly Glu His Ser Ala His Glu Gly Met Glu
    290                 295                 300

Gly Met Asp Met Ser His Ala Glu Ser Ala His
305                 310                 315

<210> SEQ ID NO 21
<211> LENGTH: 1992
<212> TYPE: DNA
<213> ORGANISM: Escherichia coli

<400> SEQUENCE: 21
atgttcggaa aattatcact tgatgcagtc ccgttccatg aacctatcgt catggttacg      60
atcgctggca ttattttggg aggtctggcg ctcgttggcc tgatcactta cttcggtaag     120
tggacctacc tgtggaaaga gtggctgacc tccgtcgacc ataaacgcct cggtatcatg     180
tatatcatcg tggcgattgt gatgttactg cgtggttttg ctgacgccat tatgatgcgt     240
agccagcagg ctcttgcctc ggcgggcgaa gcgggtttcc tgccacctca ccactacgat     300
cagatcttca ccgcgcacgg cgtgattatg atcttcttcg tggcgatgcc tttcgttatc     360
ggtctgatga acctggtggt tccgctgcag atcggcgcgc gtgacgttgc gttcccgttc     420
ctcaacaact taagcttctg gtttaccgtt gttggtgtga ttctggttaa cgtttctctc     480
ggcgtgggcg aatttgcgca gaccggctgg ctggcctatc accgctatc  gggaatagag     540 tacagtccgg gagtcggtgt cgattactgg atatggagtc tccagctatc cggtataggt     600
acgacgctta ccggtatcaa cttcttcgtt accattctga agatgcgcgc accgggcatg     660
accatgttca agatgccagt atttacctgg gcatcactgt gcgcaaacgt actgattatt     720
```

```
gcttccttcc caattctgac ggttaccgtc gcgttgttga ccctggatcg ctatctgggc    780
acccatttct ttaccaacga tatgggtggc aacatgatga tgtatatcaa cctgatttgg    840
gcctggggcc acccggaagt ttacatcttg atcctgcctg tattcggtgt gttctccgaa    900
attgcggcaa ctttctcgcg taaacgtctg tttggttata cctcgctggt atgggcaacc    960
gtctgtatca ccgtgctgtc gttcatcgtt tggctgcacc acttctttac gatgggtgcg   1020
ggcgcgaacg taaacgcctt ctttggtatc accaccatga ttatcgccat cccaaccggg   1080
gtgaagatct tcaactggct gttcaccatg tatcagggcc gcatcgtgtt ccattctgcg   1140
atgctgtgga ccatcggttt tatcgtcacc ttctcggtgg gcggtatgac aggcgtgctg   1200
ctggcagtac ctggcgcaga cttcgttctg cataacagcc tgttcctgat tgcacacttc   1260
cataacgtga tcatcggcgg cgtggtcttc ggctgcttcg cagggatgac ctactggtgg   1320
cctaaagcgt tcggtttcaa actgaacgaa acctggggta acgcgcgtt ctggttctgg   1380 atcatcggct tcttcgttgc ctttatgccg ctgtatgcgt tgggctttat ggggatgacc   1440
cgtcgtttga gccagcagat tgacccgcag ttccacacca tgctgatgat tgcagccagc   1500
ggtgcggtac tgattgcgct gggtattctc tgcctcgtta ttcagatgta cgtttctatt   1560
cgcgaccgcg accagaaccg tgacctgact ggcgacccgt ggggtggccg tacgctggag   1620
tgggcaacct cttccccgcc tccgttctat aactttgccg ttgtgccgca cgttcacgaa   1680
cgtgatgcat tctgggaaat gaagagaaa ggcgaagcgt acaaaaagcc tgaccactat   1740
gaagaaattc atatgccaaa aaacagcggt gccggtatcg tcattgcggc tttctccacc   1800
atcttcggtt tcgccatgat ctggcatatc tggtggctgg cgattgttgg cttcgcaggc   1860
atgatcatca cctggatcgt gaaaagcttc gacgaggacg tggattacta cgtgccggtg   1920
gcagaaatcg aaaaactgga aaaccagcat ttcgatgaga ttactaaggc agggctgaaa   1980
aatggcaact ga                                                       1992
```

<210> SEQ ID NO 22
<211> LENGTH: 663
<212> TYPE: PRT
<213> ORGANISM: Escherichia coli

<400> SEQUENCE: 22

```
Met Phe Gly Lys Leu Ser Leu Asp Ala Val Pro Phe His Glu Pro Ile
1               5                   10                  15

Val Met Val Thr Ile Ala Gly Ile Ile Leu Gly Gly Leu Ala Leu Val
            20                  25                  30

Gly Leu Ile Thr Tyr Phe Gly Lys Trp Thr Tyr Leu Trp Lys Glu Trp
        35                  40                  45

Leu Thr Ser Val Asp His Lys Arg Leu Gly Ile Met Tyr Ile Ile Val
    50                  55                  60

Ala Ile Val Met Leu Leu Arg Gly Phe Ala Asp Ala Ile Met Met Arg
65                  70                  75                  80

Ser Gln Gln Ala Leu Ala Ser Ala Gly Glu Ala Gly Phe Leu Pro Pro
                85                  90                  95

His His Tyr Asp Gln Ile Phe Thr Ala His Gly Val Ile Met Ile Phe
            100                 105                 110

Phe Val Ala Met Pro Phe Val Ile Gly Leu Met Asn Leu Val Val Pro
        115                 120                 125

Leu Gln Ile Gly Ala Arg Asp Val Ala Phe Pro Phe Leu Asn Asn Leu
    130                 135                 140
```

```
Ser Phe Trp Phe Thr Val Val Gly Val Ile Leu Val Asn Val Ser Leu
145                 150                 155                 160

Gly Val Gly Glu Phe Ala Gln Thr Gly Trp Leu Ala Tyr Pro Pro Leu
            165                 170                 175

Ser Gly Ile Glu Tyr Ser Pro Gly Val Gly Val Asp Tyr Trp Ile Trp
            180                 185                 190

Ser Leu Gln Leu Ser Gly Ile Gly Thr Thr Leu Thr Gly Ile Asn Phe
    195                 200                 205

Phe Val Thr Ile Leu Lys Met Arg Ala Pro Gly Met Thr Met Phe Lys
        210                 215                 220

Met Pro Val Phe Thr Trp Ala Ser Leu Cys Ala Asn Val Leu Ile Ile
225                 230                 235                 240

Ala Ser Phe Pro Ile Leu Thr Val Thr Val Ala Leu Leu Thr Leu Asp
                245                 250                 255

Arg Tyr Leu Gly Thr His Phe Phe Thr Asn Asp Met Gly Gly Asn Met
                260                 265                 270

Met Met Tyr Ile Asn Leu Ile Trp Ala Trp Gly His Pro Glu Val Tyr
            275                 280                 285

Ile Leu Ile Leu Pro Val Phe Gly Val Phe Ser Glu Ile Ala Ala Thr
290                 295                 300

Phe Ser Arg Lys Arg Leu Phe Gly Tyr Thr Ser Leu Val Trp Ala Thr
305                 310                 315                 320

Val Cys Ile Thr Val Leu Ser Phe Ile Val Trp Leu His His Phe Phe
                325                 330                 335

Thr Met Gly Ala Gly Ala Asn Val Asn Ala Phe Phe Gly Ile Thr Thr
            340                 345                 350

Met Ile Ile Ala Ile Pro Thr Gly Val Lys Ile Phe Asn Trp Leu Phe
        355                 360                 365

Thr Met Tyr Gln Gly Arg Ile Val Phe His Ser Ala Met Leu Trp Thr
    370                 375                 380

Ile Gly Phe Ile Val Thr Phe Ser Val Gly Gly Met Thr Gly Val Leu
385                 390                 395                 400

Leu Ala Val Pro Gly Ala Asp Phe Val Leu His Asn Ser Leu Phe Leu
                405                 410                 415

Ile Ala His Phe His Asn Val Ile Ile Gly Gly Val Val Phe Gly Cys
                420                 425                 430

Phe Ala Gly Met Thr Tyr Trp Trp Pro Lys Ala Phe Gly Phe Lys Leu
            435                 440                 445

Asn Glu Thr Trp Gly Lys Arg Ala Phe Trp Phe Trp Ile Ile Gly Phe
        450                 455                 460

Phe Val Ala Phe Met Pro Leu Tyr Ala Leu Gly Phe Met Gly Met Thr
465                 470                 475                 480

Arg Arg Leu Ser Gln Gln Ile Asp Pro Gln Phe His Thr Met Leu Met
                485                 490                 495

Ile Ala Ala Ser Gly Ala Val Leu Ile Ala Leu Gly Ile Leu Cys Leu
                500                 505                 510

Val Ile Gln Met Tyr Val Ser Ile Arg Asp Arg Asp Gln Asn Arg Asp
            515                 520                 525

Leu Thr Gly Asp Pro Trp Gly Gly Arg Thr Leu Glu Trp Ala Thr Ser
        530                 535                 540

Ser Pro Pro Pro Phe Tyr Asn Phe Ala Val Val Pro His Val His Glu
545                 550                 555                 560

Arg Asp Ala Phe Trp Glu Met Lys Glu Lys Gly Glu Ala Tyr Lys Lys
```

```
                  565                 570                 575
Pro Asp His Tyr Glu Glu Ile His Met Pro Lys Asn Ser Gly Ala Gly
            580                 585                 590

Ile Val Ile Ala Ala Phe Ser Thr Ile Phe Gly Phe Ala Met Ile Trp
        595                 600                 605

His Ile Trp Trp Leu Ala Ile Val Gly Phe Ala Gly Met Ile Ile Thr
    610                 615                 620

Trp Ile Val Lys Ser Phe Asp Glu Asp Val Asp Tyr Tyr Val Pro Val
625                 630                 635                 640

Ala Glu Ile Glu Lys Leu Glu Asn Gln His Phe Asp Glu Ile Thr Lys
                645                 650                 655

Ala Gly Leu Lys Asn Gly Asn
            660

<210> SEQ ID NO 23
<211> LENGTH: 615
<212> TYPE: DNA
<213> ORGANISM: Escherichia coli

<400> SEQUENCE: 23
atggcaactg atactttgac gcacgcgact gcccacgcgc acgaacacgg gcaccacgat    60
gcaggcggaa ccaaaatttt cggattttgg atctacctga tgagcgactg cattctgttc   120
tctatcttgt ttgctaccta tgccgttctg gtgaacggca ccgcaggcgg cccgacaggt   180
aaggacattt tcgaactgcc gttcgttctg gttgaaactt tcttgctgtt gttcagctcc   240
atcacctatg gcatggcggc tatcgccatg tacaaaaaca caaaagcca ggtgatctcc    300 tggctggcgt tgacatggtt gtttggtgcc ggatttatcg ggatggaaat ctatgaattc   360
catcacctga ttgttaacgg catgggtccg gatcgcagcg gcttcctgtc agcgttcttt   420
gcgttggtcg gcacgcacgg tctgcacgtc acttccggtc ttatctggat ggcggtgctg   480
atggtgcaaa tcgcccgtcg cggcctgacc agcactaacc gtaccgcat catgtgtctg    540 agcctgttct ggcacttcct ggatgtggtt tggatctgtg tgttcactgt tgtttatctg   600
atgggggcga tgtaa                                                   615

<210> SEQ ID NO 24
<211> LENGTH: 204
<212> TYPE: PRT
<213> ORGANISM: Escherichia coli

<400> SEQUENCE: 24

Met Ala Thr Asp Thr Leu Thr His Ala Thr Ala His Ala His Glu His
1               5                   10                  15

Gly His His Asp Ala Gly Gly Thr Lys Ile Phe Gly Phe Trp Ile Tyr
            20                  25                  30

Leu Met Ser Asp Cys Ile Leu Phe Ser Ile Leu Phe Ala Thr Tyr Ala
        35                  40                  45

Val Leu Val Asn Gly Thr Ala Gly Gly Pro Thr Gly Lys Asp Ile Phe
    50                  55                  60

Glu Leu Pro Phe Val Leu Val Glu Thr Phe Leu Leu Leu Phe Ser Ser
65                  70                  75                  80

Ile Thr Tyr Gly Met Ala Ala Ile Ala Met Tyr Lys Asn Asn Lys Ser
                85                  90                  95

Gln Val Ile Ser Trp Leu Ala Leu Thr Trp Leu Phe Gly Ala Gly Phe
            100                 105                 110
```

Ile Gly Met Glu Ile Tyr Glu Phe His His Leu Ile Val Asn Gly Met
            115                 120                 125

Gly Pro Asp Arg Ser Gly Phe Leu Ser Ala Phe Phe Ala Leu Val Gly
    130                 135                 140

Thr His Gly Leu His Val Thr Ser Gly Leu Ile Trp Met Ala Val Leu
145                 150                 155                 160

Met Val Gln Ile Ala Arg Arg Gly Leu Thr Ser Thr Asn Arg Thr Arg
                165                 170                 175

Ile Met Cys Leu Ser Leu Phe Trp His Phe Leu Asp Val Val Trp Ile
            180                 185                 190

Cys Val Phe Thr Val Val Tyr Leu Met Gly Ala Met
            195                 200

<210> SEQ ID NO 25
<211> LENGTH: 330
<212> TYPE: DNA
<213> ORGANISM: Escherichia coli

<400> SEQUENCE: 25
atgagtcatt ctaacgtgag cggcggcgcg tcccatggca gcgtaaaaac ctacatgaca      60
ggctttatcc tgtcgatcat tctgacggtg attccgttct ggatggtgat gacaggggct     120
gcctctccgg ccgtaattct gggaacaatc ctggcaatgg cagtggtaca gattctggtg     180
catctggtgt gcttcctgca catgaatacc aaatcagatg aaggctggaa tatgacggca     240
tttgtcttca ccgtgctaat catcgccatc ctggttgtgg gctccatttg gattatgtgg     300
aacctcaact acaacatgat gatgcactaa                                      330

<210> SEQ ID NO 26
<211> LENGTH: 109
<212> TYPE: PRT
<213> ORGANISM: Escherichia coli

<400> SEQUENCE: 26

Met Ser His Ser Asn Val Ser Gly Gly Ala Ser His Gly Ser Val Lys
1               5                   10                  15

Thr Tyr Met Thr Gly Phe Ile Leu Ser Ile Ile Leu Thr Val Ile Pro
            20                  25                  30

Phe Trp Met Val Met Thr Gly Ala Ala Ser Pro Ala Val Ile Leu Gly
        35                  40                  45

Thr Ile Leu Ala Met Ala Val Val Gln Ile Leu Val His Leu Val Cys
    50                  55                  60

Phe Leu His Met Asn Thr Lys Ser Asp Glu Gly Trp Asn Met Thr Ala
65                  70                  75                  80

Phe Val Phe Thr Val Leu Ile Ile Ala Ile Leu Val Val Gly Ser Ile
                85                  90                  95

Trp Ile Met Trp Asn Leu Asn Tyr Asn Met Met Met His
            100                 105

<210> SEQ ID NO 27
<211> LENGTH: 891
<212> TYPE: DNA
<213> ORGANISM: Escherichia coli

<400> SEQUENCE: 27
atgatgttta agcaatacct gcaagtaacg aaaccaggca tcatctttgg caacctgatc      60
tcggtgattg ggggattcct gctggcctca aagggcagca ttgattatcc cctgtttatc     120

```
tacacgctgg tttggggtgtc actggttgtg gcgtcgggtt gtgtgtttaa caactacatc    180 gacaggata tcgacagaaa gatggaaagg acgaagaatc gggtgctggt gaaaggcctg    240
atctctcctg ctgtctcgct ggtgtacgcc acgttgctgg gtattgctgg ctttatgctg    300
ctgtggtttg gcgcgaatcc gctggcctgc tggctggggg tgatgggctt tgtggtttat    360
gtcggcgttt atagcctgta catgaaacgc cactctgtct acggcacgtt gattggttcg    420
ctctccggcg ctgcgccgcc ggtgatcggc tactgtgcgg taaccggtga gttcgatagc    480
ggcgcagcga tcctgctggc tatcttcagc ctgtggcaga tgcctcactc ctatgccatc    540
gccattttcc gctttaagga ttaccaggcg gcaaacattc cggtattgcc agtggtaaaa    600
ggcatttcgg tggcgaagaa tcacatcacg ctgtatatca tcgcctttgc cgttgccacg    660
ctgatgctct ctcttggcgg ttacgctggg tataaatatc tggtggtcgc cgcggcggtt    720
agcgtctggt ggttaggtat ggctctgcgc ggttataaag ttgctgatga cagaatctgg    780
gcgcgcaagc tgttcggctt ctctatcatc gccatcactg ccctctcggt gatgatgtcc    840
gttgatttta tggtaccgga ctcgcatacg ctgctggctg ctgtgtggta a              891
```

<210> SEQ ID NO 28
<211> LENGTH: 296
<212> TYPE: PRT
<213> ORGANISM: Escherichia coli

<400> SEQUENCE: 28

```
Met Met Phe Lys Gln Tyr Leu Gln Val Thr Lys Pro Gly Ile Ile Phe
1               5                   10                  15

Gly Asn Leu Ile Ser Val Ile Gly Gly Phe Leu Leu Ala Ser Lys Gly
            20                  25                  30

Ser Ile Asp Tyr Pro Leu Phe Ile Tyr Thr Leu Val Gly Val Ser Leu
        35                  40                  45

Val Val Ala Ser Gly Cys Val Phe Asn Asn Tyr Ile Asp Arg Asp Ile
    50                  55                  60

Asp Arg Lys Met Glu Arg Thr Lys Asn Arg Val Leu Val Lys Gly Leu
65                  70                  75                  80

Ile Ser Pro Ala Val Ser Leu Val Tyr Ala Thr Leu Leu Gly Ile Ala
                85                  90                  95

Gly Phe Met Leu Leu Trp Phe Gly Ala Asn Pro Leu Ala Cys Trp Leu
            100                 105                 110

Gly Val Met Gly Phe Val Val Tyr Val Gly Val Tyr Ser Leu Tyr Met
        115                 120                 125

Lys Arg His Ser Val Tyr Gly Thr Leu Ile Gly Ser Leu Ser Gly Ala
    130                 135                 140

Ala Pro Pro Val Ile Gly Tyr Cys Ala Val Thr Gly Glu Phe Asp Ser
145                 150                 155                 160

Gly Ala Ala Ile Leu Leu Ala Ile Phe Ser Leu Trp Gln Met Pro His
                165                 170                 175

Ser Tyr Ala Ile Ala Ile Phe Arg Phe Lys Asp Tyr Gln Ala Ala Asn
            180                 185                 190

Ile Pro Val Leu Pro Val Val Lys Gly Ile Ser Val Ala Lys Asn His
        195                 200                 205

Ile Thr Leu Tyr Ile Ile Ala Phe Ala Val Ala Thr Leu Met Leu Ser
    210                 215                 220

Leu Gly Gly Tyr Ala Gly Tyr Lys Tyr Leu Val Val Ala Ala Ala Val
225                 230                 235                 240
```

```
Ser Val Trp Trp Leu Gly Met Ala Leu Arg Gly Tyr Lys Val Ala Asp
            245                 250                 255

Asp Arg Ile Trp Ala Arg Lys Leu Phe Gly Phe Ser Ile Ile Ala Ile
        260                 265                 270

Thr Ala Leu Ser Val Met Met Ser Val Asp Phe Met Val Pro Asp Ser
    275                 280                 285

His Thr Leu Leu Ala Ala Val Trp
    290                 295

<210> SEQ ID NO 29
<211> LENGTH: 1779
<212> TYPE: DNA
<213> ORGANISM: Escherichia coli

<400> SEQUENCE: 29
gtggggtgtg tgatgaaatt gccagtcaga gaatttgatg cagttgtgat tggtgctggc      60
ggcgcaggta tgcgcgcggc gctgcaaatt tcccagagtg gccagacctg tgcgctgctc     120
tctaaagtct tcccgacccg ttcccatacc gtttctgcgc aaggtggtat taccgttgcg     180
ctgggtaata cccatgaaga taactggaa tggcatatgt acgacaccgt aaaagggtcg      240
gactatatcg tgaccaggga cgcgattgaa tatatgtgta aaaccgggcc ggaagcgatt     300
ctggaactgg aacatatggg cctgccgttc tcgcgtcttg atgatggtcg tatctatcaa     360
cgtccgtttg gcggtcagtc gaaaaacttc ggcggcgagc aggcggcacg tactgcggcg     420
gctgccgacc gtaccggtca cgcactgttg cacacgcttt atcagcagaa cctgaaaaac     480
cacaccacca ttttctccga gtggtatgcg ctggatctgg tgaaaaacca ggatggcgca     540
gtggtcggtt gtaccgcact gtgcatcgaa actggtgaag tggtttactt taaagctcgc     600
gcgacagtgc tggcgactgg cggggcaggg cgtatttatc agtccaccac caacgcccac     660
attaacactg gcgacggtgt cggcatggct atccgtgcag gcgtaccggt acaggatatg     720
gaaatgtggc agttccaccc gaccggtatt gccggtgcgg gcgtactggt caccgaaggt     780
tgccgtggtg aaggcggtta tctgctgaac aaacatggcg aacgctttat ggaacgttat     840
gcgccgaacg ccaaagacct ggcgggccgt gacgtggtgg cgcgttccat catgatcgaa     900
atccgtgaag ccgcggctg tgatggtccg tggggccac acgcaaaact gaaacttgac      960
catctgggga agaagttctc tgaatcccgt ctgccgggta tccttgaact ctcccgcacc    1020
ttcgctcacg ttgatccggt gaaagagccg attccggtta tcccaacctg tcactacatg    1080
atgggcggta ttccgaccaa agtgaccggt caggcgctga ctgtgaatga aaaggcgaa    1140 gatgtggttg ttccggggct atttgccgtt ggtgaaatcg cttgtgtatc ggtacatggc    1200
gctaaccgtc tgggcggcaa ctcgctgctg gacctggtcg tatttggtcg tgcggcaggt    1260
ctgcatctgc aagagtctat cgccgagcag ggcgcactgc gcgatgccag cgagtctgat    1320
gtagaagcgt ctctggatcg cctgaaccgc tggaacaata accgtaacgg tgaagatccg    1380
gtggcgatcc gtaaagcact gcaagaatgt atgcagcata acttctcggt cttccgtgaa    1440
ggtgatgcga tggcgaaagg gcttgagcag ttgaaagtta ccgcgagcg tttgaaaaat    1500 gcccgtctgg atgacacttc aagtgagttc aatacccagc gcgttgagtg cctggaactg    1560
gataacctga tggaaacggc gtatgcaacg gctgtttctg ccaacttccg taccgaaagc    1620
cgtggcgcgc atagccgctt cgacttcccg gatcgcgatg atgaaaactg gctgtgccac    1680
tccctgtatc tgccagagtc ggaatccatg acgcgccgaa gcgtcaacat ggaaccgaaa    1740
ctgcgcccgg cattcccgcc gaagattcgt acttactaa                          1779
```

<210> SEQ ID NO 30
<211> LENGTH: 592
<212> TYPE: PRT
<213> ORGANISM: Escherichia coli

<400> SEQUENCE: 30

```
Met Gly Cys Val Met Lys Leu Pro Val Arg Glu Phe Asp Ala Val Val
1               5                   10                  15

Ile Gly Ala Gly Gly Ala Gly Met Arg Ala Ala Leu Gln Ile Ser Gln
            20                  25                  30

Ser Gly Gln Thr Cys Ala Leu Leu Ser Lys Val Phe Pro Thr Arg Ser
        35                  40                  45

His Thr Val Ser Ala Gln Gly Gly Ile Thr Val Ala Leu Gly Asn Thr
    50                  55                  60

His Glu Asp Asn Trp Glu Trp His Met Tyr Asp Thr Val Lys Gly Ser
65                  70                  75                  80

Asp Tyr Ile Gly Asp Gln Asp Ala Ile Glu Tyr Met Cys Lys Thr Gly
                85                  90                  95

Pro Glu Ala Ile Leu Glu Leu Glu His Met Gly Leu Pro Phe Ser Arg
            100                 105                 110

Leu Asp Asp Gly Arg Ile Tyr Gln Arg Pro Phe Gly Gly Gln Ser Lys
        115                 120                 125

Asn Phe Gly Gly Glu Gln Ala Ala Arg Thr Ala Ala Ala Ala Asp Arg
130                 135                 140

Thr Gly His Ala Leu Leu His Thr Leu Tyr Gln Gln Asn Leu Lys Asn
145                 150                 155                 160

His Thr Thr Ile Phe Ser Glu Trp Tyr Ala Leu Asp Leu Val Lys Asn
                165                 170                 175

Gln Asp Gly Ala Val Val Gly Cys Thr Ala Leu Cys Ile Glu Thr Gly
            180                 185                 190

Glu Val Val Tyr Phe Lys Ala Arg Ala Thr Val Leu Ala Thr Gly Gly
        195                 200                 205

Ala Gly Arg Ile Tyr Gln Ser Thr Thr Asn Ala His Ile Asn Thr Gly
    210                 215                 220

Asp Gly Val Gly Met Ala Ile Arg Ala Gly Val Pro Val Gln Asp Met
225                 230                 235                 240

Glu Met Trp Gln Phe His Pro Thr Gly Ile Ala Gly Ala Gly Val Leu
                245                 250                 255

Val Thr Glu Gly Cys Arg Gly Glu Gly Gly Tyr Leu Leu Asn Lys His
            260                 265                 270

Gly Glu Arg Phe Met Glu Arg Tyr Ala Pro Asn Ala Lys Asp Leu Ala
        275                 280                 285

Gly Arg Asp Val Val Ala Arg Ser Ile Met Ile Glu Ile Arg Glu Gly
    290                 295                 300

Arg Gly Cys Asp Gly Pro Trp Gly Pro His Ala Lys Leu Lys Leu Asp
305                 310                 315                 320

His Leu Gly Lys Glu Val Leu Glu Ser Arg Leu Pro Gly Ile Leu Glu
                325                 330                 335

Leu Ser Arg Thr Phe Ala His Val Asp Pro Val Lys Glu Pro Ile Pro
            340                 345                 350

Val Ile Pro Thr Cys His Tyr Met Met Gly Gly Ile Pro Thr Lys Val
        355                 360                 365

Thr Gly Gln Ala Leu Thr Val Asn Glu Lys Gly Glu Asp Val Val Val
```

-continued

```
                   370                 375                 380
Pro Gly Leu Phe Ala Val Gly Glu Ile Ala Cys Val Ser Val His Gly
385                 390                 395                 400

Ala Asn Arg Leu Gly Gly Asn Ser Leu Leu Asp Leu Val Val Phe Gly
                405                 410                 415

Arg Ala Ala Gly Leu His Leu Gln Glu Ser Ile Ala Glu Gln Gly Ala
            420                 425                 430

Leu Arg Asp Ala Ser Glu Ser Asp Val Glu Ala Ser Leu Asp Arg Leu
        435                 440                 445

Asn Arg Trp Asn Asn Arg Asn Gly Glu Asp Pro Val Ala Ile Arg
    450                 455                 460

Lys Ala Leu Gln Glu Cys Met Gln His Asn Phe Ser Val Phe Arg Glu
465                 470                 475                 480

Gly Asp Ala Met Ala Lys Gly Leu Glu Gln Leu Lys Val Ile Arg Glu
                485                 490                 495

Arg Leu Lys Asn Ala Arg Leu Asp Asp Thr Ser Ser Glu Phe Asn Thr
                500                 505                 510

Gln Arg Val Glu Cys Leu Glu Leu Asp Asn Leu Met Glu Thr Ala Tyr
            515                 520                 525

Ala Thr Ala Val Ser Ala Asn Phe Arg Thr Glu Ser Arg Gly Ala His
        530                 535                 540

Ser Arg Phe Asp Phe Pro Asp Arg Asp Asp Glu Asn Trp Leu Cys His
545                 550                 555                 560

Ser Leu Tyr Leu Pro Glu Ser Glu Ser Met Thr Arg Arg Ser Val Asn
                565                 570                 575

Met Glu Pro Lys Leu Arg Pro Ala Phe Pro Pro Lys Ile Arg Thr Tyr
                580                 585                 590

<210> SEQ ID NO 31
<211> LENGTH: 717
<212> TYPE: DNA
<213> ORGANISM: Escherichia coli

<400> SEQUENCE: 31
atgagactcg agttttcaat ttatcgctat aacccggatg ttgatgatgc tccgcgtatg      60
caggattaca ccctggaagc ggaagaaggt cgcgacatga tgctgctgga tgcgcttatt     120
cagctgaaag agaaagatcc cagcctgtcg ttccgccgct cctgccgtga aggtgtgtgc     180
ggttccgacg gtctgaacat gaacggtaag aatggtctgg cctgtattac cccgatttcg     240
gcactcaacc agccgggcaa gaagattgtg attcgcccgc tgccaggttt accggtgatc     300
cgcgatttgg tggtagacat gggacaattc tatgcgcaat atgagaaaat taagccttac     360
ctgttgaata tggacaaaaa tccgccagct cgcgagcatt tacagatgcc agagcagcgc     420
gaaaaactcg acgggttgta tgaatgtatt ctctgcgcat gttgttcaac ctcttgtccg     480
tctttctggt ggaatcccga taagtttatc ggcccggcag gcttgttagc ggcatatcgt     540
ttcctgatcg atagccgtga taccgagact gacagccgcc tcgacggttt gagcgatgca     600
ttcagtgtat tccgctgtca cagcatcatg aactgcgtca gtgtatgtcc gaaggggctg     660
aacccgacgc gcgccatcgg ccatatcaag tcgatgttgt tgcaacgtaa tgcgtaa       717

<210> SEQ ID NO 32
<211> LENGTH: 238
<212> TYPE: PRT
<213> ORGANISM: Escherichia coli
```

<400> SEQUENCE: 32

```
Met Arg Leu Glu Phe Ser Ile Tyr Arg Tyr Asn Pro Asp Val Asp
1               5                   10                  15

Ala Pro Arg Met Gln Asp Tyr Thr Leu Glu Ala Glu Gly Arg Asp
                20                  25                  30

Met Met Leu Leu Asp Ala Leu Ile Gln Leu Lys Glu Lys Asp Pro Ser
            35                  40                  45

Leu Ser Phe Arg Arg Ser Cys Arg Glu Gly Val Cys Gly Ser Asp Gly
        50                  55                  60

Leu Asn Met Asn Gly Lys Asn Gly Leu Ala Cys Ile Thr Pro Ile Ser
65                  70                  75                  80

Ala Leu Asn Gln Pro Gly Lys Lys Ile Val Ile Arg Pro Leu Pro Gly
                85                  90                  95

Leu Pro Val Ile Arg Asp Leu Val Val Asp Met Gly Gln Phe Tyr Ala
            100                 105                 110

Gln Tyr Glu Lys Ile Lys Pro Tyr Leu Leu Asn Asn Gly Gln Asn Pro
        115                 120                 125

Pro Ala Arg Glu His Leu Gln Met Pro Glu Gln Arg Glu Lys Leu Asp
130                 135                 140

Gly Leu Tyr Glu Cys Ile Leu Cys Ala Cys Cys Ser Thr Ser Cys Pro
145                 150                 155                 160

Ser Phe Trp Trp Asn Pro Asp Lys Phe Ile Gly Pro Ala Gly Leu Leu
                165                 170                 175

Ala Ala Tyr Arg Phe Leu Ile Asp Ser Arg Asp Thr Glu Thr Asp Ser
            180                 185                 190

Arg Leu Asp Gly Leu Ser Asp Ala Phe Ser Val Phe Arg Cys His Ser
        195                 200                 205

Ile Met Asn Cys Val Ser Val Cys Pro Lys Gly Leu Asn Pro Thr Arg
            210                 215                 220

Ala Ile Gly His Ile Lys Ser Met Leu Leu Gln Arg Asn Ala
225                 230                 235
```

<210> SEQ ID NO 33
<211> LENGTH: 405
<212> TYPE: DNA
<213> ORGANISM: Escherichia coli

<400> SEQUENCE: 33

```
atgtgggcgt tattcatgat aagaaatgtg aaaaaacaaa gacctgttaa tctggaccta      60
cagaccatcc ggttccccgt cacggcgata gcgtccattc tccatcgcgt ttccggtgtg     120
atcacctttg ttgcagtggg catcctgctg tggcttctgg gtaccagcct ctcttcccct     180
gaaggtttcg agcaagcttc cgcgattatg ggcagcttct tcgtcaaatt tatcatgtgg     240
ggcatcctta ccgctctggc atatcacgtc gtcgtaggta ttcgccacat gatgatggat     300
tttggctatc tggaagaaac attcgaagcg gtaaacgct ccgccaaaat ctcctttgtt      360
attactgtcg tgctttcact tctcgcagga gtcctcgtat ggtaa                     405
```

<210> SEQ ID NO 34
<211> LENGTH: 134
<212> TYPE: PRT
<213> ORGANISM: Escherichia coli

<400> SEQUENCE: 34

```
Met Trp Ala Leu Phe Met Ile Arg Asn Val Lys Lys Gln Arg Pro Val
1               5                   10                  15
```

Asn Leu Asp Leu Gln Thr Ile Arg Phe Pro Val Thr Ala Ile Ala Ser
                20                  25                  30

Ile Leu His Arg Val Ser Gly Val Ile Thr Phe Val Ala Val Gly Ile
            35                  40                  45

Leu Leu Trp Leu Leu Gly Thr Ser Leu Ser Ser Pro Glu Gly Phe Glu
 50                  55                  60

Gln Ala Ser Ala Ile Met Gly Ser Phe Phe Val Lys Phe Ile Met Trp
 65                  70                  75                  80

Gly Ile Leu Thr Ala Leu Ala Tyr His Val Val Gly Ile Arg His
                85                  90                  95

Met Met Met Asp Phe Gly Tyr Leu Glu Glu Thr Phe Glu Ala Gly Lys
                100                 105                 110

Arg Ser Ala Lys Ile Ser Phe Val Ile Thr Val Leu Ser Leu Leu
            115                 120                 125

Ala Gly Val Leu Val Trp
        130

<210> SEQ ID NO 35
<211> LENGTH: 348
<212> TYPE: DNA
<213> ORGANISM: Escherichia coli

<400> SEQUENCE: 35
atggtaagca acgcctccgc attaggacgc aatggcgtac atgatttcat cctcgttcgt     60
gctaccgcta tcgtcctgac gctctacatc atttatatgg tcggtttttt cgctaccagt    120
ggcgagctga catatgaagt ctggattggt ttcttcgcct ctgcgttcac caaagtgttc    180
accctgctgg cgctgttttc tatcttgatc catgcctgga tcggcatgtg gcaggtgttg    240
accgactacg ttaaaccgct ggccttgcgc ctgatgctgc aactggtgat tgtcgttgca    300
ctggtggttt acgtgattta tggattcgtt gtggtgtggg gtgtgtga              348

<210> SEQ ID NO 36
<211> LENGTH: 115
<212> TYPE: PRT
<213> ORGANISM: Escherichia coli

<400> SEQUENCE: 36

Met Val Ser Asn Ala Ser Ala Leu Gly Arg Asn Gly Val His Asp Phe
1               5                   10                  15

Ile Leu Val Arg Ala Thr Ala Ile Val Leu Thr Leu Tyr Ile Ile Tyr
                20                  25                  30

Met Val Gly Phe Phe Ala Thr Ser Gly Glu Leu Thr Tyr Glu Val Trp
            35                  40                  45

Ile Gly Phe Phe Ala Ser Ala Phe Thr Lys Val Phe Thr Leu Leu Ala
 50                  55                  60

Leu Phe Ser Ile Leu Ile His Ala Trp Ile Gly Met Trp Gln Val Leu
 65                  70                  75                  80

Thr Asp Tyr Val Lys Pro Leu Ala Leu Arg Leu Met Leu Gln Leu Val
                85                  90                  95

Ile Val Val Ala Leu Val Val Tyr Val Ile Tyr Gly Phe Val Val Val
                100                 105                 110

Trp Gly Val
        115

<210> SEQ ID NO 37

<211> LENGTH: 1407
<212> TYPE: DNA
<213> ORGANISM: Escherichia coli

<400> SEQUENCE: 37

| | | | | | |
|---|---|---|---|---|---|
| atgtcaaagc | aacagatcgg | cgtagtcggt | atggcagtga | tggggcgcaa | ccttgcgctc | 60 |
| aacatcgaaa | gtcgtggtta | taccgtctct | attttcaacc | gttcccgtga | aaagacggaa | 120 |
| gaagtgattg | ccgaaaatcc | aggcaaaaaa | ctggttcctt | actatacggt | gaaagagttt | 180 |
| gttgaatctc | tggaaacgcc | tcgtcgcatc | ctgttaatgg | tgaaagcagg | tgcaggcacg | 240 |
| gatgctgcta | ttgattccct | caagccatac | ctcgataaag | gtgacatcat | cattgatggt | 300 |
| ggtaatacct | tcttccagga | caccattcgt | cgtaaccgtg | agctttctgc | cgaaggcttt | 360 |
| aacttcattg | gtaccggtgt | ctccggtggt | gaagaaggcg | cgctgaaagg | tccttccatt | 420 |
| atgcctggtg | ggcagaaaga | agcctatgaa | cttgttgcgc | cgatcctgac | caaaatcgcc | 480 |
| gcagtggctg | aagacggtga | gccatgcgtt | acctatattg | gtgccgatgg | cgcaggtcac | 540 |
| tatgtgaaga | tggttcacaa | cggtattgaa | tacgagagata | tgcaactgat | tgctgaagcc | 600 |
| tattctctgc | ttaaaggtgg | cctgaacctc | accaacgaag | aactggcgca | gacctttacc | 660 |
| gagtggaata | acggtgaact | gagcagctac | ctgatcgaca | tcaccaaaga | tatcttcacc | 720 |
| aaaaaagatg | aagatggtaa | ctacctggtt | gatgtgatcc | tggatgaagc | agcaaacaaa | 780 |
| ggcacgggca | atggaccag | ccagagtgcg | ctggatctcg | cgaaccgct | gtcgctgatt | 840 |
| accgagtctg | tgtttgcacg | ttatatctct | tctctgaaag | atcagcgtgt | tgccgcatct | 900 |
| aaagttctct | ctggcccgca | agcacagcca | gcaggcgaca | aggctgagtt | catcgaaaaa | 960 |
| gttcgccgtg | cgctgtatct | tggcaaaatc | gtttcttacg | ctcagggctt | ctctcagctg | 1020 |
| cgtgctgcgt | ctgaagagta | caactgggat | ctgaactacg | tgaaatcgc | gaagattttc | 1080 |
| cgtgctggct | gcatcatccg | tgcgcagttc | ctgcagaaaa | tcaccgatgc | ttatgccgaa | 1140 |
| aatccgcaga | tcgctaacct | gctgctggct | ccgtacttca | gcaaattgc | cgatgactac | 1200 |
| cagcaggctc | tgcgtgatgt | cgttgcttat | gcagtacaga | acggtatccc | ggttccgacc | 1260 |
| ttcgccgctg | cggttgccta | ttacgatagc | taccgtgccg | ctgttctgcc | tgcgaacctg | 1320 |
| atccaggcac | agcgtgacta | tttcggtgca | catacttata | agcgcattga | taaagaaggt | 1380 |
| gtgttccata | ctgaatggct | ggattaa | | | | 1407 |

<210> SEQ ID NO 38
<211> LENGTH: 468
<212> TYPE: PRT
<213> ORGANISM: Escherichia coli

<400> SEQUENCE: 38

Met Ser Lys Gln Gln Ile Gly Val Val Gly Met Ala Val Met Gly Arg
1               5                   10                  15

Asn Leu Ala Leu Asn Ile Glu Ser Arg Gly Tyr Thr Val Ser Ile Phe
            20                  25                  30

Asn Arg Ser Arg Glu Lys Thr Glu Glu Val Ile Ala Glu Asn Pro Gly
        35                  40                  45

Lys Lys Leu Val Pro Tyr Tyr Thr Val Lys Glu Phe Val Glu Ser Leu
    50                  55                  60

Glu Thr Pro Arg Arg Ile Leu Leu Met Val Lys Ala Gly Ala Gly Thr
65                  70                  75                  80

Asp Ala Ala Ile Asp Ser Leu Lys Pro Tyr Leu Asp Lys Gly Asp Ile
                85                  90                  95

```
Ile Ile Asp Gly Gly Asn Thr Phe Phe Gln Asp Thr Ile Arg Arg Asn
            100                 105                 110

Arg Glu Leu Ser Ala Glu Gly Phe Asn Phe Ile Gly Thr Gly Val Ser
            115                 120                 125

Gly Gly Glu Glu Gly Ala Leu Lys Gly Pro Ser Ile Met Pro Gly Gly
130             135                 140

Gln Lys Glu Ala Tyr Glu Leu Val Ala Pro Ile Leu Thr Lys Ile Ala
145                 150                 155                 160

Ala Val Ala Glu Asp Gly Glu Pro Cys Val Thr Tyr Ile Gly Ala Asp
            165                 170                 175

Gly Ala Gly His Tyr Val Lys Met Val His Asn Gly Ile Glu Tyr Gly
            180                 185                 190

Asp Met Gln Leu Ile Ala Glu Ala Tyr Ser Leu Leu Lys Gly Gly Leu
            195                 200                 205

Asn Leu Thr Asn Glu Glu Leu Ala Gln Thr Phe Thr Glu Trp Asn Asn
            210                 215                 220

Gly Glu Leu Ser Ser Tyr Leu Ile Asp Ile Thr Lys Asp Ile Phe Thr
225                 230                 235                 240

Lys Lys Asp Glu Asp Gly Asn Tyr Leu Val Asp Val Ile Leu Asp Glu
            245                 250                 255

Ala Ala Asn Lys Gly Thr Gly Lys Trp Thr Ser Gln Ser Ala Leu Asp
            260                 265                 270

Leu Gly Glu Pro Leu Ser Leu Ile Thr Glu Ser Val Phe Ala Arg Tyr
            275                 280                 285

Ile Ser Ser Leu Lys Asp Gln Arg Val Ala Ala Ser Lys Val Leu Ser
            290                 295                 300

Gly Pro Gln Ala Gln Pro Ala Gly Asp Lys Ala Glu Phe Ile Glu Lys
305                 310                 315                 320

Val Arg Arg Ala Leu Tyr Leu Gly Lys Ile Val Ser Tyr Ala Gln Gly
            325                 330                 335

Phe Ser Gln Leu Arg Ala Ala Ser Glu Glu Tyr Asn Trp Asp Leu Asn
            340                 345                 350

Tyr Gly Glu Ile Ala Lys Ile Phe Arg Ala Gly Cys Ile Ile Arg Ala
            355                 360                 365

Gln Phe Leu Gln Lys Ile Thr Asp Ala Tyr Ala Glu Asn Pro Gln Ile
            370                 375                 380

Ala Asn Leu Leu Leu Ala Pro Tyr Phe Lys Gln Ile Ala Asp Asp Tyr
385                 390                 395                 400

Gln Gln Ala Leu Arg Asp Val Val Ala Tyr Ala Val Gln Asn Gly Ile
            405                 410                 415

Pro Val Pro Thr Phe Ala Ala Val Ala Tyr Tyr Asp Ser Tyr Arg
            420                 425                 430

Ala Ala Val Leu Pro Ala Asn Leu Ile Gln Ala Gln Arg Asp Tyr Phe
            435                 440                 445

Gly Ala His Thr Tyr Lys Arg Ile Asp Lys Glu Gly Val Phe His Thr
            450                 455                 460

Glu Trp Leu Asp
465

<210> SEQ ID NO 39
<211> LENGTH: 1344
<212> TYPE: DNA
<213> ORGANISM: Escherichia coli
```

<400> SEQUENCE: 39

```
atggatcaga catattctct ggagtcattc ctcaaccatg tccaaaagcg cgacccgaat    60
caaaccgagt tcgcgcaagc cgttcgtgaa gtaatgacca cactctggcc ttttcttgaa   120
caaaatccaa aatatcgcca gatgtcatta ctggagcgtc tggttgaacc ggagcgcgtg   180
atccagtttc gcgtggtatg ggttgatgat cgcaaccaga tacaggtcaa ccgtgcatgg   240
cgtgtgcagt tcagctctgc catcggcccg tacaaaggcg gtatgcgctt ccatccgtca   300
gttaaccttt ccattctcaa attcctcggc tttgaacaaa ccttcaaaaa tgccctgact   360
actctgccga tgggcggtgg taaaggcggc agcgatttcg atccgaaagg aaaaagcgaa   420
ggtgaagtga tgcgttttg ccaggcgctg atgactgaac tgtatcgcca cctgggcgcg   480
gataccgacg ttccggcagg tgatatcggg gttggtggtc gtgaagtcgg ctttatggcg   540
gggatgatga aaagctctc caacaatacc gcctgcgtct tcaccggtaa gggccttttca   600
tttggcggca gtcttattcg cccggaagct accggctacg gtctggttta tttcacagaa   660
gcaatgctaa aacgccacgg tatgggtttt gaagggatgc gcgtttccgt ttctggctcc   720
ggcaacgtcg cccagtacgc tatcgaaaaa gcgatggaat ttggtgctcg tgtgatcact   780
gcgtcagact ccagcggcac tgtagttgat gaaagcggat tcacgaaaga aaactggca   840
cgtcttatcg aaatcaaagc cagccgcgat ggtcgagtgg cagattacgc caaagaattt   900
ggtctggtct atctcgaagg ccaacagccg tggtctctac cggttgatat cgccctgcct   960
tgcgccaccc agaatgaact ggatgttgac gccgcgcatc agcttatcgc taatggcgtt  1020
aaagccgtcg ccgaaggggc aaatatgccg accaccatcg aagcgactga actgttccag  1080
caggcaggcg tactatttgc accgggtaaa gcggctaatg ctggtggcgt cgctacatcg  1140
ggcctggaaa tggcacaaaa cgctgcgcgc ctgggctgga aagccagaa agttgacgca  1200
cgtttgcatc acatcatgct ggatatccac catgcctgtg ttgagcatgg tggtgaaggt  1260
gagcaaacca actacgtgca gggcgcgaac attgccggtt ttgtgaaggt tgccgatgcg  1320
atgctggcgc agggtgtgat ttaa                                         1344
```

<210> SEQ ID NO 40
<211> LENGTH: 447
<212> TYPE: PRT
<213> ORGANISM: Escherichia coli

<400> SEQUENCE: 40

```
Met Asp Gln Thr Tyr Ser Leu Glu Ser Phe Leu Asn His Val Gln Lys
1               5                   10                  15

Arg Asp Pro Asn Gln Thr Glu Phe Ala Gln Ala Val Arg Glu Val Met
            20                  25                  30

Thr Thr Leu Trp Pro Phe Leu Glu Gln Asn Pro Lys Tyr Arg Gln Met
        35                  40                  45

Ser Leu Leu Glu Arg Leu Val Glu Pro Glu Arg Val Ile Gln Phe Arg
    50                  55                  60

Val Val Trp Val Asp Asp Arg Asn Gln Ile Gln Val Asn Arg Ala Trp
65                  70                  75                  80

Arg Val Gln Phe Ser Ser Ala Ile Gly Pro Tyr Lys Gly Gly Met Arg
                85                  90                  95

Phe His Pro Ser Val Asn Leu Ser Ile Leu Lys Phe Leu Gly Phe Glu
            100                 105                 110

Gln Thr Phe Lys Asn Ala Leu Thr Thr Leu Pro Met Gly Gly Gly Lys
        115                 120                 125
```

Gly Gly Ser Asp Phe Asp Pro Lys Gly Lys Ser Glu Gly Glu Val Met
            130                 135                 140
Arg Phe Cys Gln Ala Leu Met Thr Glu Leu Tyr Arg His Leu Gly Ala
145                 150                 155                 160
Asp Thr Asp Val Pro Ala Gly Asp Ile Gly Val Gly Gly Arg Glu Val
                165                 170                 175
Gly Phe Met Ala Gly Met Met Lys Lys Leu Ser Asn Asn Thr Ala Cys
            180                 185                 190
Val Phe Thr Gly Lys Gly Leu Ser Phe Gly Gly Ser Leu Ile Arg Pro
        195                 200                 205
Glu Ala Thr Gly Tyr Gly Leu Val Tyr Phe Thr Glu Ala Met Leu Lys
    210                 215                 220
Arg His Gly Met Gly Phe Glu Gly Met Arg Val Ser Val Ser Gly Ser
225                 230                 235                 240
Gly Asn Val Ala Gln Tyr Ala Ile Glu Lys Ala Met Glu Phe Gly Ala
                245                 250                 255
Arg Val Ile Thr Ala Ser Asp Ser Ser Gly Thr Val Val Asp Glu Ser
            260                 265                 270
Gly Phe Thr Lys Glu Lys Leu Ala Arg Leu Ile Glu Ile Lys Ala Ser
        275                 280                 285
Arg Asp Gly Arg Val Ala Asp Tyr Ala Lys Glu Phe Gly Leu Val Tyr
    290                 295                 300
Leu Glu Gly Gln Gln Pro Trp Ser Leu Pro Val Asp Ile Ala Leu Pro
305                 310                 315                 320
Cys Ala Thr Gln Asn Glu Leu Asp Val Asp Ala Ala His Gln Leu Ile
                325                 330                 335
Ala Asn Gly Val Lys Ala Val Ala Glu Gly Ala Asn Met Pro Thr Thr
            340                 345                 350
Ile Glu Ala Thr Glu Leu Phe Gln Gln Ala Gly Val Leu Phe Ala Pro
        355                 360                 365
Gly Lys Ala Ala Asn Ala Gly Gly Val Ala Thr Ser Gly Leu Glu Met
    370                 375                 380
Ala Gln Asn Ala Ala Arg Leu Gly Trp Lys Ala Glu Lys Val Asp Ala
385                 390                 395                 400
Arg Leu His His Ile Met Leu Asp Ile His His Ala Cys Val Glu His
                405                 410                 415
Gly Gly Glu Gly Glu Gln Thr Asn Tyr Val Gln Gly Ala Asn Ile Ala
            420                 425                 430
Gly Phe Val Lys Val Ala Asp Ala Met Leu Ala Gln Gly Val Ile
        435                 440                 445

<210> SEQ ID NO 41
<211> LENGTH: 2283
<212> TYPE: DNA
<213> ORGANISM: Escherichia coli

<400> SEQUENCE: 41
atgtccgagc ttaatgaaaa gttagccaca gcctgggaag gttttaccaa aggtgactgg      60
cagaatgaag taaacgtccg tgacttcatt cagaaaaact acactccgta cgagggtgac     120
gagtccttcc tggctggcgc tactgaagcg accaccaccc tgtgggacaa agtaatggaa     180
ggcgttaaac tggaaaaccg cactcacgcg ccagttgact ttgacaccgc tgttgcttcc     240
accatcaccc tctcacgacg ctggctacatc aacaagcagc ttgagaaaat cgttggtctg     300

```
cagactgaag ctccgctgaa acgtgctctt atcccgttcg gtggtatcaa aatgatcgaa    360
ggttcctgca aagcgtacaa ccgcgaactg gatccgatga tcaaaaaaat cttcactgaa    420
taccgtaaaa ctcacaacca gggcgtgttc gacgtttaca ctccggacat cctgcgttgc    480
cgtaaatctg tgttctgac cggtctgcca gatgcatatg gccgtggccg tatcatcggt     540
gactaccgtc gcgttgcgct gtacggtatc gactacctga tgaaagacaa actggcacag    600
ttcacttctc tgcaggctga tctggaaaac ggcgtaaacc tggaacagac tatccgtctg    660
cgcgaagaaa tcgctgaaca gcaccgcgct ctgggtcaga tgaaagaaat ggctgcgaaa    720
tacggctacg acatctctgg tccggctacc aacgctcagg aagctatcca gtggacttac    780
ttcggctacc tggctgctgt taagtctcag aacggtgctg caatgtcctt cggtcgtacc    840
tccaccttcc tggatgtgta catcgaacgt gacctgaaag ctggcaagat caccgaacaa    900
gaagcgcagg aaatggttga ccacctggtc atgaaactgc gtatggttcg cttcctgcgt    960
actccggaat acgatgaact gttctctggc gacccgatct gggcaaccga atctatcggt   1020
ggtatgggcc tcgacggtcg tacccctggtt accaaaaaca gcttccgttt cctgaacacc   1080
ctgtacacca tgggtccgtc tccggaaccg aacatgacca ttctgtggtc tgaaaaactg   1140
ccgctgaact tcaagaaatt cgccgctaaa gtgtccatcg acacctcttc tctgcagtat   1200
gagaacgatg acctgatgcg tccggacttc aacaacgatg actacgctat tgcttgctgc   1260
gtaagcccga tgatcgttgg taaacaaatg cagttcttcg gtgcgcgtgc aaacctggcg   1320
aaaaccatgc tgtacgcaat caacggcggc gttgacgaaa aactgaaaat gcaggttggt   1380
ccgaagtctg aaccgatcaa aggcgatgtc ctgaactatg atgaagtgat ggagcgcatg   1440
gatcacttca tggactggct ggctaaacag tacatcactg cactgaacat catccactac    1500
atgcacgaca agtacagcta cgaagcctct ctgatggcgc tgcacgaccg tgacgttatc    1560
cgcaccatgg cgtgtggtat cgctggtctg tccgttgctg ctgactccct gtctgcaatc    1620
aaatatgcga aagttaaacc gattcgtgac gaagacggtc tggctatcga cttcgaaatc    1680
gaaggcgaat accccgcagtt tggtaacaat gatccgcgtg tagatgacct ggctgttgac    1740
ctggtagaac gtttcatgaa gaaaattcag aaactgcaca cctaccgtga cgctatcccg    1800
actcagtctg ttctgaccat cacttctaac gttgtgtatg gtaagaaaac gggtaacacc    1860
ccagacggtc gtcgtgctgg cgcgccgttc ggaccgggtg ctaacccgat gcacggtcgt    1920
gaccagaaag gtgcagtagc ctctctgact tccgttgcta aactgccgtt tgcttacgct    1980
aaagatggta tctcctacac cttctctatc gttccgaacg cactgggtaa agacgacgaa    2040
gttcgtaaga ccaacctggc tggtctgatg gatggttact tccaccacga agcatccatc    2100
gaaggtggtc agcacctgaa cgttaacgtg atgaaccgtg aaatgctgct cgacgcgatg    2160
gaaaacccgg aaaaatatcc gcagctgacc atccgtgtat ctggctacgc agtacgtttc    2220
aactcgctga ctaaagaaca gcagcaggac gttattactc gtaccttcac tcaatctatg    2280
taa                                                                  2283
```

<210> SEQ ID NO 42
<211> LENGTH: 760
<212> TYPE: PRT
<213> ORGANISM: Escherichia coli

<400> SEQUENCE: 42

Met Ser Glu Leu Asn Glu Lys Leu Ala Thr Ala Trp Glu Gly Phe Thr
1               5                   10                  15

```
Lys Gly Asp Trp Gln Asn Glu Val Asn Val Arg Asp Phe Ile Gln Lys
             20                  25                  30

Asn Tyr Thr Pro Tyr Glu Gly Asp Glu Ser Phe Leu Ala Gly Ala Thr
             35                  40                  45

Glu Ala Thr Thr Thr Leu Trp Asp Lys Val Met Glu Gly Val Lys Leu
 50                  55                  60

Glu Asn Arg Thr His Ala Pro Val Asp Phe Asp Thr Ala Val Ala Ser
 65                  70                  75                  80

Thr Ile Thr Ser His Asp Ala Gly Tyr Ile Asn Lys Gln Leu Glu Lys
                 85                  90                  95

Ile Val Gly Leu Gln Thr Glu Ala Pro Leu Lys Arg Ala Leu Ile Pro
            100                 105                 110

Phe Gly Gly Ile Lys Met Ile Glu Gly Ser Cys Lys Ala Tyr Asn Arg
            115                 120                 125

Glu Leu Asp Pro Met Ile Lys Lys Ile Phe Thr Glu Tyr Arg Lys Thr
            130                 135                 140

His Asn Gln Gly Val Phe Asp Val Tyr Thr Pro Asp Ile Leu Arg Cys
145                 150                 155                 160

Arg Lys Ser Gly Val Leu Thr Gly Leu Pro Asp Ala Tyr Gly Arg Gly
                165                 170                 175

Arg Ile Ile Gly Asp Tyr Arg Arg Val Ala Leu Tyr Gly Ile Asp Tyr
                180                 185                 190

Leu Met Lys Asp Lys Leu Ala Gln Phe Thr Ser Leu Gln Ala Asp Leu
            195                 200                 205

Glu Asn Gly Val Asn Leu Glu Gln Thr Ile Arg Leu Arg Glu Glu Ile
            210                 215                 220

Ala Glu Gln His Arg Ala Leu Gly Gln Met Lys Glu Met Ala Ala Lys
225                 230                 235                 240

Tyr Gly Tyr Asp Ile Ser Gly Pro Ala Thr Asn Ala Gln Glu Ala Ile
                245                 250                 255

Gln Trp Thr Tyr Phe Gly Tyr Leu Ala Ala Val Lys Ser Gln Asn Gly
            260                 265                 270

Ala Ala Met Ser Phe Gly Arg Thr Ser Thr Phe Leu Asp Val Tyr Ile
            275                 280                 285

Glu Arg Asp Leu Lys Ala Gly Lys Ile Thr Glu Gln Glu Ala Gln Glu
290                 295                 300

Met Val Asp His Leu Val Met Lys Leu Arg Met Val Arg Phe Leu Arg
305                 310                 315                 320

Thr Pro Glu Tyr Asp Glu Leu Phe Ser Gly Asp Pro Ile Trp Ala Thr
                325                 330                 335

Glu Ser Ile Gly Gly Met Gly Leu Asp Gly Arg Thr Leu Val Thr Lys
            340                 345                 350

Asn Ser Phe Arg Phe Leu Asn Thr Leu Tyr Thr Met Gly Pro Ser Pro
            355                 360                 365

Glu Pro Asn Met Thr Ile Leu Trp Ser Glu Lys Leu Pro Leu Asn Phe
            370                 375                 380

Lys Lys Phe Ala Ala Lys Val Ser Ile Asp Thr Ser Ser Leu Gln Tyr
385                 390                 395                 400

Glu Asn Asp Asp Leu Met Arg Pro Asp Phe Asn Asp Asp Tyr Ala
                    405                 410                 415

Ile Ala Cys Cys Val Ser Pro Met Ile Val Gly Lys Gln Met Gln Phe
            420                 425                 430

Phe Gly Ala Arg Ala Asn Leu Ala Lys Thr Met Leu Tyr Ala Ile Asn
```

| | | | | 435 | | | | 440 | | | | 445 | | |
|---|---|---|---|---|---|---|---|---|---|---|---|---|---|---|
Gly Gly Val Asp Glu Lys Leu Lys Met Gln Val Gly Pro Lys Ser Glu
   450                     455                     460

Pro Ile Lys Gly Asp Val Leu Asn Tyr Asp Glu Val Met Glu Arg Met
465                     470                     475                     480

Asp His Phe Met Asp Trp Leu Ala Lys Gln Tyr Ile Thr Ala Leu Asn
               485                     490                     495

Ile Ile His Tyr Met His Asp Lys Tyr Ser Tyr Glu Ala Ser Leu Met
           500                     505                     510

Ala Leu His Asp Arg Asp Val Ile Arg Thr Met Ala Cys Gly Ile Ala
       515                     520                     525

Gly Leu Ser Val Ala Ala Asp Ser Leu Ser Ala Ile Lys Tyr Ala Lys
   530                     535                     540

Val Lys Pro Ile Arg Asp Glu Asp Gly Leu Ala Ile Asp Phe Glu Ile
545                     550                     555                     560

Glu Gly Glu Tyr Pro Gln Phe Gly Asn Asn Asp Pro Arg Val Asp Asp
               565                     570                     575

Leu Ala Val Asp Leu Val Glu Arg Phe Met Lys Lys Ile Gln Lys Leu
           580                     585                     590

His Thr Tyr Arg Asp Ala Ile Pro Thr Gln Ser Val Leu Thr Ile Thr
       595                     600                     605

Ser Asn Val Val Tyr Gly Lys Lys Thr Gly Asn Thr Pro Asp Gly Arg
   610                     615                     620

Arg Ala Gly Ala Pro Phe Gly Pro Gly Ala Asn Pro Met His Gly Arg
625                     630                     635                     640

Asp Gln Lys Gly Ala Val Ala Ser Leu Thr Ser Val Ala Lys Leu Pro
               645                     650                     655

Phe Ala Tyr Ala Lys Asp Gly Ile Ser Tyr Thr Phe Ser Ile Val Pro
           660                     665                     670

Asn Ala Leu Gly Lys Asp Asp Glu Val Arg Lys Thr Asn Leu Ala Gly
       675                     680                     685

Leu Met Asp Gly Tyr Phe His His Glu Ala Ser Ile Glu Gly Gly Gln
   690                     695                     700

His Leu Asn Val Asn Val Met Asn Arg Glu Met Leu Leu Asp Ala Met
705                     710                     715                     720

Glu Asn Pro Glu Lys Tyr Pro Gln Leu Thr Ile Arg Val Ser Gly Tyr
               725                     730                     735

Ala Val Arg Phe Asn Ser Leu Thr Lys Glu Gln Gln Gln Asp Val Ile
           740                     745                     750

Thr Arg Thr Phe Thr Gln Ser Met
       755                     760

<210> SEQ ID NO 43
<211> LENGTH: 768
<212> TYPE: DNA
<213> ORGANISM: Escherichia coli

<400> SEQUENCE: 43
atgggccaca tctggagaaa caccgcaatg tcagttattg gtcgcattca ctccttttgaa     60 tcctgtggaa ccgtagacgg cccgggtatt cgctttatca cctttttcca gggctgcctg    120
atgcgctgcc tgtattgtca taaccgcgac acctgggata cgcatggcgg taagaagtt    180 accgttgaag atttgatgaa ggaagtggtg acctatcgcc actttatgaa cgcttccggc    240
ggcggcgtta ccgcatccgg cggtgaggca atcctacaag ctgagtttgt tcgtgactgg    300

```
ttccgcgcct gcaaaaaaga aggcattcat acctgtctgg acaccaacgg ttttgttcgt    360
cgttacgatc cggtgattga tgaactgctg gaagtaaccg acctggtaat gctcgatctc    420
aaacagatga acgacgagat ccaccaaaat ctggttggag tttccaacca ccgcacgctg    480
gagttcgcta aatatctggc gaacaaaaat gtgaaggtgt ggatccgcta tgttgttgtc    540
ccaggctggt ctgacgatga cgattcagcg catcgccttg gtgaatttac ccgtgatatg    600
ggcaacgttg agaaaatcga gctcctcccc taccacgaac tgggcaaaca caaatgggtg    660
gcaatgggtg aagaatacaa actcgatggt gttaaaccac cgaagaaaga gaccatggaa    720
cgcgtgaaag gcattcttga gcagtacggt cataaggtca tgttctaa    768
```

<210> SEQ ID NO 44
<211> LENGTH: 255
<212> TYPE: PRT
<213> ORGANISM: Escherichia coli

<400> SEQUENCE: 44

```
Met Gly His Ile Trp Arg Asn Thr Ala Met Ser Val Ile Gly Arg Ile
1               5                   10                  15

His Ser Phe Glu Ser Cys Gly Thr Val Asp Gly Pro Gly Ile Arg Phe
            20                  25                  30

Ile Thr Phe Phe Gln Gly Cys Leu Met Arg Cys Leu Tyr Cys His Asn
        35                  40                  45

Arg Asp Thr Trp Asp Thr His Gly Gly Lys Glu Val Thr Val Glu Asp
    50                  55                  60

Leu Met Lys Glu Val Val Thr Tyr Arg His Phe Met Asn Ala Ser Gly
65                  70                  75                  80

Gly Gly Val Thr Ala Ser Gly Gly Glu Ala Ile Leu Gln Ala Glu Phe
                85                  90                  95

Val Arg Asp Trp Phe Arg Ala Cys Lys Lys Glu Gly Ile His Thr Cys
            100                 105                 110

Leu Asp Thr Asn Gly Phe Val Arg Arg Tyr Asp Pro Val Ile Asp Glu
        115                 120                 125

Leu Leu Glu Val Thr Asp Leu Val Met Leu Asp Leu Lys Gln Met Asn
    130                 135                 140

Asp Glu Ile His Gln Asn Leu Val Gly Val Ser Asn His Arg Thr Leu
145                 150                 155                 160

Glu Phe Ala Lys Tyr Leu Ala Asn Lys Asn Val Lys Val Trp Ile Arg
                165                 170                 175

Tyr Val Val Val Pro Gly Trp Ser Asp Asp Asp Ser Ala His Arg
            180                 185                 190

Leu Gly Glu Phe Thr Arg Asp Met Gly Asn Val Glu Lys Ile Glu Leu
        195                 200                 205

Leu Pro Tyr His Glu Leu Gly Lys His Lys Trp Val Ala Met Gly Glu
    210                 215                 220

Glu Tyr Lys Leu Asp Gly Val Lys Pro Pro Lys Lys Glu Thr Met Glu
225                 230                 235                 240

Arg Val Lys Gly Ile Leu Glu Gln Tyr Gly His Lys Val Met Phe
                245                 250                 255
```

<210> SEQ ID NO 45
<211> LENGTH: 1707
<212> TYPE: DNA
<213> ORGANISM: Zymomonas mobilis
<220> FEATURE:

```
<221> NAME/KEY: misc_feature
<222> LOCATION: (622)..(622)
<223> OTHER INFORMATION: n is a, c, g, or t

<400> SEQUENCE: 45
atgagttata ctgtcggtac ctatttagcg gagcggcttg tccagattgg tctcaagcat      60
cacttcgcag tcgcgggcga ctacaacctc gtccttcttg acaacctgct tttgaacaaa     120
aacatggagc aggtttattg ctgtaacgaa ctgaactgcg gtttcagtgc agaaggttat     180
gctcgtgcca aaggcgcagc agcagccgtc gttacctaca gcgtcggtgc gctttccgca     240
tttgatgcta tcggtggcgc ctatgcagaa aaccttccgg ttatcctgat ctccggtgct     300
ccgaacaaca atgaccacgc tgctggtcac gtgttgcatc acgctcttgg caaaaccgac     360
tatcactatc agttggaaat ggccaagaac atcacggccg ccgctgaagc gatttatacc     420
ccggaagaag ctccggctaa aatcgatcac gtgattaaaa ctgctcttcg tgagaagaag     480
ccggtttatc tcgaaatcgc ttgcaacatt gcttccatgc cctgcgccgc tcctggaccg     540
gcaagcgcat tgttcaatga cgaagccagc gacgaagctt ctttgaatgc agcggttgaa     600
gaaaccctga aattcatcgc cnaccgcgac aaagttgccg tcctcgtcgg cagcaagctg     660
cgcgcagctg gtgctgaaga gctgctgtc aaatttgctg atgctcttgg tggcgcagtt     720
gctaccatgg ctgctgcaaa aagcttcttc ccagaagaaa accgcatta catcggtacc     780
tcatggggtg aagtcagcta tccgggcgtt gaaaagacga tgaaagaagc cgatgcggtt     840
atcgctctgg ctcctgtctt taacgactac tccaccactg gttggacgga tattcctgat     900
cctaagaaac tggttctcgc tgaaccgcgt tctgtcgtcg ttaacggcat tcgcttcccc     960
agcgtccatc tgaaagacta tctgacccgt ttggctcaga agtttccaa gaaaaccggt    1020
gctttggact tcttcaaatc cctcaatgca ggtgaactga agaaagccgc tccggctgat    1080
ccgagtgctc cgttggtcaa cgcagaaatc gcccgtcagg tcgaagctct tctgaccccg    1140
aacacgacgg ttattgctga aaccggtgac tcttggttca atgctcagcg catgaagctc    1200
ccgaacggtg ctcgcgttga atatgaaatg cagtggggtc acattggttg gtccgttcct    1260
gccgccttcg gttatgccgt cggtgctccg gaacgtcgca acatcctcat ggttggtgat    1320
ggttccttcc agctgacggc tcaggaagtc gctcagatgg ttcgcctgaa actgccggtt    1380
atcatcttct tgatcaataa ctatggttac accatcgaag ttatgatcca tgatggtccg    1440
tacaacaaca tcaagaactg ggattatgcc ggtctgatgg aagtgttcaa cggtaacggt    1500
ggttatgaca gcggtgctgg taaaggcctg aaggctaaaa ccggtggcga actggcagaa    1560
gctatcaagg ttgctctggc aaacaccgac ggcccaaccc tgatcgaatg cttcatcggt    1620
cgtgaagact gcactgaaga attggtcaaa tggggtaagc gcgttgctgc cgccaacagc    1680
cgtaagcctg ttaacaagct cctctag                                        1707

<210> SEQ ID NO 46
<211> LENGTH: 568
<212> TYPE: PRT
<213> ORGANISM: Zymomonas mobilis
<220> FEATURE:
<221> NAME/KEY: misc_feature
<222> LOCATION: (208)..(208)
<223> OTHER INFORMATION: Xaa can be any naturally occurring amino acid

<400> SEQUENCE: 46

Met Ser Tyr Thr Val Gly Thr Tyr Leu Ala Glu Arg Leu Val Gln Ile
1               5                   10                  15
```

```
Gly Leu Lys His His Phe Ala Val Ala Gly Asp Tyr Asn Leu Val Leu
            20                  25                  30

Leu Asp Asn Leu Leu Leu Asn Lys Asn Met Glu Gln Val Tyr Cys Cys
        35                  40                  45

Asn Glu Leu Asn Cys Gly Phe Ser Ala Glu Gly Tyr Ala Arg Ala Lys
50                      55                  60

Gly Ala Ala Ala Val Val Thr Tyr Ser Val Gly Ala Leu Ser Ala
65                  70                  75                  80

Phe Asp Ala Ile Gly Gly Ala Tyr Ala Glu Asn Leu Pro Val Ile Leu
                85                  90                  95

Ile Ser Gly Ala Pro Asn Asn Asn Asp His Ala Ala Gly His Val Leu
            100                 105                 110

His His Ala Leu Gly Lys Thr Asp Tyr His Tyr Gln Leu Glu Met Ala
        115                 120                 125

Lys Asn Ile Thr Ala Ala Ala Glu Ala Ile Tyr Thr Pro Glu Glu Ala
130                 135                 140

Pro Ala Lys Ile Asp His Val Ile Lys Thr Ala Leu Arg Glu Lys Lys
145                 150                 155                 160

Pro Val Tyr Leu Glu Ile Ala Cys Asn Ile Ala Ser Met Pro Cys Ala
                165                 170                 175

Ala Pro Gly Pro Ala Ser Ala Leu Phe Asn Asp Glu Ala Ser Asp Glu
            180                 185                 190

Ala Ser Leu Asn Ala Ala Val Glu Glu Thr Leu Lys Phe Ile Ala Xaa
        195                 200                 205

Arg Asp Lys Val Ala Val Leu Val Gly Ser Lys Leu Arg Ala Ala Gly
210                 215                 220

Ala Glu Glu Ala Ala Val Lys Phe Ala Asp Ala Leu Gly Gly Ala Val
225                 230                 235                 240

Ala Thr Met Ala Ala Lys Ser Phe Phe Pro Glu Glu Asn Pro His
                245                 250                 255

Tyr Ile Gly Thr Ser Trp Gly Glu Val Ser Tyr Pro Gly Val Glu Lys
            260                 265                 270

Thr Met Lys Glu Ala Asp Ala Val Ile Ala Leu Ala Pro Val Phe Asn
        275                 280                 285

Asp Tyr Ser Thr Thr Gly Trp Thr Asp Ile Pro Asp Pro Lys Lys Leu
290                 295                 300

Val Leu Ala Glu Pro Arg Ser Val Val Asn Gly Ile Arg Phe Pro
305                 310                 315                 320

Ser Val His Leu Lys Asp Tyr Leu Thr Arg Leu Ala Gln Lys Val Ser
                325                 330                 335

Lys Lys Thr Gly Ala Leu Asp Phe Phe Lys Ser Leu Asn Ala Gly Glu
            340                 345                 350

Leu Lys Lys Ala Ala Pro Ala Asp Pro Ser Ala Pro Leu Val Asn Ala
        355                 360                 365

Glu Ile Ala Arg Gln Val Glu Ala Leu Leu Thr Pro Asn Thr Thr Val
370                 375                 380

Ile Ala Glu Thr Gly Asp Ser Trp Phe Asn Ala Gln Arg Met Lys Leu
385                 390                 395                 400

Pro Asn Gly Ala Arg Val Glu Tyr Glu Met Gln Trp Gly His Ile Gly
                405                 410                 415

Trp Ser Val Pro Ala Ala Phe Gly Tyr Ala Val Gly Ala Pro Glu Arg
            420                 425                 430

Arg Asn Ile Leu Met Val Gly Asp Gly Ser Phe Gln Leu Thr Ala Gln
```

|   |   |   | 435 |   |   |   | 440 |   |   |   | 445 |   |
|---|---|---|---|---|---|---|---|---|---|---|---|---|

Glu Val Ala Gln Met Val Arg Leu Lys Leu Pro Val Ile Ile Phe Leu
450                 455                 460

Ile Asn Asn Tyr Gly Tyr Thr Ile Glu Val Met Ile His Asp Gly Pro
465             470                 475                 480

Tyr Asn Asn Ile Lys Asn Trp Asp Tyr Ala Gly Leu Met Glu Val Phe
            485                 490                 495

Asn Gly Asn Gly Gly Tyr Asp Ser Gly Ala Lys Gly Leu Lys Ala
            500                 505                 510

Lys Thr Gly Gly Glu Leu Ala Glu Ala Ile Lys Val Ala Leu Ala Asn
        515                 520                 525

Thr Asp Gly Pro Thr Leu Ile Glu Cys Phe Ile Gly Arg Glu Asp Cys
    530                 535                 540

Thr Glu Glu Leu Val Lys Trp Gly Lys Arg Val Ala Ala Ala Asn Ser
545                 550                 555                 560

Arg Lys Pro Val Asn Lys Leu Leu
            565

<210> SEQ ID NO 47
<211> LENGTH: 1152
<212> TYPE: DNA
<213> ORGANISM: Zymomonas mobilis

<400> SEQUENCE: 47
atggcttctt caacttttta tattcctttc gtcaacgaaa tgggcgaagg ttcgcttgaa      60
aaagcaatca aggatcttaa cggcagcggc tttaaaaatg cgctgatcgt ttctgatgct     120
ttcatgaaca atccggtgt tgtgaagcag gttgctgacc tgttgaaagc acagggtatt     180
aattctgctg tttatgatgg cgttatgccg aacccgactg ttaccgcagt tctggaaggc     240
cttaagatcc tgaaggataa caattcagac ttcgtcatct ccctcggtgg tggttctccc     300
catgactgcg ccaaagccat cgctctggtc gcaaccaatg gtggtgaagt caaagactac     360
gaaggtatcg acaaatctaa gaaacctgcc ctgcctttga tgtcaatcaa cacgacggct     420
ggtacggctt ctgaaatgac gcgtttctgc atcatcactg atgaagtccg tcacgttaag     480
atggccattg ttgaccgtca cgttaccccg atggtttccg tcaacgatcc tctgttgatg     540
gttggtatgc caaaaggcct gaccgccgcc accggtatgg atgctctgac ccacgcattt     600
gaagcttatt cttcaacggc agctactccg atcaccgatg cttgcgcctt gaaggctgcg     660
tccatgatcg ctaagaatct gaagaccgct tgcgacaacg gtaaggatat gccagctcgt     720
gaagctatgg cttatgccca attcctcgct ggtatggcct tcaacaacgc ttcgcttggt     780
tatgtccatg ctatggctca ccagttgggc ggctactaca acctgccgca tggtgtctgc     840
aacgctgttc tgcttccgca tgttctggct tataacgcct ctgtcgttgc tggtcgtctg     900
aaagacgttg gtgttgctat gggtctcgat atcgccaatc tcggtgataa agaaggcgca     960
gaagccacca tccaggctgt tcgcgatctg gctgcttcca ttggtattcc agcaaatctg    1020
accgagctgg gtgctaagaa agaagatgtg ccgcttcttg ctgaccacgc tctgaaagat    1080
gcttgtgctc tgaccaaccc gcgtcagggt gatcagaaag aagttgaaga actcttcctg    1140 agcgcttttct aa                                                       1152

<210> SEQ ID NO 48
<211> LENGTH: 383
<212> TYPE: PRT
<213> ORGANISM: Zymomonas mobilis

<400> SEQUENCE: 48

Met Ala Ser Ser Thr Phe Tyr Ile Pro Phe Val Asn Glu Met Gly Glu
1               5                   10                  15

Gly Ser Leu Glu Lys Ala Ile Lys Asp Leu Asn Gly Ser Gly Phe Lys
            20                  25                  30

Asn Ala Leu Ile Val Ser Asp Ala Phe Met Asn Lys Ser Gly Val Val
        35                  40                  45

Lys Gln Val Ala Asp Leu Leu Lys Ala Gln Gly Ile Asn Ser Ala Val
    50                  55                  60

Tyr Asp Gly Val Met Pro Asn Pro Thr Val Thr Ala Val Leu Glu Gly
65                  70                  75                  80

Leu Lys Ile Leu Lys Asp Asn Ser Asp Phe Val Ile Ser Leu Gly
                85                  90                  95

Gly Gly Ser Pro His Asp Cys Ala Lys Ala Ile Ala Leu Val Ala Thr
            100                 105                 110

Asn Gly Gly Glu Val Lys Asp Tyr Glu Gly Ile Asp Lys Ser Lys Lys
            115                 120                 125

Pro Ala Leu Pro Leu Met Ser Ile Asn Thr Thr Ala Gly Thr Ala Ser
    130                 135                 140

Glu Met Thr Arg Phe Cys Ile Ile Thr Asp Glu Val Arg His Val Lys
145                 150                 155                 160

Met Ala Ile Val Asp Arg His Val Thr Pro Met Val Ser Val Asn Asp
                165                 170                 175

Pro Leu Leu Met Val Gly Met Pro Lys Gly Leu Thr Ala Ala Thr Gly
            180                 185                 190

Met Asp Ala Leu Thr His Ala Phe Glu Ala Tyr Ser Ser Thr Ala Ala
            195                 200                 205

Thr Pro Ile Thr Asp Ala Cys Ala Leu Lys Ala Ala Ser Met Ile Ala
    210                 215                 220

Lys Asn Leu Lys Thr Ala Cys Asp Asn Gly Lys Asp Met Pro Ala Arg
225                 230                 235                 240

Glu Ala Met Ala Tyr Ala Gln Phe Leu Ala Gly Met Ala Phe Asn Asn
                245                 250                 255

Ala Ser Leu Gly Tyr Val His Ala Met Ala His Gln Leu Gly Gly Tyr
            260                 265                 270

Tyr Asn Leu Pro His Gly Val Cys Asn Ala Val Leu Leu Pro His Val
            275                 280                 285

Leu Ala Tyr Asn Ala Ser Val Val Ala Gly Arg Leu Lys Asp Val Gly
    290                 295                 300

Val Ala Met Gly Leu Asp Ile Ala Asn Leu Gly Asp Lys Glu Gly Ala
305                 310                 315                 320

Glu Ala Thr Ile Gln Ala Val Arg Asp Leu Ala Ala Ser Ile Gly Ile
                325                 330                 335

Pro Ala Asn Leu Thr Glu Leu Gly Ala Lys Lys Glu Asp Val Pro Leu
            340                 345                 350

Leu Ala Asp His Ala Leu Lys Asp Ala Cys Ala Leu Thr Asn Pro Arg
            355                 360                 365

Gln Gly Asp Gln Lys Glu Val Glu Glu Leu Phe Leu Ser Ala Phe
    370                 375                 380